(12) United States Patent
Monaghan et al.

(10) Patent No.: US 6,207,678 B1
(45) Date of Patent: Mar. 27, 2001

(54) QUATERNARY AMMONIUM COMPOUNDS AS TACHYKININ ANTAGONISTS

(75) Inventors: Sandra Marina Monaghan; David Alker, both of Sandwich (GB); Christopher John Burns, Sydney (AU)

(73) Assignee: Pfizer INC, New York, NY (US)

( * ) Notice: Subject to any disclaimer, the term of this patent is extended or adjusted under 35 U.S.C. 154(b) by 0 days.

(21) Appl. No.: 09/380,370

(22) PCT Filed: Jun. 5, 1998

(86) PCT No.: PCT/EP98/03500

§ 371 Date: Apr. 24, 2000

§ 102(e) Date: Apr. 24, 2000

(87) PCT Pub. No.: WO98/57972

PCT Pub. Date: Dec. 23, 1998

(30) Foreign Application Priority Data

Jun. 18, 1997 (GB) .................................................. 9712882

(51) Int. Cl.[7] ....................... A61K 31/439; C07D 453/02
(52) U.S. Cl. ............................................. 514/305; 546/133
(58) Field of Search .............................. 514/305; 546/133

(56) References Cited

U.S. PATENT DOCUMENTS

| 3,991,201 | 11/1976 | Heeres et al. | 424/273 |
| 5,583,134 | * 12/1996 | Emonds-Alt et al. | 514/212 |

FOREIGN PATENT DOCUMENTS

| 0591040 | 4/1994 | (EP) | C07C/453/02 |

* cited by examiner

Primary Examiner—C. S. Aulakh
(74) Attorney, Agent, or Firm—Peter C. Richardson; Paul H. Ginsburg; Roy F. Waldron

(57) ABSTRACT

The present invention provides a compound of formula (I) wherein R is phenyl, $C_3$–$C_7$ cycloalkyl or heteroaryl, each of which being optionally benzo- or $C_3$–$C_7$ cycloalkyl-fused and optionally substituted, including in the benzo- or $C_3$–$C_7$ cycloalkyl-fused portion, by from 1 to 3 substituents each independently selected from $C_1$–$C_4$ alkyl, fluoro($C_1$–$C_4$) alkyl, $C_1$–$C_4$ alkoxy, fluoro($C_1$–$C_4$)alkoxy, phenoxy, $C_2$–$C_4$ alkanoyl, halo, $C_1$–$C_4$ alkoxycarbonyl, $C_3$–$C_7$ cycloalkyl, —S(O)$_m$($C_1$–$C_4$ alkyl), cyano, —NR$^2$R$^3$, —S(O)$_m$NR$^2$R$^3$, —NR$^4$($C_1$–$C_4$ alkanoyl) and —CONR$^2$R$^3$, or R is 2,3-dihydrobenzo[b]furanyl or chromanyl; R$^1$ is H or $C_1$–$C_6$ alkyl; W is a direct link, methylene or ethylene; X is unbranched $C_2$–$C_4$ alkylene; Y is phenyl, naphthyl, benzyl, pyridyl, thienyl or $C_3$–$C_7$ cycloalkyl, each of which being optionally substituted by from 1 to 3 substituents each independently selected from $C_1$–$C_4$ alkyl, fluoro($C_1$–$C_4$) alkyl, $C_1$–$C_4$ alkoxy, fluoro($C_1$–$C_4$)alkoxy, halo and cyano; Ar is phenyl, naphthyl, benzyl, thienyl, benzo[b]thienyl or indolyl, each of which being optionally substituted by from 1 to 3 substituents each independently selected from $C_1$–$C_4$ alkyl, fluoro($C_1$–$C_4$)alkyl, $C_1$–$C_4$ alkoxy, fluoro($C_1$–$C_4$) alkoxy, halo and cyano, or Ar is 1,3-benzodioxolan-4 or 5-yl or 1,4-benzodioxan-5 or 6-yl; $Z^A$ is a pharmaceutically acceptable anion; with the proviso that when W is a direct link and R is optionally fused and optionally substituted heteroaryl, said heteroaryl is linked by a ring carbon atom to the carbonyl group. The compounds are tachykinin antagonists.

28 Claims, No Drawings

QUATERNARY AMMONIUM COMPOUNDS AS TACHYKININ ANTAGONISTS

This application is a 371 of PCT/EP 98/03500 filed Jun. 5, 1998 now WO98/57972 filed Dec. 23, 1998.

This invention relates to quaternary ammonium compounds. More particularly, this invention relates to 1-(2-acylimidazol-1-ylalkyl)quinuclidinium salts and to processes for the preparation of, intermediates used in the preparation of, compositions containing and the uses of, such salts.

The present compounds are antagonists of tachykinins, including NKA (neurokinin A), NKB (neurokinin B) and Substance P, acting at the human neurokinin-1($NK_1$), neurokinin-2 ($NK_2$) and neurokinin-3 ($NK_3$) receptors.

These compounds are particularly useful as dual $NK_1$ and $NK_2$ receptor antagonists and can therefore be used for treating an inflammatory disease such as arthritis, psoriasis, asthma or inflammatory bowel disease, a central nervous system (CNS) disorder such as anxiety, depression, dementia or psychosis, a gastrointestinal (GI) disorder such as functional bowel disease, irritable bowel syndrome, gastro-oesophageal reflux, faecal incontinence, colitis or Crohn's disease, a disease caused by *Helicobacter pylori* or another urease-positive Gram negative bacteria, a urogenital tract disorder such as incontinence, impotence, hyperreflexia or cystitis, a pulmonary disorder such as chronic obstructive airways disease, an allergy such as eczema, contact dermatitis, atopic dermatitis, urticaria, eczematoid dermatitis or rhinitis, a hypersensitivity disorder such as to poison ivy, a proliferative disorder such as a cancer or a disorder involving fibroblast proliferation, a vasospastic disease such as angiogenesis, angina or Reynaud's disease, a fibrosing or collagen disease such as atherosclerosis, scleroderma or eosinophilic fascioliasis, reflux sympathetic dystrophy such as shoulder/hand syndrome, an addiction disorder such as alcoholism, a stress-related somatic disorder, a peripheral neuropathy such as diabetic neuropathy, neuralgia, causalgia, painful neuropathy, a burn, herpetic neuralgia or post-herpefic neuralgia, a neuropathological disorder such as Alzheimer's disease or multiple sclerosis, a disorder related to immune enhancement or suppression such as systemic lupus erythematosis, a rheumatic disease such as fibrositis, emesis, cough, acute or chronic pain, migraine, an ophthalmic disease such as proliferative retinopathy, influenza or a cold.

EP-A-680962 and EP-A-0739891 disclose heterocyclic compounds which are non-peptide antagonists of NKA and that are useful for the treatment of diseases such as asthma. EP-A-0591040 discloses quaternary compounds with tachykinin antagonist activity.

The present invention provides compounds of the formula:

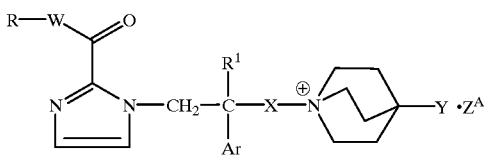

(I)

wherein

R is phenyl, $C_3$–$C_7$ cycloalkyl or heteroaryl, each of which being optionally benzo- or $C_3$–$C_7$ cycloalkyl-fused and optionally substituted, including in the benzo- or $C_3$–$C_7$ cycloalkyl-fused portion, by from 1 to 3 substituents each independently selected from $C_1$–$C_4$ alkyl, fluoro($C_1$–$C_4$)alkyl, $C_1$–$C_4$ alkoxy, fluoro($C_1$–$C_4$)alkoxy, phenoxy, $C_2$–$C_4$ alkanoyl, halo, $C_1$–$C_4$ alkoxycarbonyl, $C_3$–$C_7$ cycloalkyl, —S(O)$_m$($C_1$–$C_4$ alkyl), cyano, —NR$^2$R$^3$, —S(O)$_m$NR$^2$R$^3$, —NR$^4$($C_1$–$C_4$ alkanoyl) and —CONR$^2$R$^3$, or R is 2,3-dihydrobenzo[b]furanyl or chromanyl;

R$^1$ is H or $C_1$–$C_6$ alkyl;

R$^2$ and R$^3$ are either each independently selected from H and $C_1$–$C_6$ alkyl, or when taken together, represent $C_4$–$C_6$ alkylene;

R$^4$ is H or $C_1$–$C_6$ alkyl;

W is a direct link, methylene or ethylene;

X is unbranched $C_2$–$C_4$ alkylene;

Y is phenyl, naphthyl, benzyl, pyridyl, thienyl or $C_3$–$C_7$ cycloalkyl, each of which being optionally substituted by from 1 to 3 substituents each independently selected from $C_1$–$C_4$ alkyl, fluoro($C_1$–$C_4$)alkyl, $C_1$–$C_4$ alkoxy, fluoro($C_1$–$C_4$)alkoxy, halo and cyano;

Ar is phenyl, naphthyl, benzyl, thienyl, benzo[b]thienyl or indolyl, each of which being optionally substituted by from 1 to 3 substituents each independently selected from $C_1$–$C_4$ alkyl, fluoro($C_1$–$C_4$)alkyl, $C_1$–$C_4$ alkoxy, fluoro($C_1$–$C_4$)alkoxy, halo and cyano, or Ar is 1,3-benzodioxolan-4 or 5-yl or 1,4-benzodioxan-5 or 6-yl;

m is 0, 1 or 2;

$Z^A$ is a pharmaceutically acceptable anion;

and "heteroaryl", used in the definition of R, means thienyl or a 5- or 6-membered ring heteroaryl group containing either from 1 to 4 nitrogen heteroatoms, or 1 or 2 nitrogen heteroatom(s) and 1 oxygen or sulphur heteroatom, with the proviso that when W is a direct link and R is optionally fused and optionally substituted heteroaryl, said heteroaryl is linked by a ring carbon atom to the carbonyl group.

In the above definitions, "halo" means fluoro, chloro, bromo or iodo and alkyl and alkoxy groups having three or more carbon atoms, alkanoyl groups having four carbon atoms and alkylene groups having two or more carbon atoms (except where stated) may be unbranched- or branched-chain.

$Z^A$ is a pharmaceutically acceptable anion such as chloride, bromide, nitrate, methanesulphonate, para-toluenesulphonate, benzenesulphonate, hydrogen sulphate or sulphate.

Preferably, $Z^A$ is chloride or methanesulphonate.

Most preferably, $Z^A$ is methanesulphonate.

A compound of the formula (I) contains one or more asymmetric carbon atoms and therefore exists in two or more stereoisomeric forms. The present invention includes the individual stereoisomers of the compounds of the formula (I) and mixtures thereof.

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid.

Preferably, R is phenyl which is optionally benzo- or $C_3$–$C_7$ cycloalkyl-fused and optionally substituted, including in the benzo- or $C_3$–$C_7$ cycloalkyl-fused portion, by 1, 2 or 3 substituents each independently selected from $C_1$–$C_4$ alkyl, fluoro($C_1$–$C_4$)alkyl, $C_1$–$C_4$ alkoxy, fluoro($C_1$–$C_4$) alkoxy, phenoxy and halo, or R is 2,3-dihydrobenzo[b]furanyl.

More preferably, R is phenyl which is optionally benzo- or $C_3$–$C_7$ cycloalkyl-fused and optionally substituted, including in the benzo- or $C_3$–$C_7$ cycloalkyl-fused portion, by 1, 2 or 3 substituents each independently selected from methyl, ethyl, trifluoromethyl, methoxy, isopropoxy, trifluoromethoxy, phenoxy, fluoro and chloro, or R is 2,3-dihydrobenzo[b]furanyl.

Yet more preferably, R is phenyl, naphthyl or tetrahydronaphthyl, each of which being optionally substituted by 1, 2 or 3 substituents each independently selected from methyl, ethyl, trifluoromethyl, methoxy, isopropoxy, trifluoromethoxy, phenoxy, fluoro and chloro, or R is 2,3-dihydrobenzo[b]furanyl.

Yet further preferably, R is phenyl, 3,5-dimethylphenyl, 2,3-dimethylphenyl, 2-trifluoromethoxyphenyl, 2-methoxy-3-methylphenyl, 2,3-dihydrobenzo[b]furan-7-yl, naphth-2-yl, 4-fluoro-3-trifluoromethylphenyl, 1,2,3,4-tetrahydronaphth-5-yl, 1,2,3,4-tetrahydronaphth-6-yl, 5-chloro-2-methoxyphenyl, 2-methoxyphenyl, 2-trifluoromethylphenyl, 2-isopropoxyphenyl, 2-ethylphenyl, 2-phenoxyphenyl or 3,5-bis(trifluoromethyl) phenyl.

Most preferably, R is 2,3-dimethylphenyl, naphth-2-yl, 1,2,3,4-tetrahydronaphth-5-yl or 2-methoxyphenyl.

Preferably, $R^1$ is H.

Preferably, W is a direct link or methylene.

Most preferably, W is a direct link.

Preferably, X is 1,2-ethylene.

Preferably, Y is phenyl, naphthyl or cyclohexyl, each of which being optionally substituted by 1, 2 or 3 $C_1$–$C_4$ alkyl substituents.

More preferably, Y is phenyl, 3,5-dimethylphenyl, cyclohexyl or naphth-2-yl.

Most preferably, Y is phenyl.

Preferably, Ar is phenyl optionally substituted by 1, 2 or 3 halo substituents.

More preferably, Ar is phenyl substituted by 1 or 2 chloro substituents.

Most preferably, Ar is 3,4-dichlorophenyl.

Preferred examples of compounds of the formula (I) are compounds of the formula:

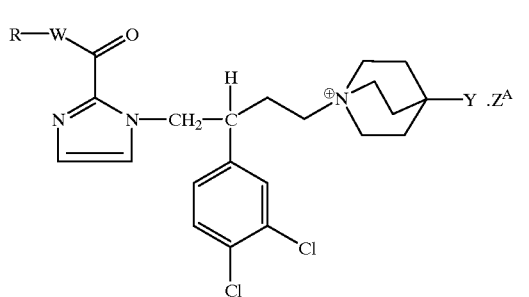

(IA)

wherein
1) R—W— is 3,5-dimethylphenyl, Y is phenyl and $Z^A$ is $CH_3SO_3^-$;
2) R—W— is 2,3-dimethylphenyl, Y is phenyl and $Z^A$ is $CH_3SO_3^-$;
3) R—W— is 2-trifluoromethoxyphenyl, Y is phenyl and $Z^A$ is $CH_3SO_3^-$;
4) R—W— is 2-methoxy-3-methylphenyl, Y is phenyl and $Z^A$ is $CH_3SO_3^-$;
5) R—W— is 2,3-dihydrobenzo[b]furan-7-yl, Y is phenyl and $Z^A$ is $CH_3SO_3^-$;
6) R—W— is naphth-2-yl, Y is phenyl and $Z^A$ is $CH_3SO_3^-$;
7) R—W— is 4-fluoro-3-trifluoromethylphenyl, Y is phenyl and $Z^A$ is $CH_3SO_3^-$;
8) R—W— is 1,2,3,4-tetrahydronaphth-5-yl, Y is phenyl and $Z^A$ is $CH_3SO_3^-$;
9) R—W— is 1,2,3,4-tetrahydronaphth-6-yl, Y is phenyl and $Z^A$ is $CH_3SO_3^-$;
10) R—W— is 5-chloro-2-methoxyphenyl, Y is phenyl and $Z^A$ is $CH_3SO_3^-$;
11) R—W— is 2-methoxyphenyl, Y is phenyl and $Z^A$ is $CH_3SO_3^-$;
12) R—W— is 2-trifluoromethylphenyl, Y is phenyl and $Z^A$ is $CH_3SO_3^-$;
13) R—W— is 2-isopropoxyphenyl, Y is phenyl and $Z^A$ is $CH_3SO_3^-$;
14) R—W— is 2-ethylphenyl, Y is phenyl and $Z^A$ is $CH_3SO_3^-$;
15) R—W— is 2-phenoxyphenyl, Y is phenyl and $Z^A$ is $CH_3SO_3^-$;
16) R—W— is benzyl, Y is phenyl and $Z^A$ is $CH_3SO_3^-$;
17) R—W— is 3,5-bis(trifluoromethyl)phenyl, Y is phenyl and $Z^A$ is $Cl^-$;
18) R—W— is 2-methoxyphenyl, Y is cyclohexyl and $Z^A$ is $CH_3SO_3^-$;
19) R—W— is 4-fluoro-3-trifluoromethylphenyl, Y is cyclohexyl and $Z^A$ is $CH_3SO_3^-$;
20) R—W— is 2-methoxyphenyl, Y is 3,5-dimethylphenyl and $Z^A$ is $CH_3SO_3^-$; or
21) R—W— is 2-methoxyphenyl, Y is naphth-2-yl and $Z^A$ is $CH_3SO_3^-$:

or an alternative pharmaceutically acceptable salt of any thereof (re $Z^A$)

Particularly preferred examples of the compounds of the formula (I) are 4-phenyl-1-(3(S)-[3,4-dichlorophenyl]-4-[2-(1,2,3,4-tetrahydro-5-naphthoyl)-imidazol-1-yl]butyl) quinuclidinium methanesulphonate and 4-phenyl-1-(3(R)-[3,4-dichlorophenyl]-4-[2-(1,2,3,4-tetrahydro-5-naphthoyl) imidazol-1-yl]butyl)quinuclidinium methanesulphonate.

All the compounds of the formula (I) can be prepared by reaction of a compound of the formula:

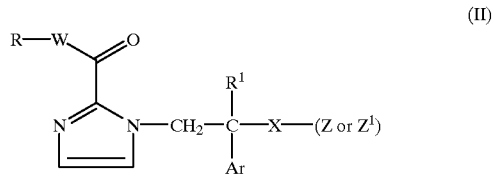

(II)

wherein R, $R^1$, Ar, W and X are as previously defined for a compound of the formula (I), Z is a suitable leaving group capable of forming a pharmaceutically acceptable anion ($Z^A$) and $Z^1$ is a suitable leaving group, with a compound of the formula:

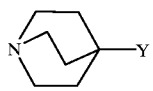
(III)

wherein Y is as previously defined for a compound of the formula (I), said process being followed by either (a), where $Z^1$ is a suitable leaving group, exchange for a pharmaceutically acceptable anion ($Z^A$), or (b), optionally, where $Z^A$ is a pharmaceutically acceptable anion, exchange for another pharmaceutically acceptable anion.

Preferred examples of Z are $C_1$–$C_4$ alkanesulphonyloxy, benzenesulphonyloxy, para-toluenesulphonyloxy, chloro, bromo and iodo.

An example of $Z^1$ is trifluoromethanesulphonyloxy.

Preferably, the leaving group in the compound of the formula (II) forms a pharmaceutically acceptable anion ($Z/Z^A$), e.g. methanesulphonyloxy/methanesulphonate, and therefore anion exchange at the end of the process is unnecessary.

It is possible to exchange pharmaceutically acceptable anions (re $Z^A$) in the work-up procedure, e.g. methanesulphonate may be exchanged to chloride by treatment of the isolated compound or the crude mixture with aqueous hydrochloric acid solution.

The reaction of the compounds (II) and (III) is generally carried out in a suitable solvent, e.g. acetonitrile, at elevated temperatures, preferably at the reflux temperature thereof.

The starting materials of the formula (II) can be prepared as shown in Scheme 1.

Scheme 1

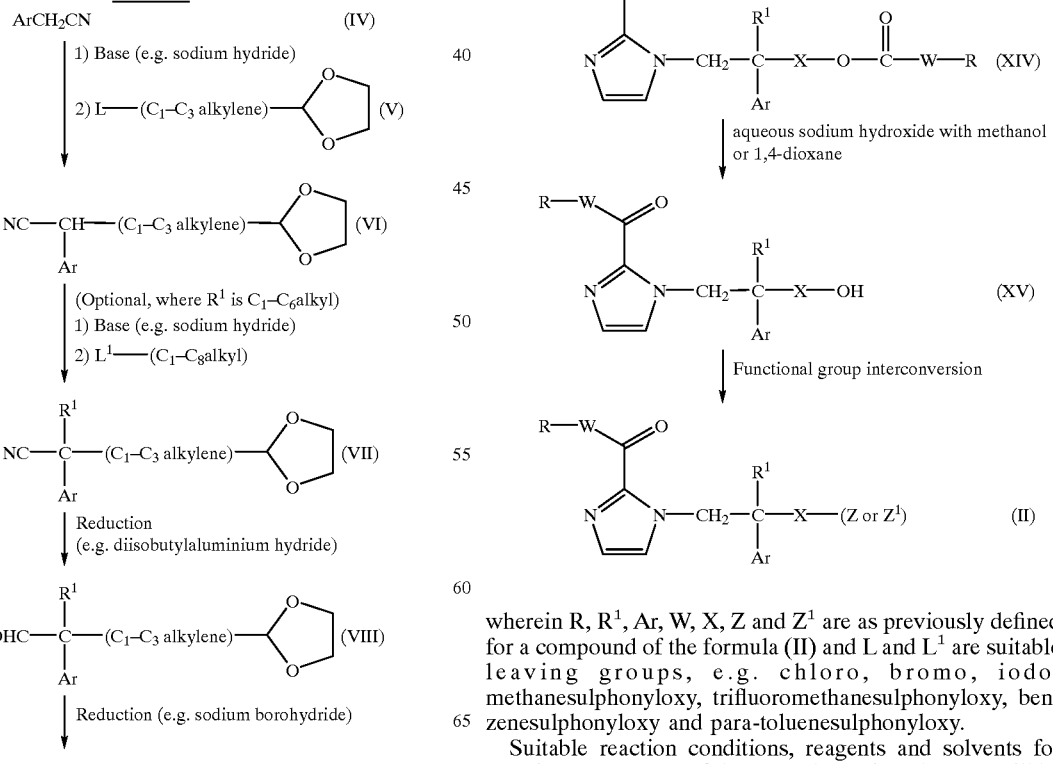

wherein R, $R^1$, Ar, W, X, Z and $Z^1$ are as previously defined for a compound of the formula (II) and L and $L^1$ are suitable leaving groups, e.g. chloro, bromo, iodo, methanesulphonyloxy, trifluoromethanesulphonyloxy, benzenesulphonyloxy and para-toluenesulphonyloxy.

Suitable reaction conditions, reagents and solvents for carrying out any one of the steps shown in Scheme 1 will be well-known to those skilled in the art with reference to the Preparations herein.

With regard to the last step in the reaction sequence, a compound of the formula (XV) can be converted to a compound of the formula (II) using conventional conditions. For example, an alcohol of the formula (XV) can be converted to a compound of the formula (II) where Z is methanesulphonyloxy by treatment with methanesulphonyl chloride, triethylamine and dichloromethane, and a compound of the formula (II) wherein $Z^1$ is trifluoromethanesulphonyloxy may be prepared by treating an alcohol of the formula (XV) with trifluoromethanesulphonic anhydride, optionally in the presence of a suitable acid acceptor, and in a suitable solvent, e.g. dichloromethane.

The compounds of the formula (XII) can also be prepared as shown in Scheme 2:

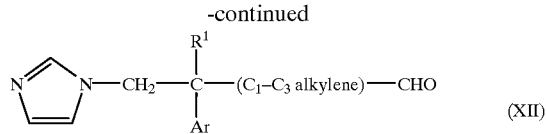

wherein $R^1$ and Ar are as previously defined for a compound of the formula (XII) and $L^2$ and $L^3$ are suitable leaving groups, e.g. as previously defined for L and $L^1$.

Suitable reaction conditions, reagents and solvents for carrying out any one of the steps shown in Scheme 2 will be well-known to those skilled in the art with reference to the Preparations herein.

The compounds of the formula (XV) can also be prepared as shown in Scheme 3:

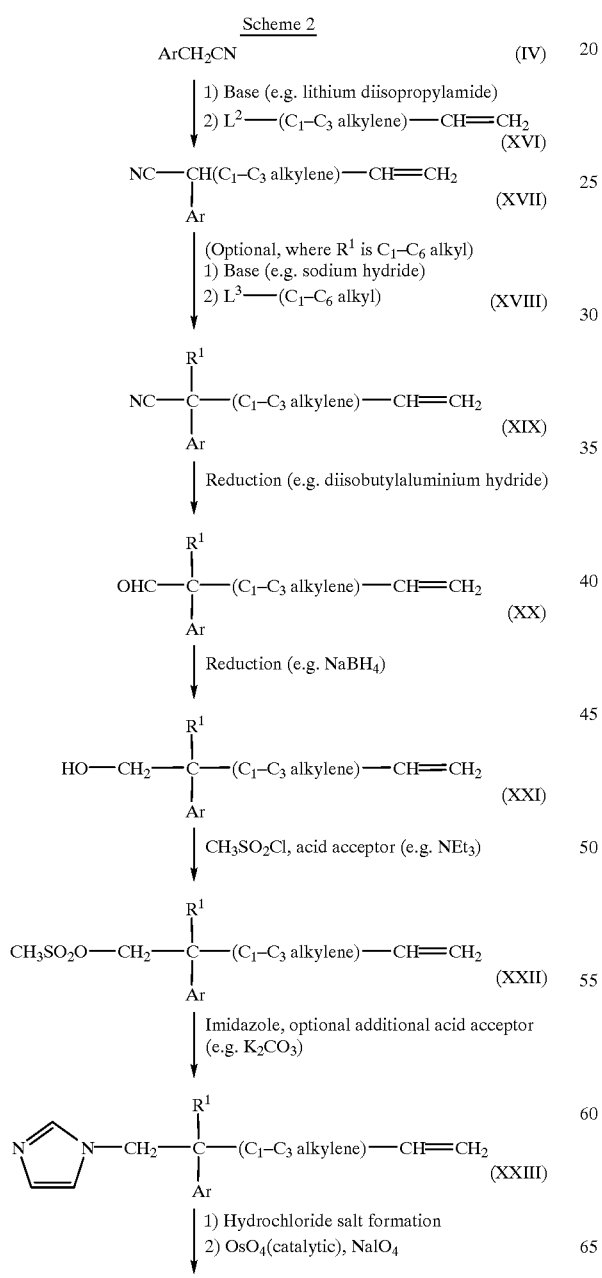

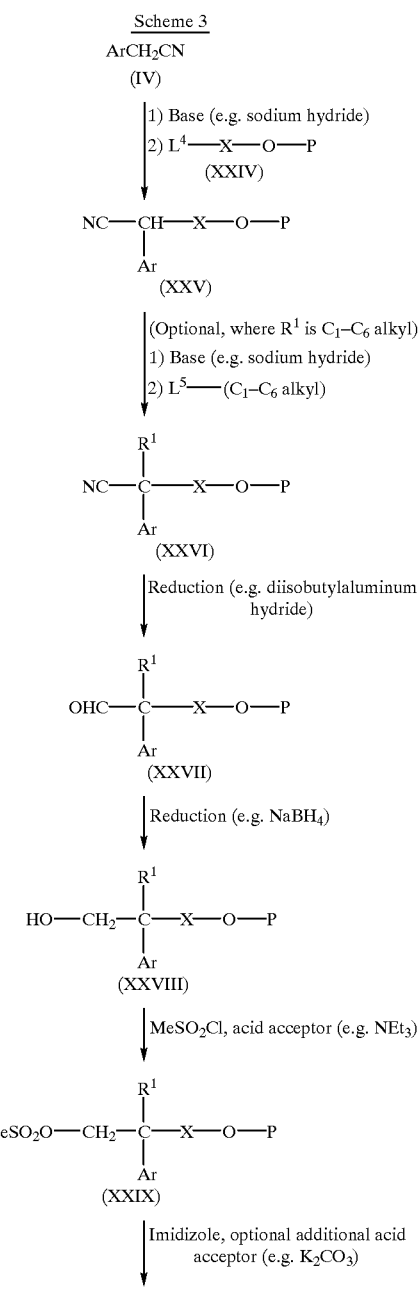

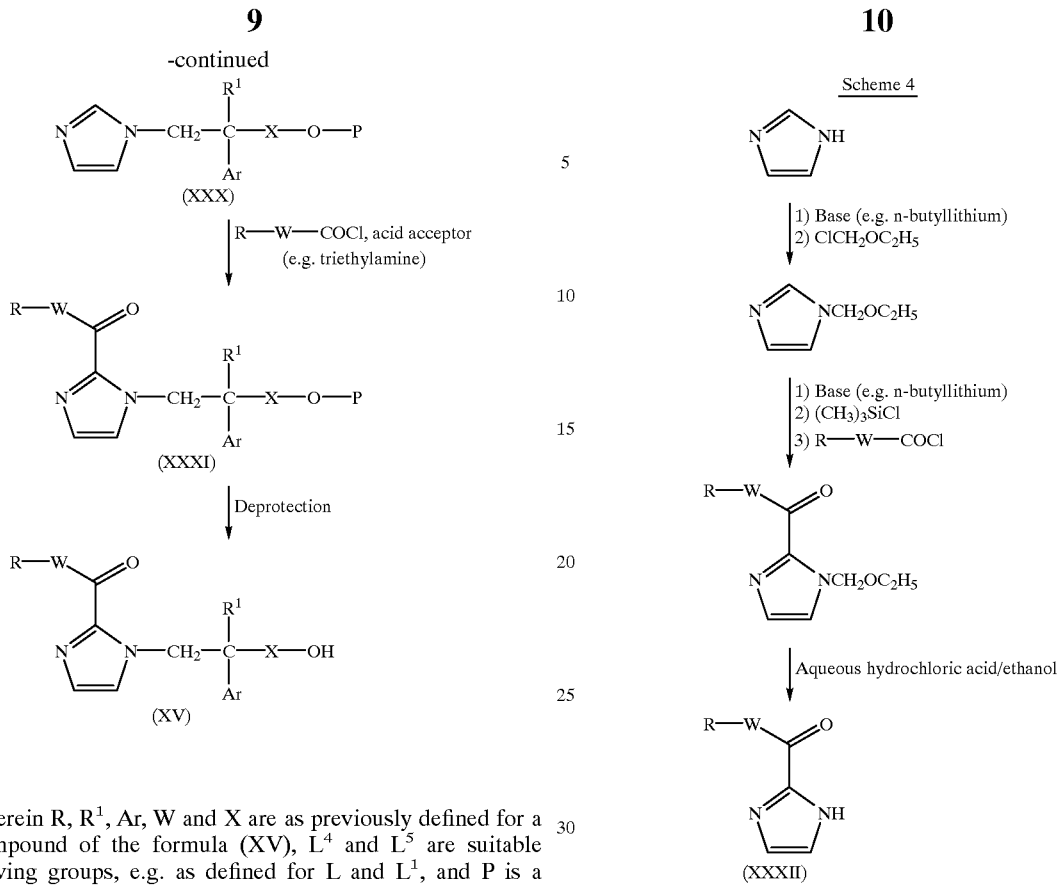

wherein R, R¹, Ar, W and X are as previously defined for a compound of the formula (XV), $L^4$ and $L^5$ are suitable leaving groups, e.g. as defined for L and $L^1$, and P is a suitable protecting group.

Examples of suitable protecting groups (P) together with methods for their removal can be found in the publication "Protective Groups in Organic Synthesis", T. W. Greene and P. G. M. Wuts, Second Edition, Wiley-Interscience. A preferred example of P is tetrahydropyran-2-yl that can be removed using Amberlyst 15 (trade mark) ion exchange resin or methanol saturated with hydrogen chloride gas.

Suitable reaction conditions, reagents and solvents for carrying out any one of the steps shown in Scheme 3 will be well known to those skilled in the art with reference to the Preparations herein.

The compounds of the formula (XXXI) can also be prepared by reacting a compound of the formula (XXIX) with a compound of the formula:

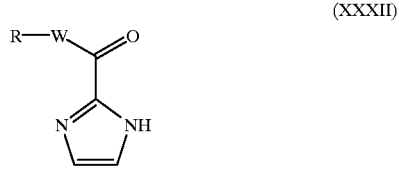

wherein R and W are as previously defined for a compound of the formula (XXXI), optionally in the presence of an additional acid acceptor, e.g. potassium carbonate.

The compounds of the formula (XXXII) may be prepared as shown in Scheme 4.

wherein R and W are as previously defined for a compound of the formula (XXXII).

The compounds of the formula (III) can be prepared by a similar method to that described in Chem.Ber., 108, 3475 (1975).

Alternatively, the compounds of the formula (III) where Y is cyclohexyl optionally substituted as previously defined for the definition of Y for a compound of the formula (I) can be prepared by catalytic hydrogenation of a compound of the formula:

wherein Y is phenyl optionally substituted as previously defined for the above definition of Y. The reduction can be carried out under a hydrogen atmosphere using a suitable catalyst, e.g. rhodium-on-alumina, and in a suitable solvent, e.g. acetic acid.

The compounds of the formula (IIIA) may be prepared by similar methods to those described in Chem.Ber., 108, 3475 (1975) and J.Org.Chem., 22, 1484 (1957).

The compounds of the formula (III) can also be prepared as shown in Scheme 5:

Scheme 5

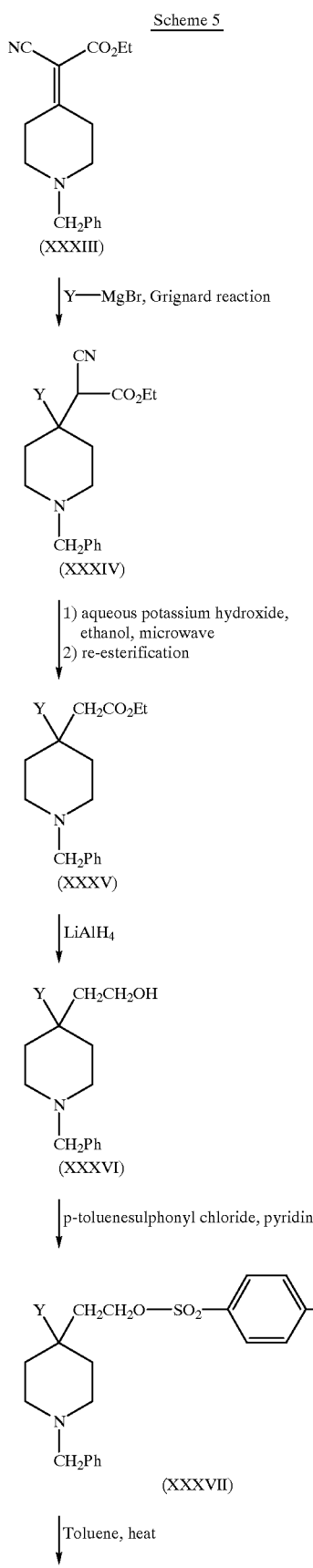

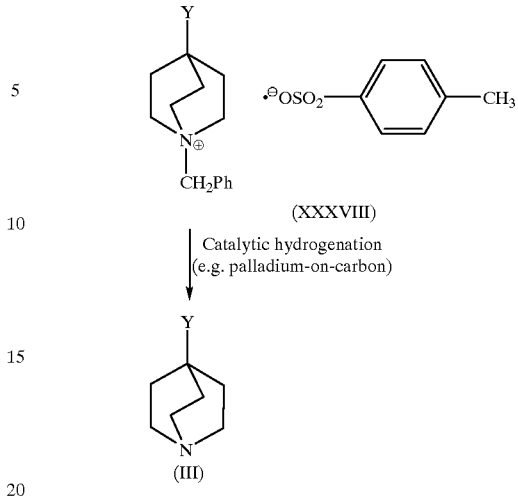

wherein Y is as previously defined for a compound of the formula (III).

Suitable reaction conditions, reagents and solvents for carrying out any one of the steps shown in Scheme 5 will be well-known to those skilled in the art with reference to the Preparations herein.

All of the above reactions and the preparations of novel starting materials used in the preceding methods are conventional and appropriate reagents and reaction conditions for their performance or preparation as well as procedures for isolating the desired products will be well known to those skilled in the art with reference to literature precedents and the Examples and Preparations hereto.

The affinity of the compounds of the formula (I) for the human $NK_1$ receptor can be determined in vitro by determining their ability to inhibit [$^3$H]-Substance P binding to membranes prepared from the human IM9 cell line expressing the human $NK_1$ receptor using a modification of the method described in McLean, S. et al, J. Pharm.Exp.Ther., 267, 472–9 (1993) in which whole cells were used.

The affinity of the compounds of formula (I) for the human $NK_2$ receptor can be determined in vitro by determining their ability to compete with [$^3$H]-NKA (neurokinin A) for binding to membranes prepared from Chinese hamster ovary cells expressing the cloned human $NK_2$ receptor. In this method, washed Chinese hamster ovary cell membranes are prepared as described for the previous method where IM9 cells are used instead. The membranes are incubated (90 min, 25° C.) with [$^3$H]-NKA and with a range of concentrations of the test compound. Non-specific binding is determined in the presence of 10 $\mu$M NKA.

The $NK_1$ receptor antagonist activity of the compounds of the formula (I) can be determined in Am by testing their ability to antagonise the contractile effects of Substance P in de-epithelialised guinea pig tracheal strips. Tissues can be prepared from guinea pigs (350–600 g) which are killed by stunning and exsanguination. The excised trachea is cleared of connective tissue and opened longitudinally, opposite the trachealis muscle band. The epithelial layer can then be removed by rubbing the inner surface of the trachea with a cotton bud. Strips of approximately 4 cartilage bands wide are cut and mounted under 1 g tension in organ baths containing Krebs solution (composition: NaCl 118 mM, KCl 4.6 mM, NaHCO$_3$ 25 mM, KH$_2$PO$_4$ 1.4 mM, MgSO$_4$ 1.2 mM, CaCl$_2$ 2.5 mM, glucose 11 mM) at 37° C. and gassed with 95% O$_2$/5% CO$_2$. The potential action of Substance P on the $NK_2$ receptor population found in this tissue can be prevented by the inclusion of the selective $NK_2$ receptor antagonist ±SR-48,968 (1 μM) in the Krebs buffer solution. Additionally, indomethacin (3 μM) is added to remove the influence of endogenous prostanoids. Tension changes of the tissue in response to cumulative addition of the agonist Substance P are recorded isometrically. The potency of the compounds of the formula (I) can be assessed by the magnitude of shift induced in the Substance P dose response curve, using standard Schild analysis, following 30 minutes incubation of the compound with the tissue.

The de-epithelialised guinea pig trachea strip preparation may also be used to evaluate the $NK_2$ receptor antagonist activity of the compounds of the formula (I) in vitro by using the selective $NK_2$ receptor agonist [β-Ala$^8$]NKA$_{(4-10)}$ as the contractile agent. For such studies, strips are prepared and mounted in organ baths as described above, using Krebs solution of the following composition: NaCl 118 mM, KCl 4.6 mM, NaHCO$_3$ 25 mM, KH$_2$PO$_4$ 1.4 mM, MgSO$_4$ 1.2 mM, CaCl$_2$ 2.5 mM, glucose 11 mM, indomethacin 3 μM. The potency of the compounds may be assessed by the magnitude of the shift induced in the [β-Ala$^8$]NKA$_{(4-10)}$ dose response curve, using standard Schild analysis, following 30 minutes incubation of the compound with the tissue.

The compounds of the formula (I) can be tested for $NK_3$ receptor antagonist activity, in vitro, by testing their ability to antagonise the contractile effects of the selective $NK_3$ receptor agonist senktide in the guinea-pig ileum using the method of Maggi et al, Br.J.Pharmacol., 101, 996–1000 (1990).

For human use, the compounds of the formula (I) can be administered alone, but will generally be administered in admixture with a pharmaceutical carrier selected with regard to the intended route of administration and standard pharmaceutical practice.

For example, they can be administered orally or sublingually in the form of tablets containing such excipients as starch or lactose, or in capsules or ovules either alone or in admixture with excipients, or in the form of elixirs, solutions or suspensions containing flavouring or colouring agents.

They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the compounds of the formula (I) will be from 0.01 to 20 mg/kg (in single or divided doses).

Thus tablets or capsules of the compounds will contain from 1 mg to 1.0 g of active compound for administration singly or two or more at a time, as appropriate. The physician in any event will determine the actual dosage which will be most suitable for an individual patient and it will vary with the age, weight and response of the particular patient. The above dosages are exemplary of the average case. There can, of course, be individual instances where higher or lower dosage ranges are merited and such are within the scope of this invention.

The compounds of formula (I) can also be administered intranasally or by inhalation and are conveniently delivered in the form of a dry powder inhaler or an aerosol spray presentation from a pressurised container or a nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the formula (I) and a suitable powder base such as lactose or starch.

Aerosol formulations are preferably arranged so that each metered dose or "puff" of aerosol contains from 20 μg to 1000 μg of a compound of formula (I) for delivery to the patient. The overall daily dose with an aerosol will be in the range of from 20 μg to 20 mg which may be administered in a single dose or, more usually, in divided doses throughout the day.

Alternatively, the compounds of the formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin, or they can be incorporated, at a concentration of from 1 to 10% by weight, into an ointment consisting of a white wax or white soft paraffin base together with such stabilisers and preservatives as may be required. The compounds of the formula (I) may also be transdermally administered by the use of a skin patch.

It is to be appreciated that reference to treatment includes curative, palliative or prophylactic treatment.

Thus the invention further provides:

(i) a pharmaceutical composition comprising a compound of the formula (I) together with a pharmaceutically acceptable diluent or carrier;

(ii) a compound of the formula (I) or a pharmaceutically acceptable composition thereof, for use as a medicament;

(iii) the use of a compound of the formula (I), or of a pharmaceutically acceptable composition thereof, for the manufacture of a medicament for the treatment of a disease by producing an antagonist effect on a tachykinin receptor or on a combination of tachykinin receptors;

(iv) use as in (iii) where the antagonist effect is on the human $NK_1$ and $NK_2$ tachykinin receptors;

(v) use as in (iii) or (iv) where the disease is an inflammatory disease such as arthritis, psoriasis, asthma or inflammatory bowel disease, a central nervous system (CNS) disorder such as anxiety, depression, dementia or psychosis, a gastrointestinal (GI) disorder such as functional bowel disease, irritable bowel syndrome, gastro-oesophageal reflux, faecal incontinence, colitis or Crohn's disease, a disease caused by *Helicobacter pylori* or another urease-positive Gram negative bacteria, a urogenital tract disorder such as incontinence, hyperreflexia or cystitis, a pulmonary disorder such as chronic obstructive airways disease, an allergy such as eczema, contact dermatitis, atopic dermatitis or rhinitis, a hypersensitivity disorder such as to poison ivy, a peripheral neuropathy such as diabetic neuropathy, neuralgia, causalgia, painful neuropathy, a burn, herpetic neuralgia or post-herpetic neuralgia, emesis, cough, migraine or acute or chronic pain;

(vi) a method of treatment of a human to treat a disease by producing an antagonist effect on a tachykinin receptor or on a combination of tachykinin receptors, which comprises treating said human with an effective amount of a compound of the formula (I) or with a pharmaceutically acceptable composition thereof;

(vii) a method as in (vi) where the antagonist effect is on the human $NK_1$ and $NK_2$ tachykinin receptors;

(viii) a method as in (vi) or (vii) where the disease is an inflammatory disease such as arthritis, psoriasis, asthma or inflammatory bowel disease, a central nervous system (CNS) disorder such as anxiety, depression, dementia or psychosis, a gastro-intestinal (GI) disorder such as functional bowel disease, irritable bowel syndrome, gastro-oesophageal reflux, faecal incontinence, colitis or Crohn's disease, a disease caused by *Helicobacter pylori* or another urease-positive Gram negative bacteria, a urogenital tract disorder such as incontinence, hyperreflexia or cystitis, a pulmonary disorder such as chronic obstructive airways disease, an allergy such as eczema, contact dermatitis, atopic dermatitis or rhinitis, a hypersensitivity disorder such as to poison ivy, a peripheral neuropathy such as diabetic neuropathy, neuralgia, causalgia, painful neuropathy, a burn, herpetic neuralgia or post-herpetic neuralgia, emesis, cough, migraine or acute or chronic pain; and (ix) a compound of the formula (II), (XI), (XII), (XIII), (XIV), (XV), (XXIII), (XXX) or (XXXI)

with the proviso that for a compound of the formula (XXIII), when $R^1$ is H and "$C_1$–$C_3$ alkylene" is $CH_2$, then Ar is not 2-chlorophenyl or 2,4-dichlorophenyl.

The following Examples illustrate the preparation of the compounds of the formula (I):

EXAMPLE 1

4-Phenyl-1-(3-[3,4-dichlorophenl]-4-[2-(3,5-dimethylbenzoyl)imidazol-1-yl]butyl)quinuclidinium methanesulphonate

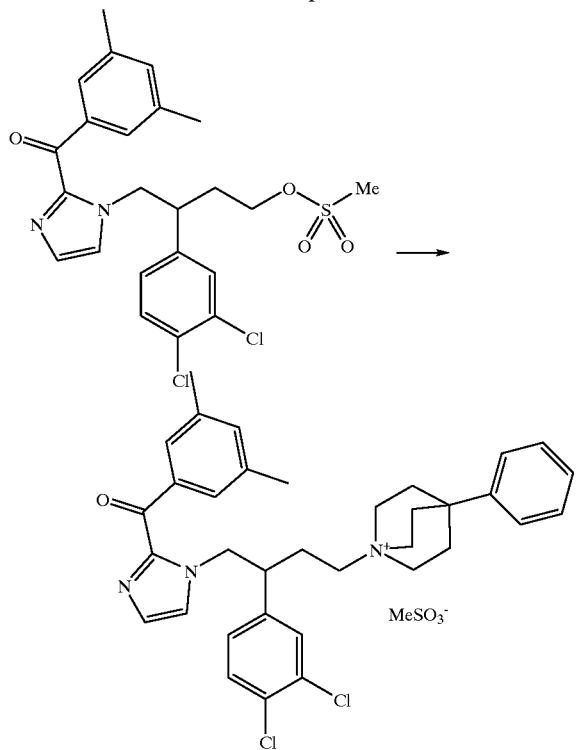

1-Methanesulphonyloxy-3-(3,4-dichlorophenyl)-4-[2-(3,5-dimethylbenzoyl)imidazol-1-yl]-butane (0.71 g) (see Preparation 74) and 4-phenylquinuclidine (0.32 g) (see J. Org. Chem., 22, 1484, (1957)) were dissolved in acetonitrile (10 ml) and the mixture heated under reflux for 4 hours. The solvent was removed under reduced pressure and the resulting residue dissolved in dichloromethane before removal of the solvent under reduced pressure. The residue was chromatographed on silica gel eluting with a solvent gradient of 95:5 changing to 85:15, by volume, dichloromethane:methanol to give the product as a white foam. This was then triturated with diethyl ether, filtered and dried at room temperature under reduced pressure to give 4-phenyl-1-(3-[3,4-dichlorophenyl]-4-[2-(3,5-dimethylbenzoyl)imidazol-1-yl]butyl)quinuclidinium methanesulphonate (0.71 g) as a white solid.

hu 1H-NMR (CDCl$_3$): δ=7.62 (2H, s), 7.16–7.41 (10H, m), 7.11 (1H, s), 4.66–4,86 (2H, m), 3.52–3.81 (7H, m), 3.32–3.47 (1H, m), 2.91–3.08 (1H, m), 2.82 (3H, s), 2.22–2.50 (14H, m) ppm.

Found: C, 61.53; H, 6.17; N, 6.03. $C_{36}H_{41}Cl_2N_3O_4S$ requires C, 61.70; H, 6.18; N, 5.99%.

EXAMPLES 2–16

The compounds of the following tabulated Examples (Table 1) of the general formula:

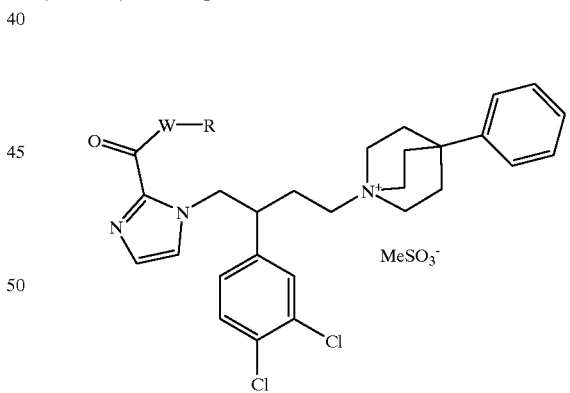

were prepared by a similar method to that of Example 1 using the appropriate mesylate (see Preparations 75–84 and 86–90) and 4-phenylquinuclidine as the starting materials.

TABLE 1

| Example no. | Starting material Prep. no. | R—W— | Analytical Data |
|---|---|---|---|
| 2 | 75 | 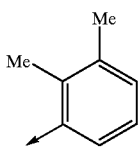 | ¹H-NMR(CDCl₃): δ=7.03–7.41(13H, m), 4.80–4.97(2H, m), 3.59–3.84(7H, m), 3.38–3.50(1H, m), 2.97–3.10(1H, m), 2.84(3H, s), 2.40–2.59(2H, m), 2.23–2.34(9H, m), 2.09(3H, s) ppm. Found: C, 61.70; H, 6.01; N, 6.00. $C_{36}H_{41}Cl_2N_3O_4S$. 1.00 mol $H_2O$ requires C, 61.70; H, 6.18; N, 6.00%. |
| 3 | 76 | 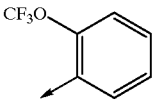 | ¹H-NMR(CDCl₃): δ=7.21–7.59(13H, m), 7.11(1H, s), 4.89(1H, dd), 4.75 (1H, dd), 3.55–3.85(7H, m), 3.30–3.42 (1H, m), 2.99–3.11(1H, m), 2.84(3H, s), 2.21–2.62(8H, m)ppm. Found: C, 55.35; H, 4.86; N, 5.48. $C_{35}H_{36}Cl_2F_3N_3O_5S$. 0.4 mol $CH_2Cl_2$ requires C, 55.03; H, 4.93; N, 5.43%. |
| 4 | 77 | 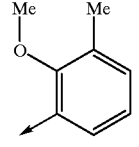 | ¹H-NMR(CDCl₃): δ=7.21–7.46(10H, m), 7.01–7.16(3H, m), 4.72–4.92(2H, m), 3.52–3.85(10H, m), 3.32–3.49(1H, m), 3.00–3.12(1H, m), 2.82(3H, s), 2.42–2.56(2H, m), 2.20–2.38(9H, m) ppm. Found: C, 59.25; H, 5.86; N, 5.67. $C_{36}H_{41}Cl_2N_3O_5S$. 0.5 mol $H_2O$. 0.3 mol $CH_2Cl_2$ requires C, 59.29; H,5.84; N, 5.71%. |
| 5 | 78 | 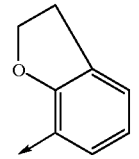 | ¹H-NMR(CDCl₃): δ=7.60(1H, d), 7.21–7.42(10H, m), 7.09(1H, s), 6.89 (1H, t), 4.82(1H, dd), 4.57–4.71(3H, m), 3.58–3.84(7H, m), 3.41–3.52(1H, m), 3.22(2H, t), 3.02–3.14(1H, m), 2.81 (3H, s), 2.20–2.55(8H, m)ppm. Found: C, 60.32; H, 5.66; N, 5.88. $C_{36}H_{39}Cl_2N_3O_5S$. 0.3 mol $CH_2Cl_2$ requires C,60.38; H, 5.53; N, 5.82%. |
| 6 | 79 | 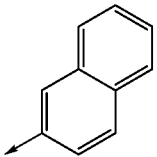 | ¹H-NMR(CDCl₃): δ=8.79(1H, s), 8.11(1H, d), 8.00(1H, d), 7.89(2H, t), 7.51–7.64(2H, m), 7.48(1H, s), 7.19–7.40(9H, m), 4.71–4.90(2H, m), 3.59–3.80(7H, m), 3.03–3.51(1H, m), 2.99–3.09(1H, m), 2.88(3H, s), 2.42–2.55 (2H, m), 2.22–2.38(6H, m)ppm. Found: C, 64.08; H, 5.68; N, 5.90. $C_{38}H_{39}Cl_2N_3O_4S$ 0.5 mol $H_2O$ requires C, 63.95; H, 5.65; N, 5.89%. |
| 7 | 80 | 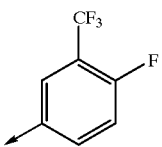 | ¹H-NMR(CDCl₃): δ=8.41–8.52(2H, m), 7.51(1H, s), 7.11–7.42(10H, m), 4.72–4.89(2H, m), 3.60–3.89(7H, m), 3.31–3.46(1H, m), 2.97–3.09(1H, m), 2.85(3H, s), 2.42–2.59(2H, m), 2.21–2.39(6H, m)ppm. Found: C, 56.15; H, 4.88; N, 5.77. $C_{35}H_{35}Cl_2F_4N_3O_4S$. 0.5 mol $H_2O$ requires C, 56.08;H, 4.84; N, 5.61%. |
| 8 | 81 | 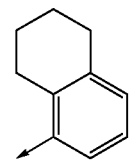 | ¹H-NMR(CDCl₃): δ=7.05–7.44(13H, m), 4.80–4.94(2H, m), 3.61–3.89(7H, m), 3.38–3.71(1H, m), 3.01–3.12(1H, m), 2.76–2.91(5H, m), 2.22–2.69(10H, m), 1.63–1.86(4H, m)ppm. Found: C, 64.11; H, 6.30; N, 6.00. $C_{38}H_{43}Cl_2N_3O_4S$ requires C, 64.60; H, 6.12; N, 5.93%. |

TABLE 1-continued

| Example no. | Starting material Prep. no. | R—W— | Analytical Data |
|---|---|---|---|
| 9 | 82 | tetrahydronaphthalen-2-yl | $^1$H-NMR(CDCl$_3$): δ=7.78–7.86(2H, m), 7.21–7.40(9H, m), 7.11–7.16(2H, m), 4.80(1H, dd), 4.68(1H, dd), 3.60–3.85(7H, m), 3.37–3.49(1H, m), 3.02–3.11(1H, m), 2.79–2.90(7H, m), 2.40–2.51(2H, m), 2.22–2.36(6H, m), 1.82 (4H, br. s)ppm.<br>Found: C, 63.90; H, 625; N, 6.05.<br>C$_{38}$H$_{43}$Cl$_2$N$_3$O$_4$S. 0.25 mol H$_2$O requires C, 63.99; H, 6.15; N, 5.89%. |
| 10 | 83 | 4-methoxy-3-chlorophenyl (Me-O, Cl substituents) | $^1$H-NMR(CDCl$_3$): δ=7.24–7.46(11H, m), 7.08(1H, s), 6.91(1H, d), 4.89(1H, dd), 4.72(1H, dd), 3.64–3.88(10H, m), 3.15–3.46(1H, m), 3.07–3.17(1H, m), 2.88 (3H, s), 2.46–2.56(2H, m), 2.26–2.40(6H, m)ppm. |
| 11 | 84 | 2-methoxyphenyl | $^1$H-NMR(CDCl$_3$): δ=6.94–7.49(14H, m), 4.90(1H, dd), 4.70(1H, dd), 3.61–3.84(10H, m), 3.36–3.49(1H, m), 3.09–3.20(1H, m), 2.82(3H, s), 2.22–2.59 (8H, m)ppm.<br>Found: C, 58.80; H, 5.68; N, 5.88.<br>C$_{35}$H$_{39}$Cl$_2$N$_3$O$_5$S. 0.5 mol H$_2$O requires C, 58.87; H, 5.38; N, 6.06%. |
| 12 | 86 | 2-trifluoromethylphenyl | $^1$H-NMR(CDCl$_3$): δ=7.72(1H, d), 7.55–7.66(2H, m), 7.20–7.49(10H, m), 7.09(1H, s), 4.94(1H, dd), 4.72(1H, dd), 3.60–3.85(7H, m), 3.30–3.42(1H, m), 3.05–3.18(1H, m), 2.86(3H, s), 2.36–2.59(2H, m), 2.21–2.32(6H, m) ppm.<br>Found: C, 57.41; H, 5.13; N, 5.79<br>C$_{35}$H$_{36}$Cl$_2$F$_3$N$_3$O$_4$S. 0.5 mol H$_2$O requires C, 57.46; H, 5.10; N, 5.74%. |
| 13 | 87 | 2-isopropoxyphenyl | $^1$H-NMR(CDCl$_3$): δ=7.20–7.46(10H, m), 6.91–7.10(4H, m), 4.83(1H, dd), 4.43–4.68(2H, m), 3.66–3.90(7H, m), 3.32–3.48(1H, m), 3.15–3.31(1H, m), 2.42–2.58(2H, m), 2.22–2.36(6H, m), 1.11–1.21(6H, m)ppm.<br>Found: C, 61.88; H, 5.97; N, 6.11.<br>C$_{37}$H$_{43}$Cl$_2$N$_3$O$_5$S. 0.25 mol H$_2$O requires C, 61.96; H, 6.11; N, 5.86%. |
| 14 | 88 | 2-ethylphenyl | $^1$H-NMR(CDCl$_3$): δ= 7.15–7.41(13H, m), 7.06(1H, s), 4.80–4.91(2H, m), 3.59–3.86(7H, m), 3.34–3.49(1H, m), 3.00–3.12(1H, m), 2.83(3H, s), 2.40–2.66(4H, m), 2.21–2.35(6H, m), 1.15 (3H, t)ppm.<br>Found: C, 62.45; H, 6.11; N, 6.13.<br>C$_{36}$H$_{41}$Cl$_2$N$_3$O$_4$S. 0.2 mol CH$_2$Cl$_2$ requires C, 62.14; H, 5.96; N, 6.01%. |
| 15 | 89 | 2-phenoxyphenyl | $^1$H-NMR(CDCl$_3$): δ=6.83–7.53(19H, m), 4.79(1H, dd), 4.55(1H, dd), 3.43–3.72(7H, m), 3.03–3.30(2H, m), 2.81 (3H, s), 2.09–2.49(8H, m)ppm.<br>Found: C, 63.02; H, 5.55; N, 5.72.<br>C$_{40}$H$_{41}$Cl$_2$N$_3$O$_5$S. 0.25 mol CH$_2$Cl$_2$ requires C, 62.95; H, 5.45; N, 5.47%. |

TABLE 1-continued

| Example no. | Starting material Prep. no. | R—W— | Analytical Data |
|---|---|---|---|
| 16 | 90 | 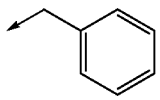 | $^1$H-NMR(CDCl$_3$): δ=7.08–7.40(15H, m), 4.74(1H, dd), 4.61(1H, dd), 4.46 (1H, d), 4.29(1H, d), 3.48–3.71(7H, m), 3.14–3.28(1H, m), 2.88–3.04(1H, m), 2.79(3H, s), 2.15–2.39(8H, m)ppm. Found: C, 61.41; H, 5.68; N, 6.19. C$_{35}$H$_{39}$Cl$_2$N$_3$O$_4$S. 0.2 mol CH$_2$Cl$_2$ requires C, 61.66; H, 5.79; N, 6.13%. |

EXAMPLE 17

4-Phenyl-1-(3-[3,4-dichlorophenyl]-4-{2-[3,5-bis(trifluoromethyl)benzoyl]imidazol-1-yl}butyl) quinuclidinium chloride

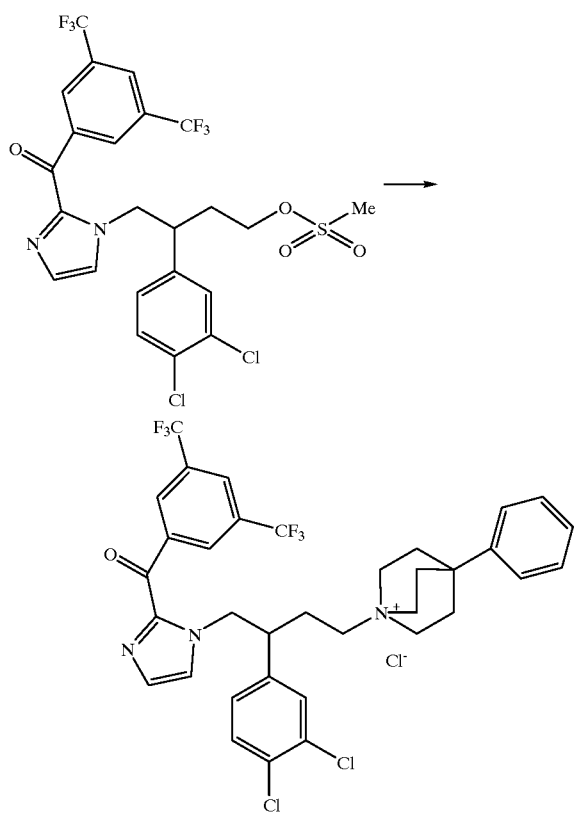

1-Methanesulphonyloxy-3-(3,4-dichlorophenyl)-4-{2-[3,5-bis(trifluoromethyl)benzoyl]imidazol-1-yl}butane (0.7 g) (see Preparation 85) and 4-phenylquinuclidine (0.32 g) (see J. Org. Chem., 22, 1484,(1957)) were dissolved in acetonitrile (10 ml) and the mixture heated under reflux for 18 hours. The solvent was removed under reduced pressure and the resulting residue dissolved in dichloromethane and washed twice with 2N aqueous hydrochloric acid solution. The organic phase was then dried over anhydrous sodium sulphate and the solvent removed under reduced pressure to give a residue which was chromatographed on silica gel eluting with a solvent gradient of 95:5 changing to 90:10, by volume, dichloromethane:methanol to give 4-phenyl-1-(3-[3,4-dichlorophenyl]-4-{2-[3,5-bis(trifluoromethyl) benzoyl]imidazol-1-yl}butyl)quinuclidinium chloride (0.37 g) as a white foam.

$^1$H-NMR (CDCl$_3$): δ=8.69 (2H, s), 8.04 (1H, s), 7.54 (1H, s), 7.14–7.41 (9H, m), 4.76–4.96 (2H, m), 3.70–3.98 (7H, m), 3.80–3.93 (1H, m), 3.10–3.21 (1H, m), 2.49–2.62 (2H, m), 2.23–2.40 (6H, m) ppm.

Found: C, 56.34; H, 4.53; N, 5.55. C$_{35}$H$_{32}$Cl$_3$F$_6$N$_3$O. 1.00 mol H$_2$O requires C, 56.12; H, 4.58; N, 5.61%.

EXAMPLE 18

4-Phenyl-1-(3(S)-[3,4-dichlorophenyl]-4-[2-(1,2,3,4-tetrahydro-5-naphthoyl)imidazol-1-yl]butyl) quinuclidinium methanesulphonate

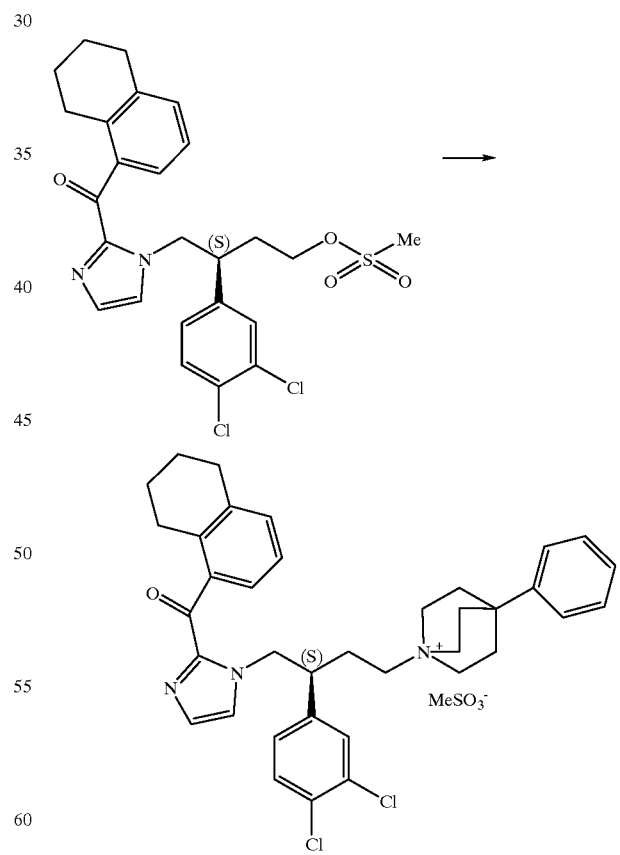

1-Methanesulphonyloxy-3(S)-(3,4-dichlorophenyl)-4-[2-(1,2,3,4-tetrahydro-5-naphthoyl)imidazol-1-yl]butane (0.82 g) (see Preparation 105) and 4-phenylquinuclidine (0.35 g) (see J. Org. Chem., 22, 1484, (1957)) were dissolved in acetonitrile (10 ml) and the mixture heated under reflux for 4 hours and then left to stand at room temperature overnight. The solvent was removed under reduced pressure and the residue chromatographed on silica gel eluting with a solvent gradient of 9:1 changing to 8:2, by volume, dichloromeane:methanol to give the product as a white foam. This was dissolved in dichloromethane, filtered and the solvent removed from the filtrate to give 4-phenyl-1-(3(S)-[3,4-dichlorophenyl]-4-[2-(1,2,3,4-tetrahydro-5-naphthoyl)imidazol-1-yl]butyl)quinuclidinium methanesulphonate (0.7 g) as a white powder.

$^1$H-NMR (CDCl$_3$): δ=7.05–7.44 (13H, m), 4.80–4.94 (2H, m), 3.61–3.89 (7H, m), 3.38–3.71 (1H, m), 3.01–3.12 (1H, m), 2.76–2.91 (5H, m), 2.22–2.69 (10H, m), 1.63–1.86 (4H, m) ppm.

Found: C, 63.81; H, 6.20; N, 5.99. C$_{38}$H$_{43}$Cl$_2$N$_3$O$_4$ requires C, 64.40; H, 6.12; N, 5.93%.

EXAMPLE 19

4-Phenyl-1-(3(R)-[3,4-dichlorophenyl]-4-[2-(1,2,3,4-tetrahydro-5-naphthoyl)imidazol-1-yl]butyl)quinuclidinium methanesulphonate

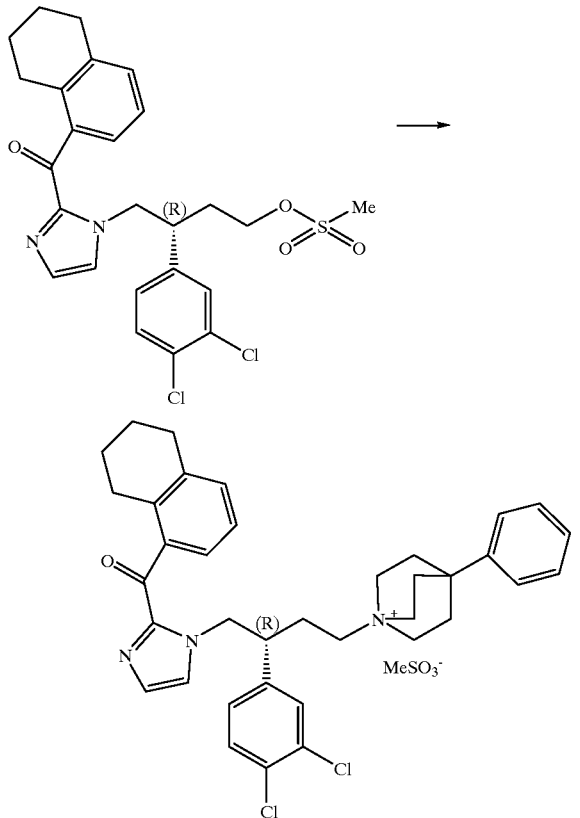

This compound was prepared in an analogous fashion to Example 18 using 1-methanesulphonyloxy-3(R)-(3,4-dichlorophenyl)-4-[2-(1,2,3,4-tetrahydro-5-naphthoyl)imidazol-1-yl]butane (see Preparation 106) and 4-phenylquinuclidine (0.36 g) (see J. Org. Chem., 22, 1484 (1957)) as the starting materials.

$^1$H-NMR (CDCl$_3$): δ=7.05–7.44 (13H, m), 4.80–4.94 (2H, m), 3.61–3.89 (7H, m), 3.38–3.71 (1H, m), 3.01–3.12 (1H, m), 2.76–2.91 (5H, m), 2.22–2.69 (10H, m), 1.63–1.86 (4H, m) ppm.

Found: C, 62.69; H, 6.07; N, 5.87. C$_{38}$H$_{43}$Cl$_2$N$_3$O$_4$S. 1.00 mol H$_2$O requires C, 62.80; H, 6.25; N, 5.78%.

EXAMPLE 20

4-Cyclohexyl-1-(3-[3,4-dichlorophenyl]-4-[2-(2-methoxybenzoyl)imidazol-1-yl]butyl)quinuclidinium methanesulphonate

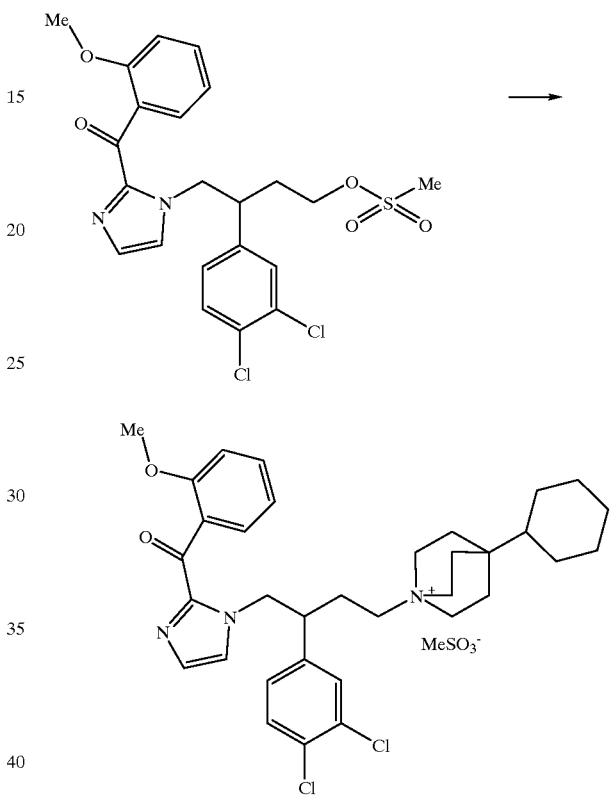

1-Methanesulphonyloxy-3-(3,4-dichlorophenyl)-4-[2-(2-methoxybenzoyl)imidazol-1-yl]butane (0.59 g) (see Preparation 84) and 4-cyclohexylquinuclidine (0.27 g) (see Preparation 1) were dissolved in acetonitrile (8 ml) and heated under reflux for 3.5 hours. The solvent was removed under reduced pressure and the resulting residue dissolved in dichloromethane and the solvent removed under reduced pressure. The residue was chromatographed on silica gel eluting with a solvent gradient of 95:5 changing to 85:15, by volume, dichloromethane:methanol to give 4-cyclohexy-1-(3-[3,4-dichlorophenyl]-4-[2-(2-methoxybenzoyl)imidazol-1-yl]butyl)quinuclidinium methanesulphonate (0.69 g) as a white foam.

$^1$H-NMR (CDCl$_3$): δ=7.21–7.49 (6H, m), 6.94–7.08 (3H, m), 4.87 (1H, dd), 4.71 (1H, dd), 3.77 (3H, s), 3.33–3.70 (8H, m), 2.91–3.06 (1H, m), 2.83 (3H, s), 2.30–2.49 (2H, m), 1.60–1.89 (11H, m), 0.80–1.28 (6H, m) ppm.

Found: C, 56.76; H, 6.31; N, 5.63. C$_{35}$H$_{45}$Cl$_2$N$_3$O$_5$S. 0.5 mol CH$_2$Cl$_2$. 0.5 mol H$_2$O requires C, 56.64; H, 6.38; N, 5.66%.

EXAMPLE 21

4-Cyclohexyl-1-(3-[3,4-dichlorophenyl]-4-[2-(3-tifluoromethyl-4-fluorobenzoyl)imidazol-1-yl]butyl) quinuclidinium methanesulphonate

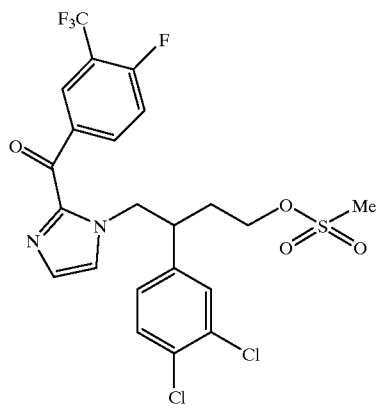

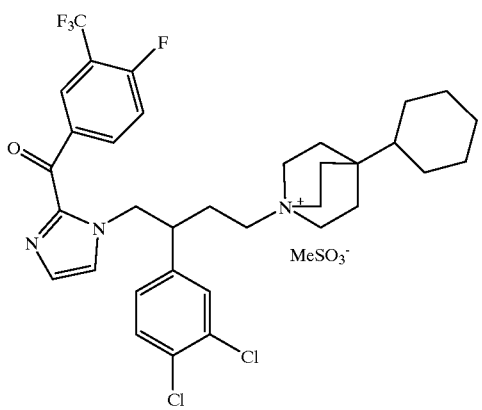

1-Methanesulphonyloxy-3-(3,4-dichlorophenyl)-4-[2-(3-trifluoromethyl-4-fluorobenzoyl)imidazol-1-yl]butane (0.77 g) (see Preparation 80) and 4-cyclohexylquinuclidine (0.31 g) (see Preparation 1) were dissolved in acetonitrile (10 ml) and heated under reflux for 5 hours. The solvent was removed under reduced pressure, the resulting residue dissolved in dichloromethane and the solvent removed under reduced pressure. The residue was chromatographed on silica gel eluting with a solvent gradient of 95:5 changing to 80:20, by volume, dichloromethane:methanol to give 4-cyclohexyl-1-(3-[3,4-dichlorophenyl]-4-[2-(3-trifluoromethyl-4-fluorobenzoyl)imidazol-1-yl]butyl)quinuclidinium methanesulphonate (0.69 g) as a white foam.

$^1$H-NMR (CDCl$_3$): δ=8.42–8.50 (2H, m), 7.55 (1H, s), 7.22–7.32 (3H, m), 7.11–7.20 (2H, m), 4.80–4.85 (2H, m), 3.34–3.76 (8H, m), 2.90–2.98 (1H, m), 2.85 (3H, s), 2.30–2.50 (2H, m), 1.75–1.81 (6H, m), 1.61–1.72 (5H, m), 1.02–1.27 (4H, m), 0.81–0.95 (2H, m) ppm.

Found: C, 56.14; H, 5.62; N, 5.70. C$_{35}$H$_{41}$Cl$_2$F$_4$N$_3$O$_4$S requires C, 56.30; H, 5.53; N, 5.63%.

EXAMPLE 22

4-(3,5-Dimethylphenyl)-1-(3-[3,4-dichlorophenyl]-4-[2-(2-methoxybenzoyl)imidazol-1-yl]butyl) quinuclidiniumn methanesulphonate

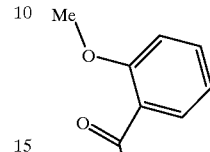

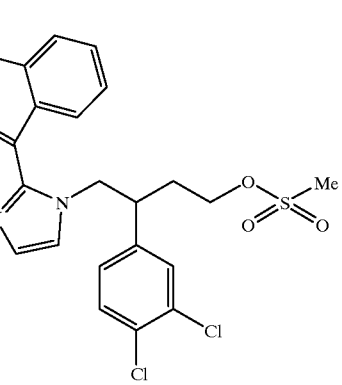

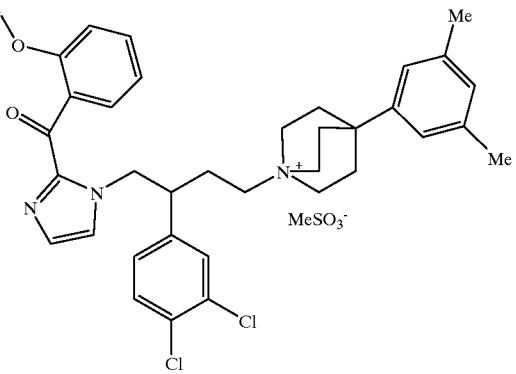

1-Methanesulphonyloxy-3-(3,4-dichlorophenyl)-4-[2-(2-methoxybenzoyl)imidazol-1-yl]butane (0.55 g) (see Preparation 84) and 4-(3,5-dimethylphenyl)quinuclidine (0.28 g) (see Preparation 12) were dissolved in acetonitrile (10 ml) and heated under reflux for 2.5 hours. The solvent was removed under reduced pressure, the resulting residue dissolved in dichloromethane and the solvent removed under reduced pressure. The residue was chromatographed on silica gel eluting with a solvent gradient of 95:5 changing to 90:10, by volume, dichloromethane:methanol to give 4-(3,5-dimethylphenyl)-1-(3-[3,4-dichlorophenyl]-4-[2-(2-methoxybenzoyl)imidazol-1-yl]butyl)quinuclidinium methanesulphonate (0.69 g) as a white foam.

$^1$H-NMR (CDCl$_3$): δ=7.28–7.48 (5H, m), 7.23 (1H, d), 6.92–7.07 (3H, m), 6.88 (1H, s), 6.82 (2H, s), 4.89 (1H, dd), 4.71 (1H, dd), 3.53–3.80 (10H, m), 3.34–3.47 (1H, m), 3.01–3.12 (1H, m), 2.82 (3H, s), 2.42–2.51 (2H, m), 2.20–2.34 (12H, m) ppm.

EXAMPLE 23

4-(2-Naphthyl)-1-(3-[3,4-dichlorophenyl]-4-[2-(2-methoxybenzoyl)imidazol-1-yl]butyl)quinuclidinium methanesulphonate

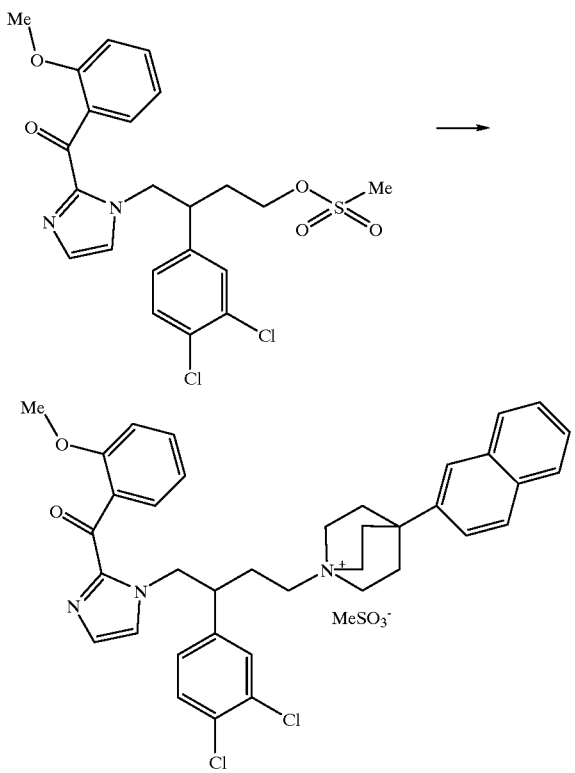

1-Methanesulphonyloxy-3-(3,4-dichlorophenyl)-4-[2-(2-methoxybenzoyl)imidazol-1-yl]butane (0.55 g) (see Preparation 84) and 4-(2-naphthyl)quinuclidine (0.31 1 g) (see Preparation 7) were dissolved in acetonitrile (10 ml) and heated under reflux for 2.5 hours. The solvent was removed under reduced pressure and the resulting residue dissolved in dichloromethane and the solvent removed under reduced pressure. The residue was chromatographed on silica gel eluting with a solvent gradient of 95:5 changing to 85:15, by volume, dichloromethane:methanol to give 4-(2-naphthyl)-1-(3-[3,4-dichlorophenyl]-4-[2-(2-methoxybenzoyl)imidazol-1-yl]butyl)quinuclidinium methanesulphonate (0.65 g) as a white foam.

$^1$H-NMR (CDCl$_3$): δ=7.71–7.86 (3H, m), 7.62 (1H, s), 7.23–7.51 (8H, m), 7.17 (1H, s), 6.92–7.07 (3H, m), 4.89 (1H, dd), 4.70 (1H, dd), 3.61–3.86 (10H, m), 3.34–3.66 (1H, m), 3.03–3.16 (1H, m), 2.84 (3H, s), 2.30–2.55 (8H, m) ppm.

The following Preparations describe the preparation of certain starting materials used in the syntheses of the compounds of the preceding Examples.

PREPARATION 1

4-Cyclohexylquinuclidine

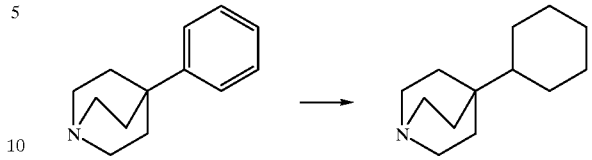

4-Phenylquinuclidine (5 g) (see J. Org. Chem., 22, 1484, (1957)) was dissolved in glacial acetic acid (25 ml), 5% w/w rhodium-on-alumina (2 g) was added and the mixture hydrogenated for 5 days at 345 kPa (50 psi). The mixture was filtered through a short column of Arbacel (trade mark) filter aid and the pad washed with methanol. The filtrate was collected and the solvent removed under reduced pressure to give a residue which was dissolved in water. The pH was adjusted to >10 by addition of 0.88 aqueous ammonia solution. The aqueous mixture was extracted with ethyl acetate (×3) and the organic layers combined, washed with brine, dried over anhydrous sodium sulphate and the solvent removed under reduced pressure to give 4-cyclohexylquinuclidine (4.7 g) as a pale pink solid.

$^1$H-NMR (CDCl$_3$): δ=2.75–2.96 (6H, m), 1.60–1.85 (5H, m), 1.06–1.45 (9H, m), 1.80–1.98 (3H, m) ppm.

PREPARATION 2

Ethyl 2-(1-benzylpiperidin-4-ylidene)-2-cyanoacetate

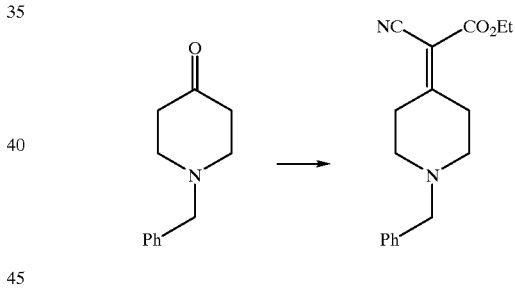

N-Benzylpiperidin-4-one (25 g), ethyl cyanoacetate (16.4 g), glacial acetic acid (6 ml) and ammonium acetate (2.54 g) were heated together in toluene (200 ml), with removal of water using a Dean and Stark apparatus, for 90 minutes. The mixture was cooled, a further amount of toluene (100 ml) added and the solution washed sequentially with water (100 ml) and brine (100 ml) at which point a red oily product precipitated. The phases were separated and the oily product dissolved in dichloromethane. The toluene and dichloromethane solutions were combined and the solvents removed under reduced pressure to give a residue. The residue was dissolved in dichloromethane and washed sequentially with water and saturated aqueous sodium hydrogen carbonate solution before removal of the solvent under reduced pressure. The crude product was chromatographed on silica gel elutiig with 98:2, by volume, dichloromethane:methanol to give the title compound (30.8 g) as an oil.

$^1$H-NMR (CDCl$_3$): δ=7.24–7.34 (5H, m), 4.22–4.32 (2H, q), 3.54 (2H, s), 3.12–3.16 (2H, m), 2.79 (2H, d), 2.66 (2H, d), 2.56 (2H, d), 1.32 (3H, t) ppm.

PREPARATION 3

Ethyl 2-cyano-2-(1-benzyl-4-(2-naphthyl)piperidin-4-yl)ethanoate

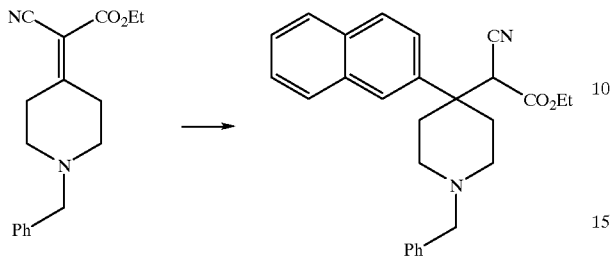

2-Bromonaphthalene (26 g) was dissolved in anhydrous diethyl ether (100 ml) and ⅕ of this solution added to a vigourously stirred mixture of magnesium turnings (3.3 g) and 2–3 iodine crystals under a nitrogen atmosphere. Gentle heating was applied to initiate formation of the Grignard reagent since it proved difficult to maintain spontaneous refluxing. The remainder of the 2-bromonaphthalene solution was added in 4 portions, allowing the refluxing to subside after each addition, and the mixture finally heated under reflux for 1 hour after which time two dark organic phases had formed. The mixture was cooled in an ice-bath and anhydrous tetrahydrofiran (50 ml) added followed by dropwise addition of a solution of ethyl 2-(1-benzylpiperidin-4-ylidene)-2-cyanoacetate (12 g) (see Preparation 2) in tetrahydrofuran (100 ml). The single phase mixture was stirred at 0° C. for 30 minutes before being left to stand at room temperature overnight. The mixture was then poured into saturated aqueous ammonium chloride solution (450 ml) and extracted twice with diethyl ether. The organic extracts were combined and the solvent removed under reduced pressure to give a residue which was chromatographed on silica gel eluting with a solvent gradient of 4:0 changing to 4:1, by volume, dichloromethane:diethyl ether to give the title compound (5.9 g) as an oil.

$^1$H-NMR (CDCl$_3$): δ=7.72–7.90 (4H, m), 7.46–7.57 (3H, m), 7.20–7.38 (5H, m), 3.85 (2H, q), 3.71 (1H, s), 3.37 (2H, s), 2.60–2.80 (4H, m), 2.15–2.40 (4H, m), 0.80 (3H, t) ppm.

PREPARATION 4

Ethyl 2-(1-benzyl-4-(2-naphthyl)piperidin-4-yl)ethanoate

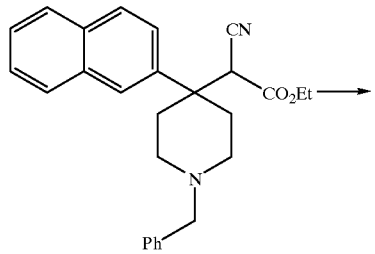

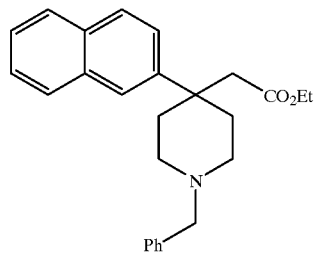

A solution of potassium hydroxide (10 g) in water (30 ml) was added to a solution of ethyl 2-cyano-2-(1-benzyl-4-(2-naphthyl)piperidin-4-yl)ethanoate (5.9 g) (see Preparation 3) in ethanol (40 ml) resulting in formation of a suspension which was stirred at room temperature overnight and then heated on a steam bath until a clear solution was formed. The solution was divided between two microwave vessels and microwaved at 690 kPa (100 psi)/100% power for 5 hours. The solutions were then combined, the solvent removed under reduced pressure and the residue azeotroped 4 times with toluene to remove any residual water. The residue was dissolved in ethanol (250 ml), cooled in an ice-bath and the solution saturated with hydrogen chloride gas at which stage a precipitate was formed. The mixture was left to stand at room temperature for 3 days, filtered and the solvent removed from the filtrate under reduced pressure to give a residue which was chromatographed on silica gel eluting with a solvent gradient of 98:2 changing to 96:4, by volume, dichloromethane:methanol to give the hydrochloride of the title compound. The hydrochloride salt was partitioned between dichloromethane and saturated aqueous sodium carbonate solution, the organic phase separated, dried over anhydrous sodium sulphate and the solvent removed under reduced pressure to give the title compound (3.6 g) as an oil.

$^1$H-NMR (CDCl$_3$): δ=7.70–7.85 (4H, m), 7.40–7.52 (3H, m), 7.20–7.32 (5H, m), 3.78 (2H, q), 3.41 (2H, s), 2.58–2.70 (4H, m), 2.30–2.50 (4H, m), 2.10–2.20 (2H, m), 0.84 (3H, t) ppm.

PREPARATION 5

4-(2-Naphthyl)-4-(2-hydroxyethyl)-N-benzylpiperidine

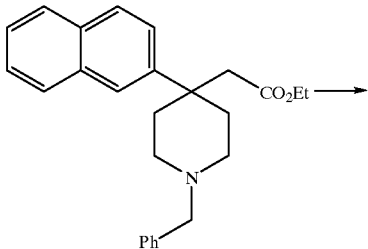

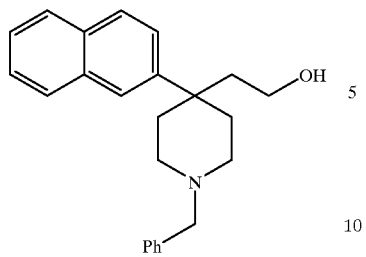

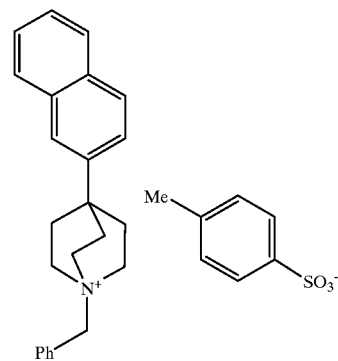

Ethyl 2-(1-benzyl-4-(2-naphthyl)piperidin-4-yl)ethanoate (5.8 g) (see Preparation 4) was dissolved in anhydrous diethyl ether (100 ml), cooled in an ice-bath and lithium aluminium hydride (0.57 g) added, portionwise. The mixture was stirred at room temperature for 30 minutes, water (0.8 ml) was then carefully added followed by 2N aqueous sodium hydroxide solution (0.8 ml) and further water (1.6 ml). The mixture was stirred for 20 minutes and the resulting granular precipitate removed by filtration. The solvent was removed from the filtrate under reduced pressure to give a solid which was dissolved in dichloromethane, dried over anhydrous sodium sulphate and the solvent again removed under reduced pressure to yield 4-(2-naphthyl)-4-(2-hydroxyethyl)-N-benzylpiperidine (2.2 g) as a white solid.

The granular precipitate was triturated with dichloromethane and filtered. The filtrate was washed with water, dried over anhydrous sodium sulphate and the solvent removed under reduced pressure to yield a second crop of 4-(2-naphthyl)-4-(2-hydroxyethyl)-N-benzylpiperidine (2.7 g) as a white solid.

$^1$H-NMR (CDCl$_3$): δ=7.75–7.86 (3H, m), 7.70 (1H, s), 7.43–7.50 (3H, m), 7.20–7.35 (5H, m), 3.35–3.45 (4H, m), 2.60–2.70 (2H, m), 2.25–2.40 (4H, m), 1.92–2.04 (4H, m), 0.90 (1H, br. s) ppm.

PREPARATION 6

4-(2-Naphthyl)-N-benzylquinuclinium 4-methylphenylsulphonate

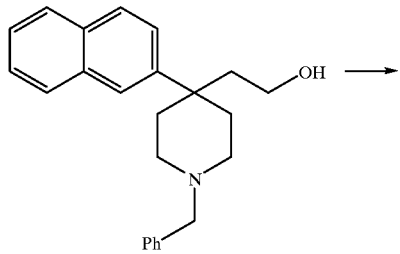

4-(2-Naphthyl)-4-(2-hydroxyethyl)-N-benzylpiperidine (4.9 g) (see Preparation 5) was dissolved in pyridine (30 ml) and cooled in an ice-bath before addition of 4-methylphenylsulphonyl chloride (3.0 g). The mixture was left at 0° C. for 16 hours before removal of the solvent under reduced pressure. The residue was suspended in 10% w/w aqueous potassium carbonate solution (120 ml) and extracted with toluene (2×130 ml). The combined organic phases were washed with 10% w/w aqueous potassium carbonate solution, dried over anhydrous potassium carbonate for 10 minutes and filtered. The filtrate was collected and the volume reduced to ~60 ml under reduced pressure to yield a suspension. This was then heated at 90° C. for 6 hours, left to stand at room temperature overnight and the resulting precipitate filtered off. The precipitate was washed sequentially with toluene and diethyl ether and dried to yield 4-(2-naphthyl)-N-benzylquinuclinium 4-methylphenylsulphonate (3.5 g) as a white solid.

$^1$H-NMR (CDCl$_3$): δ=7.90 (2H, d), 7.78 (3H, m), 7.30–7.65 (9H, m), 7.16 (2H, d), 4.89 (2H, s), 3.80–3.95 (6H, m), 2.31 (3H, s), 2.13–2.29 (6H, m) ppm.

PREPARATION 7

4-(2-Naphthyl)quinuclidine

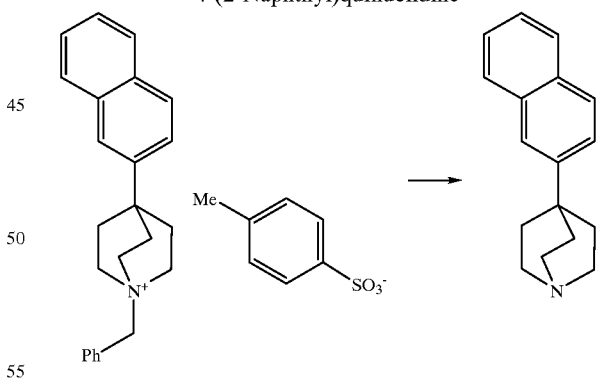

4-(2-Naphthyl)-N-benzylquinuclinium 4-methylphenylsulphonate (3.5 g) (see Preparation 6 was dissolved in methanol (35 ml), 10% w/w palladium-on-carbon (0.5 g) was added and the mixture hydrogenated for 40 hours at 345 kPa (50 psi). The mixture was then filtered through a short column of Arbacel (trade mark) filter aid and the solvent removed from the filtrate under reduced pressure to give a residue. This was partitioned between diethyl ether and 1N aqueous sodium hydroxide solution. The two phases were separated and the aqueous phase extracted twice with diethyl ether. The organic phases were combined and the solvent removed under reduced pressure. The resulting residue was dissolved in ethyl acetate and the solution washed sequentially with 0.88 aqueous ammonia solution and brine before being dried over anhydrous sodium sulphate. The solvent was again removed under reduced pressure yield 4-(2-naphthyl)quinuclidine (1.56 g) as a solid.

$^1$H-NMR (CDCl$_3$): δ=7.80 (3H, d), 7.63 (1H, s), 7.40–7.52 (3H, m), 3.00–3.15 (6H, m), 1.82–1.96 (6H, m) ppm.

PREPARATION 8

Ethyl 2-cyano-2-(1-benzyl-4-(3,5-dimethylphenyl)piperidin-4-yl)ethanoate

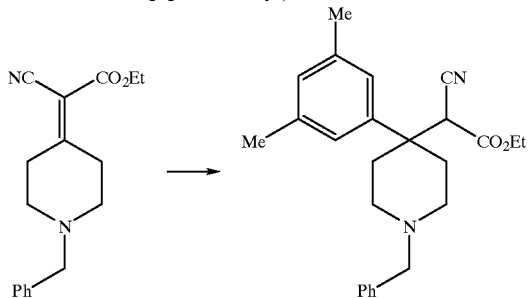

1,3-Dimethyl-5-bromobenzene (15.6 g) was dissolved in anhydrous diethyl ether (60 ml) and added to a vigorously stirred mixture of magnesium turnings (2.2 g) and 2–3 iodine crystals under a nitrogen atmosphere. Gentle heating was applied to initiate formation of the Grignard reagent and once the spontaneous refluxing had subsided the mixture was heated under reflux for a further 30 minutes. The mixture was cooled in an ice-bath and a solution of ethyl 2-(1-benzylpiperidin-4-ylidene)-2-cyanoacetate (8.0 g) (see Preparation 2) in anhydrous tetrahydrofuran (80 ml) added over 20 minutes. The mixture was stirred at 0° C. for 15 minutes before being left to stand at room temperature for 3 days. The mixture was then poured into saturated aqueous ammonium chloride solution (300 ml) and extracted twice with diethyl ether. The organic extracts were combined and the solvent removed under reduced pressure to give a residue which was chromatographed on silca gel eluting with a solvent gradient of 3:0 changing to 3:1, by volume, dichloromethane:diethyl ether to give the title compound (4.7 g) as an oil.

$^1$H-NMR (CDCl$_3$): δ=7.20–7.35 (5H, m), 6.91 (3H, s), 3.94 (2H, q), 3.61 (1H, s), 3.40 (2H, s), 2.40–2.70 (4H, m), 2.30 (6H, s), 2.10–2.22 (4H, m), 1.00 (3H, t) ppm.

PREPARATION 9

Ethyl 2-(1-benzyl-4-(3,5-dimethylphenyl)piperidin-4-yl)ethanoate

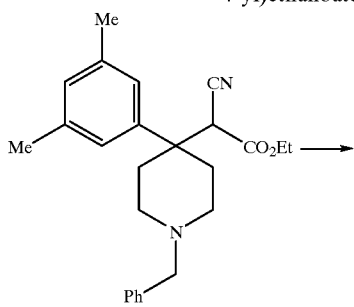

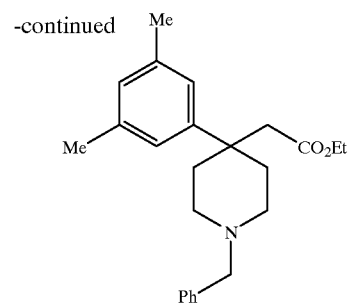

A solution of potassium hydroxide (3.4 g) in water (20 ml) was added to a solution of ethyl 2-cyano-2-(1-benzyl-4-(3,5-dimethylphenyl)piperidin-4-yl)ethanoate (4.7 g) (see Preparation 8) in ethanol (24 ml) and the mixture microwaved at 345 kPa (100 psi)/100% power for 2.5 hours. The solvent was removed under reduced pressure and the residue azeotroped with toluene to remove any residual water. The residue was dissolved in ethanol (100 ml), cooled in an ice-bath and the solution saturated with hydrogen chloride gas. The mixture was left to stand at room temperature overnight before re-saturating the solution with hydrogen chloride gas and leaving to stand for a further 24 hours. The solution was filtered and the solvent removed from the filtrate under reduced pressure to give a residue which was dissolved in saturated aqueous sodium carbonate solution and extracted twice with dichloromethane. The organic phases were combined, dried over anhydrous sodium sulphate and the solvent removed under reduced pressure to give a residue which was chromatographed on silica gel eluting with a solvent gradient of 97:3 changing to 90:10, by volume, dichloromethane:methanol to give the title compound (2.0 g) as an oil.

$^1$H-NMR (CDCl$_3$): δ=7.20–7.35 (5H, m), 6.90 (2H, s), 6.82 (1H, s), 3.80–3.90 (2H, q), 3.43 (2H, s), 2.50–2.63 (4H, m), 2.20–2.40 (10H, m), 1.92–2.08 (2H, m), 0.95–1.03 (3H, t) ppm.

PREPARATION 10

4-(3,5-Dimethylphenyl)-4-(2-hydroxyethyl)-N-benzylpiperidine

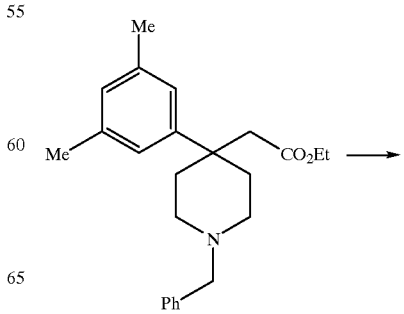

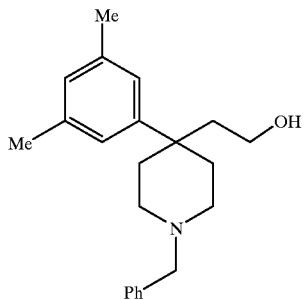

Ethyl 2-(1-benzyl-4-(3,5-dimethylphenyl)piperidin-4-yl) ethanoate (2.0 g) (see Preparation 9) was dissolved in anhydrous diethyl ether (50 ml), cooled in an ice-bath and lithium aluminium hydride (0.21 g) added portionwise. The mixture was stirred at room temperature for 45 minutes, water (0.3 ml) was carefully added, followed by 2N aqueous sodium hydroxide solution (0.3 ml) and fiiter water (0.6 ml). The mixture was stirred for 20 minutes and the resulting granular precipitate removed by filtration and washed with diethyl ether. The solvent was removed from the filtrate under reduced pressure to give a solid which was dissolved in dichloromethane, dried over anhydrous sodium sulphate and the solvent again removed under reduced pressure to yield 4-(3,5-dimethylphenyl)-4-(2-hydroxyethyl)-N-benzylpiperidine (1.67 g) as an oil.

$^{1}$H-NMR (CDCl$_3$): δ=7.20–7.35 (5H, m), 6.90 (2H, s), 6.83 (1H, s), 3.32–3.43 (4H, m), 2.54–2.64 (2H, m), 2.13–2.37 (11H, m), 1.80–1.90 (4H, m) ppm.

PREPARATION 11

4-(3,5-Dimethylphenyl)-N-benzylquinuclinium 4-methylphenylsulphonate

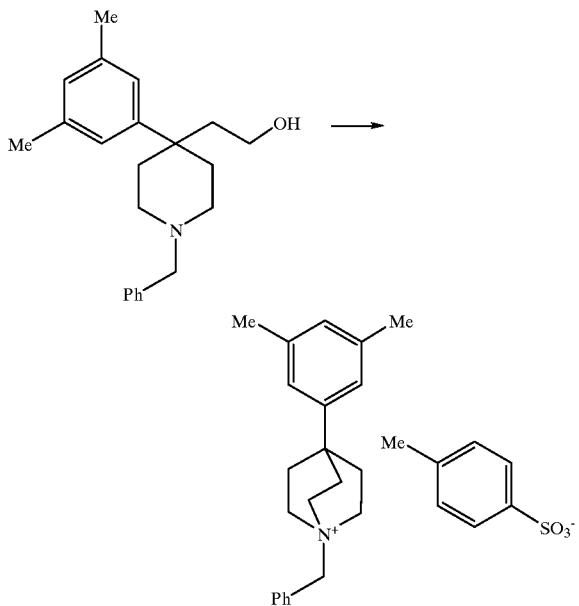

4-(3,5-Dimethylphenyl)-4-(2-hydroxyethyl)-N-benzylpiperidine (1.6 g) (see Preparation 10) was dissolved in pyridine (10 ml), cooled in an ice-bath and 4-methylphenylsulphonyl chloride (1.0 g) added in 4 portions over 10 minutes. The mixture was left at 0° C. for 16 hours before removal of the solvent under reduced pressure. The residue was suspended in 10% w/w aqueous potassium carbonate solution (30 ml) and extracted with toluene (50 ml). The organic phase was washed with 10% w/w aqueous potassium carbonate solution, dried over anhydrous potassium carbonate and filtered. The filtrate was collected and the volume reduced to ~12 ml under reduced pressure to yield a suspension which was then heated at 90° C. for 3 hours, allowed to cool room temperature and the volume reduced to ~5 ml at which point the product began to precipitate out of solution. Diethyl ether (30 ml) was added, the precipitate filtered, washed with diethyl ether and dried to yield 4-(3,5-dimethylphenyl)-N-benzylquinuclinium 4-methylphenylsulphonate (1.59 g) as a white solid.

$^{1}$H-NMR (CDCl$_3$): δ=7.96 (2H, d), 7.58 (2H, d), 7.30–7.40 (3H, m), 7.16 (2H, d), 6.96 (1H, s), 6.75 (2H, s), 4.86 (2H, d), 3.72–3.82 (6H, m), 2.34 (3H, s), 2.25 (6H, s), 2.05–2.12 (6H, m) ppm.

PREPARATION 12

4-(3,5-Dimethylphenyl)quinuclidine

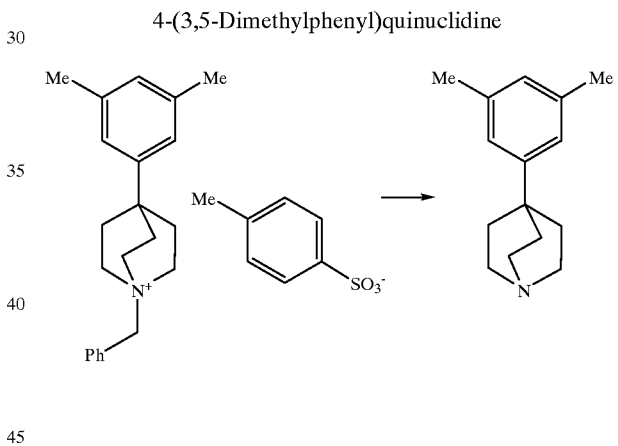

4-(3,5-Dimethylphenyl)-N-benzylquinuclinium 4-methylphenylsulphonate (1.4 g) (see Preparation 11) was dissolved in methanol (14 ml), 10% w/w palladium-on-carbon (0.2 g) was added and the mixture hydrogenated for 40 hours at 345 kPa (50 psi). The mixture was then filtered through a short column of Arbacel (trade mark) filter aid and the solvent removed under reduced pressure to give a residue. This was partitioned between diethyl ether and 1N aqueous sodium hydroxide solution. The two phases were separated and the aqueous phase extracted twice with diethyl ether. The organic phases were combined and the solvent removed under reduced pressure. The resulting residue was dissolved in ethyl acetate and the solution washed with brine before being dried over anhydrous sodium sulphate. The solvent was again removed under reduced pressure yield 4-(3,5-dimethylphenyl)quinuclidine (0.59 g) as a white solid.

$^{1}$H-NMR (CDCl$_3$): δ=6.89 (2H, s), 6.83 (1H, s), 2.95–3.05 (6H, m), 2.33 (6H, s), 1.70–1.81 (6H, m) ppm.

PREPARATION 13

2-(3,4-Dichlorophenyl)-3-(1,3-dioxolan-2-yl)propanenitrile

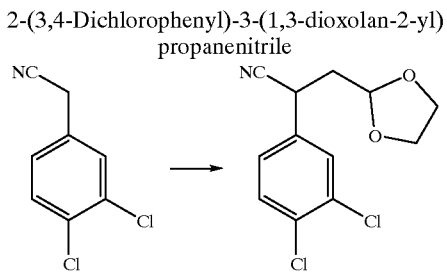

Sodium hydride (60% w/w dispersion in mineral oil) (4.73 g) was suspended in tetrahydrofuran (70 ml) under a nitrogen atmosphere and the mixture cooled in an ice-bath. A solution of 3,4-dichlorophenylacetonitrile (20 g) in tetrahydrofrran (80 ml) was added dropwise over 35 minutes, the mixture allowed to warm to room temperature and left to stir for 16 hours. 2-Bromomethyl-1,3-dioxolane (19.71 g) and tetra-n-butylammonium iodide (2 g) were added and the resulting mixture was heated at reflux for 4 hours. The mixture was cooled and partitioned between ethyl acetate and water. The organic layer was separated and washed with brine. The organic solvents were removed under reduced pressure to yield a brown oil which was chromatographed on silica gel using 80:20, by volume, ethyl acetate:hexane as the eluent to yield the product as an orange mobile oil. This oil was then dissolved in methanol, cooled in ice and the precipitate that formed was filtered off, washed with methanol and dried under reduced pressure to yield 2-(3,4-dichlorophenyl)-3-(1,3-dioxolan-2-yl)propanenitrile (15.8 g) as a white solid.

$^1$H-NMR (CDCl$_3$): δ=7.40–7.50 (2H, m), 7.20–7.25 (1H, dd), 4.95 (1H, dd), 3.82–4.05 (5H, m), 2.30–2.40 (1H, m), 2.05–2.15 (1H, m) ppm.

PREPARATION 14

2-(3,4-Dichlorophenyl)-3-(1,3-dioxolan-2-yl)propan-1-al

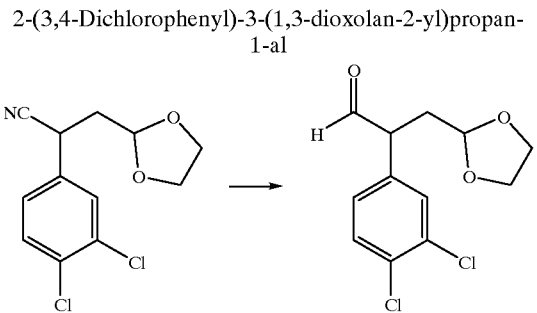

2-(3,4-Dichlorophenyl)-3-(1,3-dioxolan-2-yl) propanenitrile (64 g) (see Preparation 13) was suspended in anhydrous toluene (500 ml) and cooled to −70° C. under a nitrogen atmosphere. Diisobutylaluminium hydride (200 ml of a 1.5M solution in toluene) was then added over 50 minutes, by which time a clear solution was achieved. The mixture was stirred at −70° C. for a further 30 minutes and then allowed to warm slowly to −20° C. Water (24 ml) was carefully added (exothermic reaction) before pouring the mixture into a 15% (by weight) aqueous solution of citric acid (1800 ml). Toluene (100 ml) was added and the mixture was vigorously stirred for 1 hour. The resulting emulsion was filtered through a short column of Arbacel (trade mark) filter aid to give two clear phases which were separated. The organic phase was washed with brine, dried over anhydrous sodium sulphate and the solvent removed under reduced pressure to give 2-(3,4-dichlorophenyl)-3-(1,3-dioxolan-2-yl)propan-1-al as a yellow oil (53.5 g)

$^1$H-NMR (CDCl$_3$): δ=9.90 (1H, s), 7.10–7.50 (3H, m), 4.89 (1H, t), 3.70–4.00 (5H, m), 1.45–1.55 (1H, m), 2.20–2.10 (1H, m) ppm.

PREPARATION 15

2-(3,4-Dichlorophenyl)-3-(1,3-dioxolan-2-yl)propan-1-al

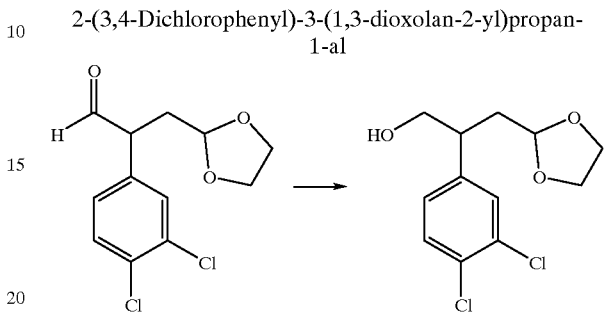

Sodium borohydride (5 g) was added in two portions, over 40 minutes, to an ice-cooled solution of 2-(3,4-dichlorophenyl)-3-(1,3-dioxolan-2-yl)propan-1-al (53.5 g) (see Preparation 14) in ethanol (300 ml). The mixture was stirred for a further 30 minutes before removing the solvent under reduced pressure to give a residue. This was suspended in water (200 ml), cooled to 0° C. and the mixture acidified (pH<6) with glacial acetic acid. Dichloromethane was added and the aqueous phase basified (pH>8) by addition of solid sodium carbonate. A further amount of dichloromethane (200 ml) was added and the organic and aqueous phases separated. The aqueous phase was further extracted with dichloromethane (200 ml). The organic phases were combined, washed with brine, dried over anhydrous sodium sulphate and the solvent removed under reduced pressure to give 2-(3,4-dichlorophenyl)-3-(1,3-dioxolan-2-yl)propan-1-ol (54.6 g) as a yellow oil.

$^1$H-NMR (CDCl$_3$): δ=7.30–7.45 (2H, m), 7.09 (1H, dd), 4.79 (1H, t), 3.70–4.00 (6H, m), 2.97–3.08 (1H, m), 1.96–2.09 (3H, m ) ppm.

PREPARATION 16

1-Methanesulphonyloxy-2-(3,4-dichlorophenl)-3-(1,3-dioxolan-2-yl)propane

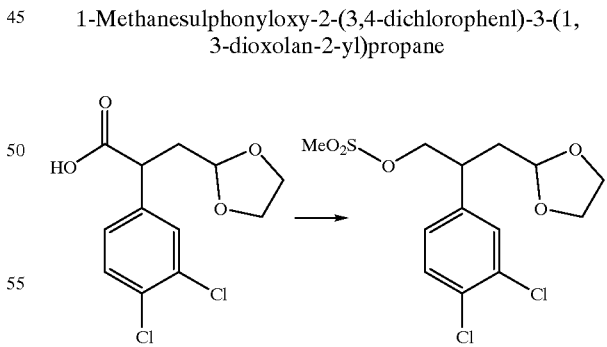

Methanesulphonyl chloride (5.5 g) was added over 10 minutes to an ice-cooled solution of 2-(3,4-dichlorophenyl)-3-(1,3-dioxolan-2-yl)propan-1-ol (12 g) (see Preparation 15) and triethylamine (5.7 g) in dichloromethane (100 ml). The mixture was stirred for 30 minutes before further addition of dichloromethane (50 ml). The solution was then washed sequentially with water (3×50 ml) and brine (50 ml) before drying over anhydrous sodium sulphate. Removal of the solvent under reduced pressure gave 1-methanesulphonyloxy-2-(3,4-dichlorophenyl)-3-(1,3-dioxolan-2-yl)propane as a yellow oil (15.6 g) which solidified upon standing.

¹H-NMR (CDCl₃): δ=7.41 (1H, d), 7.34 (1H, d), 7.10 (1H, dd), 4.75 (1H, t), 4.26–4.43 (2H, m), 3.90–4.00 (2H, m), 3.80–3.87 (2H, m), 3.30 (1H, m), 2.90 (3H, s), 2.00–2.10 (2H, m) ppm.

PREPARATION 17

1-(Imidazol-1-yl)-2-(3,4-dichlorophenyl)-3-(1,3-dioxolan-2-yl)propane

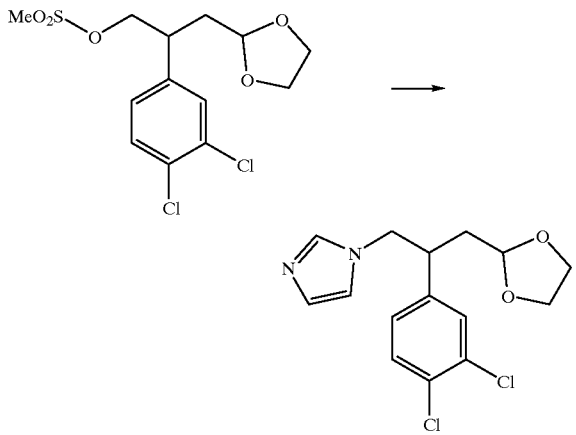

1-Methanesulphonyloxy-2-(3,4-dichlorophenyl)-3-(1,3-dioxolan-2-yl)propane (15.5 g) (see Preparation 16) and imidazole (9 g) were dissolved in anhydrous acetonitrile (100 ml) and the mixture heated at reflux for 90 hours. The solvent was removed under reduced pressure, the residue dissolved in dichloromethane (100 ml) and the solvent again removed under reduced pressure. The residue was dissolved in dichloromethane (300 ml) and washed with sufficient aqueous sodium carbonate solution to ensure that the aqueous phase reached pH14. The two phases were separated and the aqueous phase extracted with dichloromethane (100 ml). The organic phases were then combined and the solvent removed under reduced pressure to give a residue which was chromatographed on silica gel, eluting with a solvent gradient of 99:1 changing to 95:5, by volume, dichloromethane:methanol to give 1-(imidazol-1-yl)-2-(3,4-dichlorophenyl)-3-(1,3-dioxolan-2-yl)propane (11.1 g) as an orange oil.

¹H-NMR (CDCl₃): δ=6.95–7.40 (4H, m), 6.85 (1H, dd), 6.69 (1H, s), 4.69 (1H, m), 4.15–4.25 (1H, m), 3.70–4.10 (5H, m), 3.15–3.25 (1H, m), 1.90–2.10 (2H, m) ppm.

PREPARATION 18

3-(3,4-Dichlorophenyl)-4-(imidazol-1-yl)butan-1-al

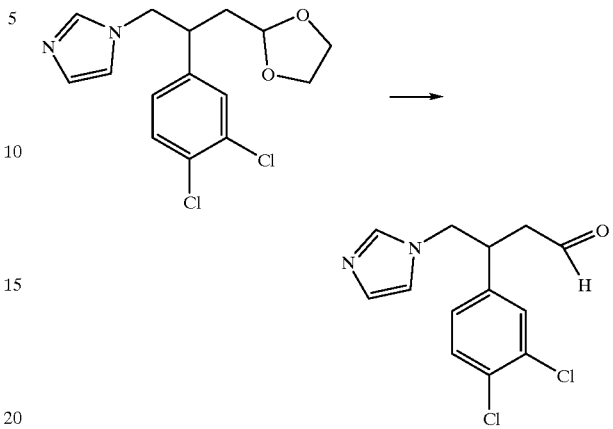

5N Aqueous hydrochloric acid solution (100 ml) was added to an ice-cooled solution of 1-(imidazol-1-yl)-2-(3,4-dichlorophenyl)-3-(1,3-dioxolan-2-yl)propane (11 g) (see Preparation 17) in tetrahydrofliran (100 ml). The mixture was allowed to warm slowly to room temperature and then left to stand for 24 hours. The tetrahydrofuran was removed under reduced pressure and the acidic phase extracted with dichloromethane (2×100 ml). The organic phases were combined, washed with brine and dried over anhydrous sodium sulphate. The solvent was removed under reduced pressure to give the crude product which was chromatographed on silica gel eluting with a solvent gradient of 97.5:2.5 changing to 95:5, by volume, dichloromedane:methanol, to give 3-(3,4-dichlorophenyl)-4-(imidazol-1-yl)butan-1-al (4.4 g) as a viscous oil.

¹H-NMR (CDCl₃): δ=9.70 (1H, s), 7.38 (1H, d), 7.20–7.30 (2H, m), 7.01 (1H, s), 6.89 (1H, dd), 6.71 (1H, s), 4.00–4.22 (2H, m), 3.60 (1H, m), 2.72–2.92 (2H, m) ppm.

PREPARATION 19

3-(3,4-Dichlorophenyl)-4-(imidazol-1-yl)butan-1-ol

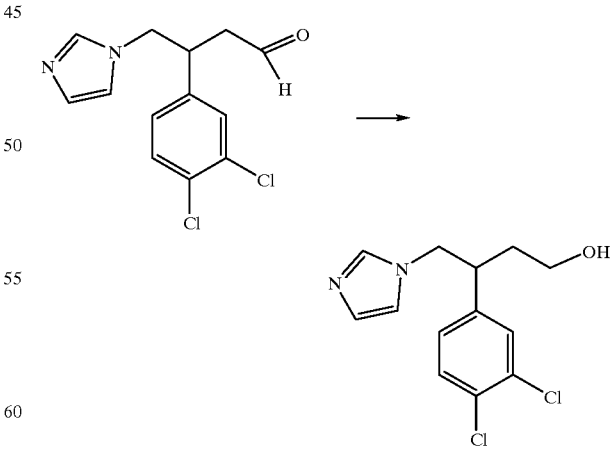

Sodium borohydride (0.52 g) was added in three portions, over 5 minutes, to an ice-cooled solution of 3-(3,4-dichlorophenyl)-4-(imidazol-1-yl)butan-1-al (3.3 g) (see Preparation 18) in ethanol (25 ml). The mixture was stirred for a erther hour before removing the solvent under reduced pressure to give a residue. The residue was then suspended in water (50 ml), cooled to 0° C. and the mixture first acidified to pH1 with 2N aqueous hydrochloric acid solution and then basified to pH14 by addition of solid sodium carbonate before being extracted with ethyl acetate (3×200 ml). The organic phases were combined, dried over anhydrous sodium sulphate and the solvent removed under reduced pressure to yield 3-(3,4-dichlorophenyl)-4-(imidazol-1-yl)butan-1-ol (2.84 g) as a cream solid.

$^1$H-NMR (CDCl$_3$): δ=7.35 (1H, d), 7.15–7.30 (2H, m), 6.95 (1H, s), 6.89 (1H, d), 6.70 (1H, s), 4.00–4.25 (2H, m), 3.60–3.70 (1H, m), 3.40–3.50 (1H, m), 3.15–3.30 (1H, m), 2.10 (1H, br. s), 1.75–2.00 (2H, m) ppm.

PREPARATION 20

4-Cyano-4-(3,4-dichlorophenyl)but-1-ene

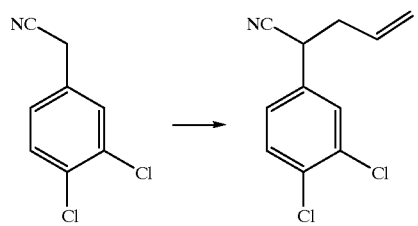

3,4-Dichlorophenylacetonitrile (80 g) was dissolved in anhydrous tetrahydrofuran (800 ml) under a nitrogen atmosphere, cooled to −70° C., and lithium di-isopropylamide (320 ml of a 1.5M solution in cyclohexane) added. The mixture was stirred at −70° C. for 30 minutes, allyl bromide (63 g) added over 15 minutes and the mixture stirred for a further 30 minutes. 2N Aqueous hydrochloric acid solution (600 ml) was then added and the mixture extracted twice with diethyl ether. The organic extracts were combined and the solvent removed under reduced pressure. The resulting residue was dissolved in dichloromethane, dried over anhydrous sodium sulphate and the solvent removed under reduced pressure to give a red mobile oil. This was chromatographed on silica gel eluting with 4:1, by volume, hexane:dichloromethane to give 4-cyano-4-(3,4-dichlorophenyl)but-1-ene (94.8 g) as an oil.

$^1$H-NMR (CDCl$_3$): δ=7.40–7.51 (2H, m), 7.14–7.21 (1H, m), 5.70–5.95 (1H, m), 5.13–5.27 (2H, m), 3.84 (1H, t), 2.56–2.70 (2H, m) ppm.

PREPARATION 21

4-(3,4-Dichlorophenyl)-4-formylbut-1-ene

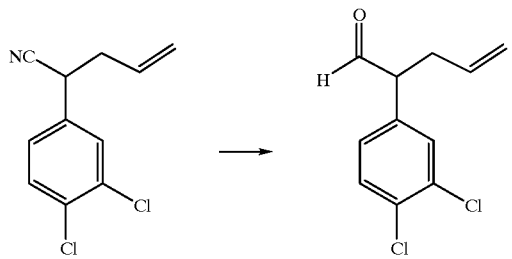

4-Cyano-4-(3,4-dichlorophenyl)but-1-ene (13 g) (see Preparation 20) was dissolved in anhydrous toluene (100 ml) and cooled to −70° C. under a nitrogen atmosphere. Diisobutylaluminium hydride (50 ml of a 1.5M solution in toluene) was added to the solution over 30 minutes, the mixture stirred at −70° C. for a further 30 minutes and then allowed to warm slowly to −10° C. Water (6 ml) was carefully added (exothermic reaction) before pouring the mixture into a 15% (by weight) aqueous solution of citric acid (500 ml), followed by further addition of toluene (300 ml) and vigorous stirring of the mixture for 30 minutes. The two phases were separated, the organic phase washed with brine, dried over anhydrous sodium sulphate and the solvent removed under reduced pressure to give 4-(3,4-dichlorophenyl)-4-formylbut-1-ene as an oil (14 g).

$^1$H-NMR (CDCl$_3$): δ=9.68 (1H, s), 7.48 (1H, d), 7.31 (1H, s), 7.03 (1H, d), 5.61–5.77 (1H, m), 4.94–5.13 (2H, m), 3.56–3.65 (1H, m), 2.77–2.91 (1H, m), 2.40–2.54 (1H, m) ppm.

PREPARATION 22

4-(3,4-Dichlorophenyl)-5-hydroxypent-1-ene

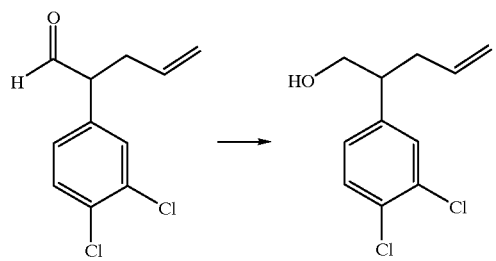

Sodium borohydride (2.2 g) was added in four portions, over 10 minutes, to an ice-cooled solution of 4-(3,4-dichlorophenyl)-4-formylbut-1-ene (13 g) (see Preparation 21) in ethanol (100 ml). The mixture was stirred for a further 30 minutes before removing the solvent under reduced pressure to give a residue. This was suspended in water (50 ml), cooled to 0° C. and the mixture acidified (pH<6) with 2N aqueous hydrochloric acid solution. The mixture was extracted three times with dichloromethane, the organic phases combined and the solvent removed under reduced pressure. Dichloromethane (200 ml) was then added, the mixture stirred and filtered and the solvent removed from the filtrate under reduced pressure to give an oil. This was chromatographed on silica gel eluting with dichloromethane to give 4-(3,4-dichlorophenyl)-5-hydroxypent-1-ene (7 g) as a orange oil.

$^1$H-NMR (CDCl$_3$): δ=7.24–7.45 (2H, m), 7.06 (1H, dd), 5.61–5.75 (1H, m), 4.96–5.10 (2H, m), 3.70–3.90 (2H, m), 2.80–2.91 (1H, m), 2.30–2.55 (2H, m), 1.32 (1H, t) ppm.

PREPARATION 23

4-(3,4-Dichlorophenyl)-5-(methanesulphonyloxy)pent-1-ene

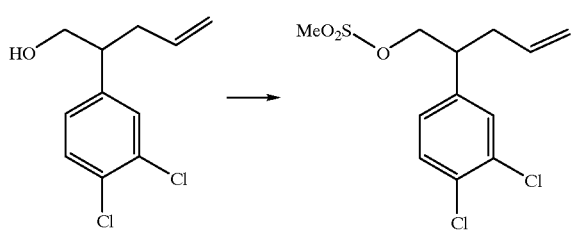

A solution of methanesulphonyl chloride (2.3 g) in dichloromethane (10 ml) was added to an ice-cooled solution of 4-(3,4-dichlorophenyl)-5-hydroxypent-1-ene (4.3 g) (see Preparation 22) and triethylamine (2.5 g) in dichloromethane (50 ml) over 10 minutes. The mixture was stirred for a further 30 minutes before being washed sequentially with water (3×25 ml) and brine (25 ml), then dried over anhydrous sodium sulphate. Removal of the solvent under reduced pressure gave 4-(3,4-dichlorophenyl)-5-(methanesulphonyloxy)pent-1-ene (5.4 g) as an oil.

$^1$H-NMR (CDCl$_3$): δ=7.42 (1H, d), 7.30 (1H, s), 7.04 (1H, dd), 5.56–5.72 (1H, m), 5.01–5.10 (2H, m), 4.22–4.39 (2H, m), 3.05–3.15 (1H, m), 2.88 (3H, s), 2.33–2.60 (2H, m) ppm.

PREPARATION 24

4-(3,4-Dichlorophenyl)-5-(imidazol-1-yl)pent-1-ene (and hydrochloride salt)

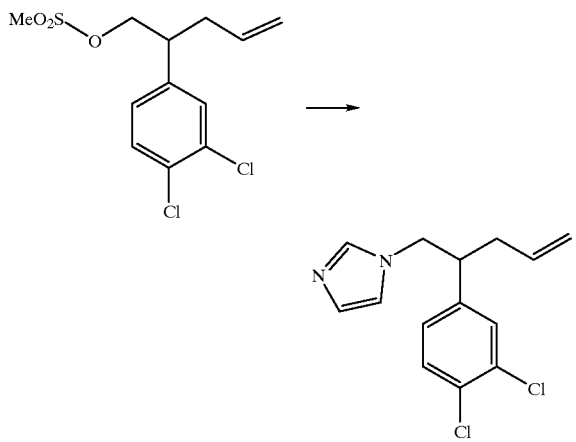

4-(3,4-Dichlorophenyl)-5-(methanesulphonyloxy)pent-1-ene (5.4 g) (see Preparation 23) and imidazole (3.6 g) were dissolved in anhydrous acetonitrile (40 ml) and the mixture heated under reflux for 100 hours. The solvent was removed under reduced pressure, the residue dissolved in dichloromethane and the solvent removed under reduced pressure. The residue was dissolved in dichloromethane (100 ml) and washed with sufficient aqueous sodium carbonate solution to ensure that the aqueous phase reached pH14. The two phases were separated and the aqueous phase extracted with dichloromethane (100 ml). The organic phases were combined and the solvent removed under reduced pressure to give a residue which was chrornatographed on silica gel eluting with a solvent gradient of 100:0 changing to 98:2, by volume, dichloromethane:methanol, to give 4-(3,4-dichlorophenyl)-5-(imidazol-1-yl)pent-1-ene (3.45 g) as an orange oil.

$^1$H-NMR (CDCl$_3$): δ=7.35 (1H, d), 7.15–7.30 (2H, m); 6.99 (1H, s), 6.84 (1H, d), 6.69 (1H, s), 5.55–5.70 (1H, m), 5.07 (2H, d), 3.95–4.22 (2H, m), 2.95–3.10 (1H, m), 2.32–2.45 (2H, m) ppm.

The hydrochloride salt was prepared by dissolving the free base in dichloromethane, treating the solution with hydrogen chloride gas and removal of the solvent under reduced pressure to give 4-(3,4-dichlorophenyl)-5-(imidazol-1-yl)pent-1-ene hydrochloride as a foam.

PREPARATION 25

(alternative method to Preparation 18) 3-(3,4-Dichlorophenyl)-4-(imidazol-1-yl)butan-1-al

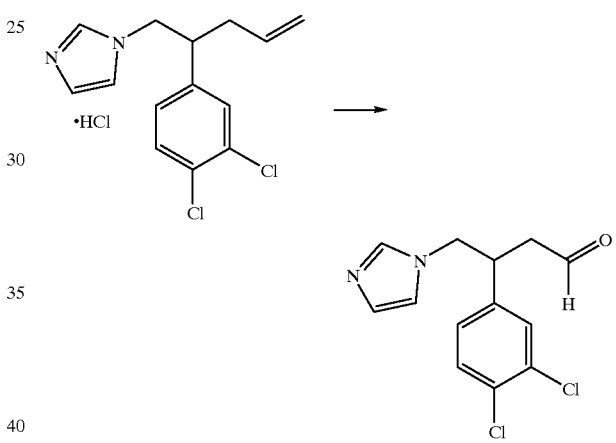

4-(3,4-Dichlorophenyl)-5-(imidazol-1-yl)pent-1-ene hydrochloride (3.6 g) (see Preparation 24) was dissolved in a mixture of acetonitrile (50 ml) and water (20 ml) and osmium tetroxide (4 ml of a 0.05M solution in toluene) added. The mixture was stirred for 30 minutes, sodium periodate (5.3 g) added and stirring continued for 2 hours. A further portion of acetonitrile (20 ml) was added and stirring continued for 16 hours before removal of the organic solvent under reduced pressure to give an aqueous suspension. This was basified to pH>7 by the addition of solid sodium carbonate. The mixture was then extracted with dichloromethane, the organic phase dried over anhydrous sodium sulphate and the solvent removed under reduced pressure to give a dark oil which was chromatographed on silica gel eluting with a solvent gradient of 98:2 changing to 92.5:7.5, by volume, dichloromethane:methanol to give 3-(3,4-dichlorophenyl)-4-(imidazol-1-yl)butan-1-al (2.28 g) as a colourless, viscous oil.

$^1$H-NMR (CDCl$_3$): δ=9.70 (1H, s), 7.38 (1H, d), 7.20–7.30 (2H, m), 7.01 (1H, s), 6.89 (1H, dd), 6.71 (1H, s), 4.00–4.22 (2H, m), 3.60 (1H, m), 2.72–2.92 (2H, m) ppm.

PREPARATION 26

2-(3,4-Dichlorophenyl)-4-(tetrahydropyran-2-yloxy)butanenitrile

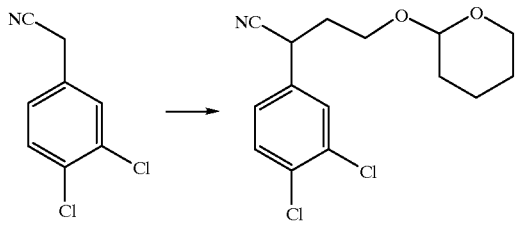

To a mixture of sodium hydride (60% w/w dispersion in mineral oil) (19.24 g) and anhydrous tetrahydrofuran (450 ml) at 0° C. under a nitrogen atmosphere was added a solution of 3,4-dichlorophenylacetonitrile (89.5 g) in anhydrous tetrahydrofuran (450 ml), dropwise over 40 minutes. After a further 30 minutes, a solution of 2-(2-bromoethoxy)tetrahydropyran (100 g) in anhydrous tetrahydrofuran (100 ml) was added. The mixture was allowed to warm to room temperature and then stirred for 14 hours. 30% w/w Aqueous ammonium chloride solution (500 ml) was added and the mixture extracted with diethyl ether (2×400 ml). The organic extracts were combined, washed with water (2×400 ml), dried over anhydrous magnesium sulphate and the solvent removed under reduced pressure. The residue was chromatographed on silica gel eluting with a solvent gradient of 1:9 changing to 1:1, by volume, diethyl ether:hexane to give 2-(3,4-dichlorophenyl)-4-(tetrahydropyran-2-yloxy)-butanenitrile (51 g) as an oil and as a mixture of diastereomers.

$^1$H-NMR (CDCl$_3$) (mixture of 2 diastereomers): δ=7.25–7.50 (2H, m), 7.20–7.25 (1H, m), 4.50–4.60 (1H, m), 4.00–4.10 (1H, m), 2.80–2.95 (2H, m), 2.40–2.65 (2H, m), 2.05–2.30 (2H, m), 1.50–1.90 (6H, m) ppm.

PREPARATION 27

2-(3,4-Dichlorophenyl)-4-(tetrahydropyran-2-yloxy)butan-1-al

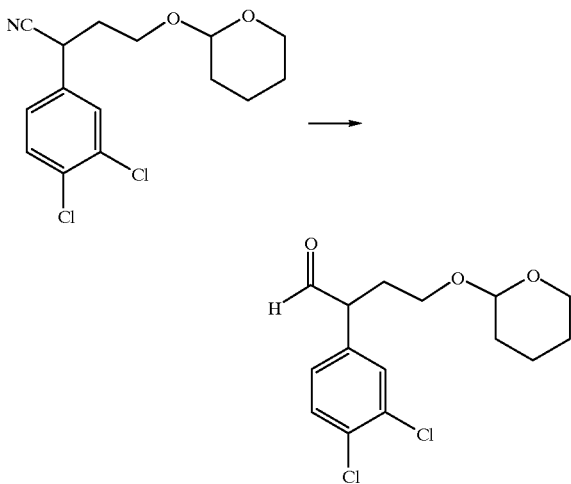

2-(3,4-Dichlorophenyl)-4-(tetrahydropyran-2-yloxy)butanenitrile (20.2 g) (see Preparation 26) was dissolved in anhydrous toluene (300 ml) and cooled to −78° C. under a nitrogen atmosphere. Diisobutylaluminium hydride (85.6 ml of a 1.0 M solution in toluene) was then added dropwise. The mixture was stirred at −78° C. for 1.5 hours and then allowed to warm slowly to −40° C. Water (100 ml) and saturated aqueous ammonium chloride solution (50 ml) were carefully added (exothermic reaction) and the mixture allowed to warm to 10° C. before further addition of water (100 ml) and saturated aqueous ammonium chloride solution (50 ml). A 10% w/w aqueous solution of Rochelle's salt (potassium sodium tartrate tetrahydrate) (400 ml) was added and the mixture extracted with diethyl ether. The organic phase was dried over anhydrous sodium sulphate and the solvent removed under reduced pressure to give a crude product. This was chromatographed on silica gel eluting with 98:2, by volume, dichloromethane:methanol to give 2-(3,4-dichlorophenyl)-4-(tetrahydropyran-2-yloxy)butan-1-al (17.02 g) as a yellow oil and as a mixture of diastereomers.

$^1$H-NMR (CDCl$_3$) (mixture of two diastereomers): δ=9.70 (1H, s), 7.44 (1H, d), 7.32 (1H, m), 7.06 (1H, m), 4.55 (0.5H, t), 4.46 (0.5H, t), 3.20–3.90 (6H, m), 2.35–2.50 (1H, m), 1.45–2.00 (6H, m) ppm.

PREPARATION 28

2-(3,4-Dichlorophenyl)-4-(tetrahydropyran-2-yloxy)butan-1-ol

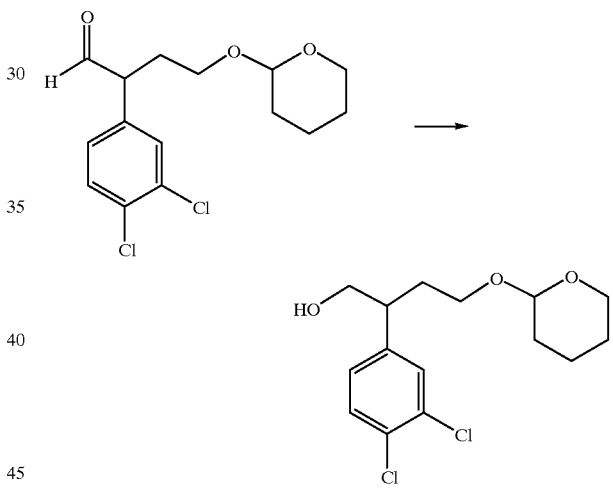

Sodium borohydride (2.03 g) was added portionwise to a solution of 2-(3,4-dichlorophenyl)-4-(tetrahydropyran-2-yloxy)butan-1-al (17.02 g) (see Preparation 27) in 2-propanol (250 ml). The mixture was stirred at room temperature overnight and glacial acetic acid (4 ml) carefully added, followed by addition of water (2 ml). The solvent was removed under reduced pressure to give a residue which was dissolved in dichloromethane and washed sequentially with water, dilute aqueous sodium hydrogen carbonate solution and brine. The solution was dried over anhydrous sodium sulphate and the solvent removed under reduced pressure. The crude product was chromatographed on silica gel eluting with 1:1, by volume, ethyl acetate:hexane to give 2-(3,4-dichlorophenyl)-4-(tetrahydropyran-2-yloxy)butan-1-ol (14.7 g) as a colourless oil and as a mixture of diastereomers.

$^1$H-NMR (CDCl$_3$) (mixture of two diastereomers): δ=7.30–7.40 (2H, m), 7.09 (1H, d), 4.55 (0.5H, t), 4.46 (0.5H, t), 3.24–3.82 (6H, m), 2.90–3.00 (1H, m), 1.45–2.10 (9H, m) ppm.

PREPARATION 29

1-Methanesulphonyloxy-2-(3,4-dichlorophenyl)-4-(tetrahydropyran-2-yloxy)butane

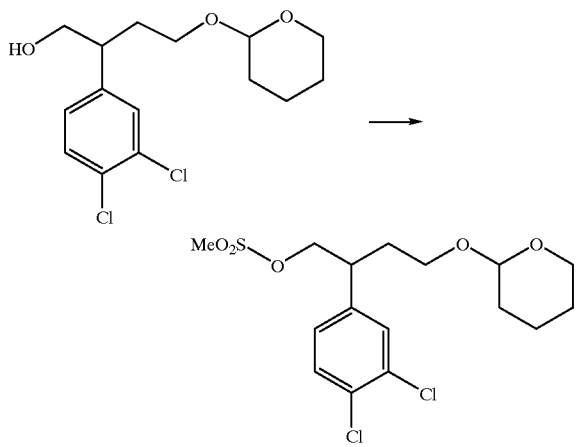

Methanesulphonyl chloride (2.4 ml) was added dropwise to an ice-cooled solution of 2-(3,4-dichlorophenyl)-4-(tetrahydropyran-2-yloxy)butan-1-ol (8.13 g) (see Preparation 28) and triethylamine (5.32 ml) in dichloromethane (100 ml) under a nitrogen atmosphere. The mixture was stirred for 10 minutes at 0° C. and then 90 minutes at room temperature before being washed twice with water. The organic phase was separated, dried over anhydrous sodium sulphate and the solvent removed under reduced pressure to give the crude product. This was chromatographed on silica gel eluting with 95:5, by volume, dichloromethane:diethyl ether to give 1-methanesulphonyloxy-2-(3,4-dichlorophenyl)-4-(tetrahydropyran-2-yloxy)butane (8.85 g) as a yellow oil and as a mixture of diastereomers.

$^1$H-NMR (CDCl$_3$) (mixture of two diastereomers): δ=7.42 (1H, d), 7.32 (1H, dd), 7.09 (1H, m), 4.30–4.50 (3H, m), 3.20–3.80 (5H, m), 2.89 (3H, s), 2.05–2.15 (1H, m), 1.50–1.95 (7H, m) ppm.

PREPARATION 30

1-(Imidazol-1-yl)-2-(3,4-dichlorophenyl)-4-(tetrahydropyran-2-yloxy)butane

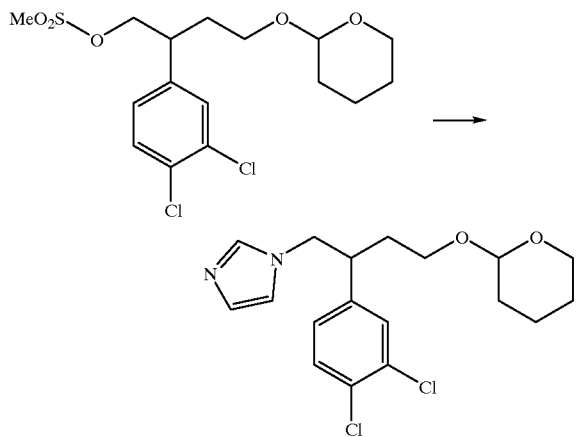

1-Methanesulphonyloxy-2-(3,4-dichlorophenyl)-4-(tetrahydropyran-2-yloxy)butane (10 g) (see Preparation 29), imidazole (2.07 g) and potassium carbonate (7.65 g) were dissolved in anhydrous acetonitrile (50 ml) and heated under reflux under a nitrogen atmosphere for 3 days. The organic solvent was then removed under reduced pressure and the resulting aqueous suspension partitioned between dichloromethane and water. The organic phase was separated, washed sequentially with water and brine, dried over anhydrous sodium sulphate and the solvent removed under reduced pressure. The crude product was chromatographed on silica gel eluting with 95:5, by volume, dichloromethane:methanol to give 1-(imidazol-1-yl)-2-(3,4-dichlorophenyl)-4-(tetrahydropyran-2-yloxy)butane (3 g) as an oil and as a mixture of diastereomers.

$^1$H-NMR (CDCl$_3$) (mixture of two diastereomers): δ=7.35 (1H, d), 7.18–7.28 (2H, m), 6.99 (1H, s), 6.88 (1H, m), 6.69 (1H, s), 4.49 (0.5H, t), 4.40 (0.5H, t), 4.00–4.25 (2H, m), 3.10–3.85 (5H, m), 1.45–2.10 (8H, m) ppm.

PREPARATION 31

3-(3,4-Dichlorophenyl)-4-[2-(3,5-dimethylbenzoyl)imidazol-1-yl]butyl 3,5-dimethylbenzoate

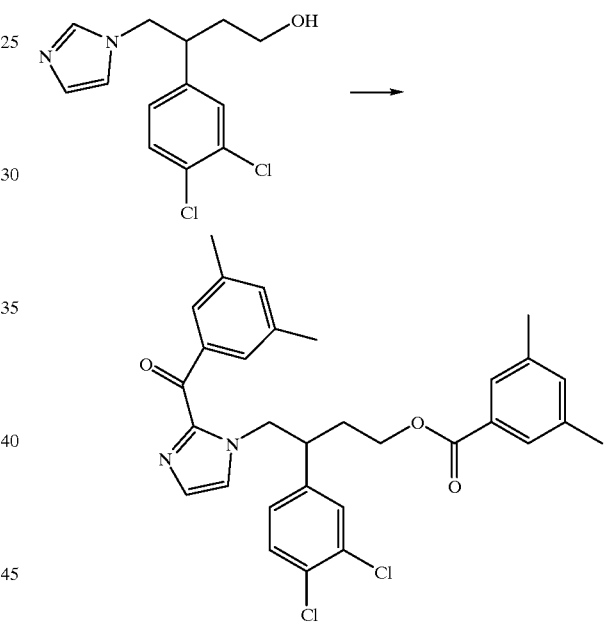

3,5-Dimethylbenzoyl chloride (1.33 g) was added dropwise to a suspension of 3-(3,4-dichlorophenyl)-4-(imidazol-1-yl)butan-1-ol (0.75 g) (see Preparation 19) and triethylamine (1.1 g) in anhydrous acetonitrile (15 ml) and the solution stirred at room temperature for 120 hours. The mixture was then mixed with water (30 ml) and dichloromethane (50 ml), the organic phase separated and washed sequentially with water and brine. The solvent was removed under reduced pressure to give a residue which was chromatographed on silica gel eluting with a solvent gradient of 100:0 changing to 99:1, by volume, dichloromethane:methanol to give 3-(3,4-dichlorophenyl)-4-[2-(3,5-dimethylbenzoyl)imidazol-1-yl]butyl 3,5-dimethylbenzoate (0.94 g) as a yellow foam.

$^1$H-NMR (CDCl$_3$): δ=7.69 (2H, s), 7.49 (2H, s), 7.10–7.27 (5H, m), 6.92 (1H, dd), 6.81 (1H, s), 4.76 (1H, dd), 4.51 (1H, dd), 4.10–4.30 (2H, m), 3.32 (1H, m), 2.35 (6H, s), 2.29 (6H, s), 2.19 (2H, m) ppm.

PREPARATION 32

2,3-Dihydrobenzo[b]furan-7-oic acid

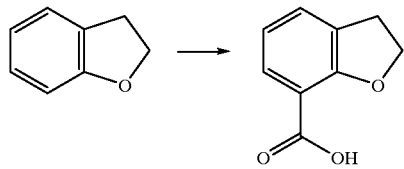

N,N,N',N'-Tetramethylethylenediamine (38 ml) was dissolved in hexane (300 ml), cooled in an ice-bath and n-butyllithium (100 ml of a 2.5M solution in hexane) added. The mixture was stirred at 0° C. for 15 minutes before adding 2,3-dihydrobenzo[b]furan (30 g) dropwise over 30 minutes. The mixture was allowed to warm to room temperature over 30 minutes, stirred at room temperature for a further 4 hours, poured onto an excess of solid carbon dioxide and left to stand for 3 days by which time the solvent had evaporated off. The residue was partitioned between ethyl acetate (1L) and 4N aqueous hydrochloric acid solution (240 ml), the layers separated and the aqueous layer extracted with ethyl acetate (500 ml). The organic extracts were combined, dried over anhydrous sodium sulphate and the solvent removed under reduced pressure. The residue was then triturated with diethyl ether to give 2,3-dihydrobenzo[b]furan-7-oic acid as a white solid (21 g)

$^1$H-NMR (CDCl$_3$): δ=7.75 (1H d), 7.31 (1H, d), 6.88 (1H, t), 4.69 (2H, t), 3.20 (2H, t) ppm.

PREPARATION 33

1,2,3,4-Tetrahydro-5-naphthoic acid

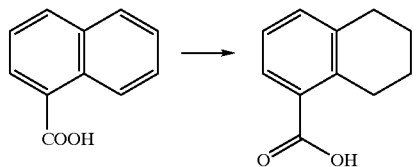

10% w/w Palladium-on-carbon (10 g) was added to a solution of 1-naphthoic acid (33.4 g) in glacial acetic acid (150 ml) and the mixture hydrogenated at 345 kPa (50 psi) and 85° C. for 4 days. The warm mixture was filtered through a short column of Arbacel (trade mark) filter aid and the pad washed with glacial acetic acid (150 ml). Water (1.5L) was added to the filtrate and the resulting precipitate filtered off and washed with water. The precipitate was dissolved in dichloromethane, the solution dried over anhydrous sodium sulphate and the solvent removed under reduced pressure to give an oil which was crystallised from ethyl acetate to give 1,2,3,4-tetrahydro-5-naphthoic acid (2.94 g) as a white solid (m.p. 148–150° C.).

$^1$H-NMR (CDCl$_3$): δ=7.85 (1H, d), 7.28 (1H, d), 7.16 (1H, m), 3.15 (2H, br. s), 2.84 (2H, br. s), 1.72–1.90 (4H, m) ppm.

PREPARATION 34

1,2,3,4-Tetrahydro-6-naphtoic acid

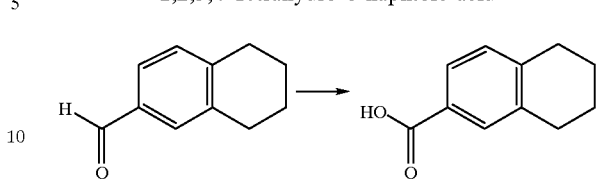

1,2,3,4-Tetrahydro-6-naphthaldehyde (2.0 g) was suspended in 0.5M aqueous sodium hydroxide solution (125 ml), stirred vigorously and a 70% w/w solution of tertiary butyl hydroperoxide in water (10.3 ml) added. The mixture was heated at about 70° C. for 4 hours and then left to stand at room temperature for 3 days. A frther quantity of a 70% w/w solution of tertiary butyl hydroperoxide in water (10 ml) was added and the mixture heated at about 70° C. for a further 24 hours. The mixture was cooled, diethyl ether (100 ml) added and the phases separated. The aqueous phase was acidified to pH 1 with 2N aqueous hydrochloric acid solution and extracted with diethyl ether (2×100 ml). The organic phases were combined, dried over anhydrous sodium sulphate and the solvent removed under reduced pressure to give a residue which was chromatographed on silica gel eluting with a solvent gradient of 1:1 changing to 1:0, by volume, diethyl ether:pentane to give 1,2,3,4-tetrahydro-6-naphthoic acid (0.62 g) as a white solid.

$^1$H-NMR (CDCl$_3$): δ=7.78–7.86 (2H, m), 7.14 (1H, d), 2.78–2.87 (4H, br. s), 1.79–1.88 (4H, br. s) ppm.

PREPARATION 35

2,3-Dihydrobenzo[b]furan-7-oyl chloride

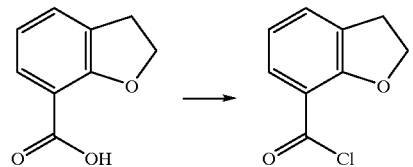

2,3-Dihydrobenzo[b]furan-7-oic acid (3 g) (see Preparation 32) was suspended in anhydrous dichloromethane (30 ml) and oxalyl chloride (3.5 g) added, followed by addition of dimethylformamide (3 drops). The mixture was stirred at room temperature for 2.5 hours, the solvent then removed under reduced pressure, the resulting residue dissolved in dichloromethane and the solvent removed under reduced pressure. The residue was again dissolved in dichloromethane and the solvent removed under reduced pressure to give 2,3-dihydrobenzo[b]furan-7-oyl chloride as a pink solid (3.3 g).

PREPARATION 36

1,2,3,4-Tetrahydro-5-naphthoyl chloride

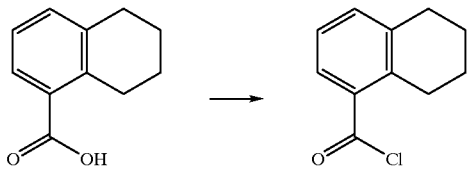

This compound was prepared by an analogous method to that used in Preparation 35 using 1,2,3,4-tetrahydro-5-naphthoic acid (see Preparation 33) as the starting material.

PREPARATION 37

1,2,3,4-Tetrahydro-6-naphthoyl chloride

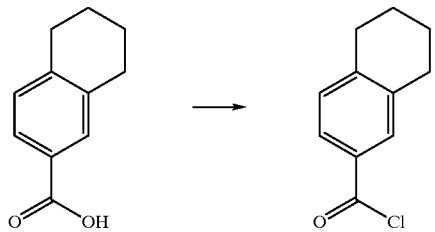

This compound was prepared by an analogous method to that used in Preparation 35 using 1,2,3,4-tetrahydro-6-naphthoic acid (see Preparation 34) as the starting material.

PREPARATIONS 38–46

The compounds of the following tabulated preparations (Table 2), of the general formula:

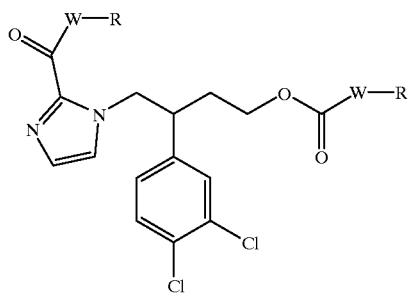

were prepared by a similar method to that of Preparation 31 using 3-(3,4-dichlorophenyl)-4-(imidazol-1-yl)butan-1-ol (see Preparation 19) and the appropriate acid chloride starting material.

TABLE 2

| Prep. no. | Acid Chloride starting material | R—W— | Analytical Data |
|---|---|---|---|
| 38 | 2,3-dimethyl-benzoyl chloride | Me, Me (2,3-dimethylphenyl) | $^1$H-NMR(CDCl$_3$): δ=7.47(1H, d), 7.33(1H, d), 7.22–7.29(3H, m), 6.96–7.15(5H, m), 6.82(1H, s), 4.83(1H, dd), 4.64(1H, dd), 4.27–4.36(1H, m), 4.09–4.20(1H, m), 3.32–3.44(1H, m), 2.41(3H, s), 2.31(6H, s), 2.15–2.25 (2H, m), 2.15(3H, s)ppm. |
| 39 | 2-trifluoro-methoxy-benzoyl chloride | CF$_3$O (2-trifluoromethoxyphenyl) | $^1$H-NMR(CDCl$_3$): δ=7.82(1H, d), 7.20–7.65(9H, m), 7.10(1H, s), 6.93 (1H, dd), 6.79(1H, s), 4.86(1H, dd), 4.53(1H, dd), 4.30–4.42(1H, m), 4.12–4.28(1H, m), 3.28–3.42(1H, m), 2.10–2.30(2H, m) ppm. |
| 40 | 2-methoxy-3-methyl-benzoyl chloride | Me, MeO (2-methoxy-3-methylphenyl) | $^1$H-NMR(CDCl$_3$): δ=7.48(1H, d), 7.24–7.36(4H, m), 7.18(1H, d), 6.95–7.09(4H, m), 6.80(1H, s), 4.86(1H, dd), 4.56(1H, dd), 4.27–4.36(1H, m), 4.10–4.22(1H, m), 3.76(3H, s), 3.66 (3H, s), 3.31–3.43(1H, m), 2.30(3H, s), 2.28(3H, s), 2.08–2.18(2H, m)ppm. |

TABLE 2-continued

| Prep. no. | Acid Chloride starting material | R—W— | Analytical Data |
|---|---|---|---|
| 41 | See Prep. no. 35 | 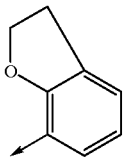 | ¹H-NMR(CDCl₃): δ=7.58(1H, d), 7.50(1H, d), 7.20–7.36(4H, m), 7.08 (1H, s), 6.98(1H, d), 6.72–6.90(3H, m), 4.50–4.81(6H, m), 4.27–4.38(1H, m), 4.03–4.15(1H, m), 3.35–3.49(1H, m), 3.05–3.28(4H, m), 2.04–2.23(2H, m), ppm. |
| 42 (footnote (a)) | 2-naphthoyl chloride | 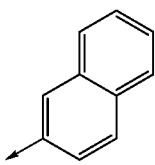 | ¹H-NMR(CDCl₃): δ=8.82(1H, s), 8.46(1H, s), 8.15(1H, d), 7.74–7.99 (8H, m), 7.43–7.64(4H, m), 7.26(1H, s), 7.17(1H, s), 6.98(1H, d), 6.86(1H, s), 4.89(1H, dd), 4.58(1H, dd), 4.39–4.48(1H, m), 4.25–4.30(1H, m), 3.42–3.52(1H, m), 2.20–2.38(2H, m)ppm. |
| 43 (footnote (b)) | 3-trifluoro-methyl-4-fluoro-benzoyl chloride | 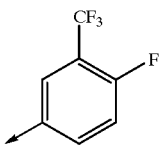 | ¹H-NMR(CDCl₃): δ=8.49–8.62(2H, m), 8.20(1H, d), 8.04–8.09(1H, m), 7.12–7.32(5H, m), 6.90(1H, d), 6.82 (1H, s), 4.81(1H, dd), 4.26–4.51(3H, m), 3.29–3.40(1H, m), 2.20–2.29(2H, m)ppm. |
| 44 (footnote (a)) | See Prep. No. 36 | 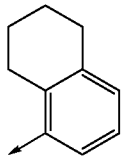 | ¹H-NMR(CDCl₃): δ=7.50(1H, d), 6.95–7.38(10H, m), 4.83(1H, dd), 4.63 (1H, m), 4.30–4.35(1H, m), 4.08–4.16 (1H, m), 3.30–3.40(1H, m), 3.00(2H, br. s), 2.63–2.84(6H, m), 2.10–2.25(2H, m), 1.67–1.83(8H, m)ppm. |
| 45 (footnote (c)) | See Prep. No. 37 | 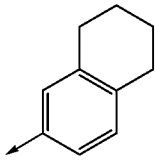 | ¹H-NMR(CDCl₃): δ=7.79–7.88(2H, m), 7.52–7.62(2H, m), 7.01–7.34(5H, m), 6.90(1H, dd), 6.79(1H, s), 4.76 (1H, dd), 4.51(1H, dd), 4.10–4.32(2H, m), 3.27–3.40(1H, m), 2.68–2.91(8H, m), 2.11–2.26(2H, m), 1.72–1.91(8H, m)ppm. |
| 46 | 2-methoxy-5-chloro-benzoyl chloride | 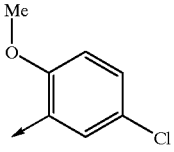 | ¹H-NMR(CDCl₃): δ=7.62(1H, s), 7.32–7.43(4H, m), 7.24(1H, s), 7.07 (1H, s), 7.02(1H, dd), 6.90(2H, t), 6.77 (1H, s), 4.87(1H, dd), 4.49(1H, dd), 4.30–4.35(1H, m), 4.11–4.20(1H, m), 3.86(3H, s), 3.72(3H, s), 3.32–3.41 (1H, m), 2.10–2.25(2H, m)ppm. |

Footnotes
(a) chromatographed on silica gel eluting with a solvent gradient of 1:2 changing to 1:0, by volume, ethyl acetate:pentane.
(b) chromatographed on silica gel eluting with diethyl ether.
(c) chromatographed on silica gel eluting with a solvent gradient of 1:2 changing to 2:1, by volume, ethyl acetate:pentane.

PREPARATION 47

3-(3,4-Dichlorophenyl)-4-[2-(3,5-dimethylbenzoyl)imidazol-1-yl]butan-1-ol

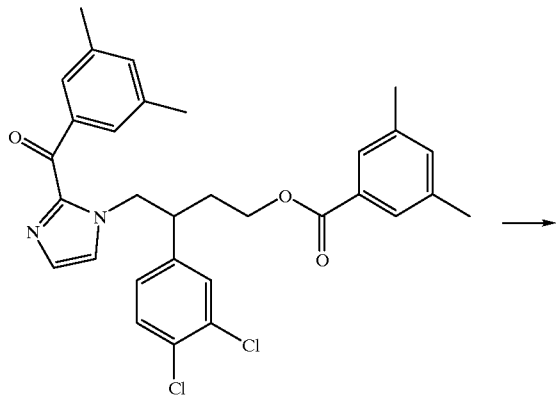

3-(3,4-Dichlorophenyl)-4-[2-(3,5-dimethylbenzoyl)imidazol-1-yl]butyl 3,5-dimethylbenzoate (0.93 g) (see Preparation 31) was dissolved in methanol (10 ml) and 2N aqueous sodium hydroxide solution (2 ml) added. A thick gum formed, additional methanol was added (50 ml) and the resulting suspension sired at room temperature overnight. The methanol was then removed under reduced pressure and the residue partitioned between dichloromethane (50 ml) and water (10 ml). The organic phase was separated, washed with brine and the solvent removed under reduced pressure to give the crude product which was chromatographed on silica gel eluting with a solvent gradient of 99:1 changing to 95:5, by volume, dichloromethane:methanol, to give 3-(3,4-dichlorophenyl)-4-[2-(3,5-dimethylbenzoyl)imidazol-1-yl]butan-1-ol (0.67 g) as a white foam.

$^1$H-NMR (CDCl$_3$): δ=7.70 (2H, s), 7.10–7.32 (4H, m), 6.89 (1H, d), 6.72 (1H, s), 4.83 (1H, dd), 4.40 (1H, dd), 3.70–3.80 (1H, m), 3.50–3.62 (1H, m), 3.28–3.40 (1H, m), 2.40 (6H, s), 1.85–2.07 (3H, m), ppm.

PREPARATIONS 48–53

The compounds of the following tabulated preparations (Table 3) of the general formula:

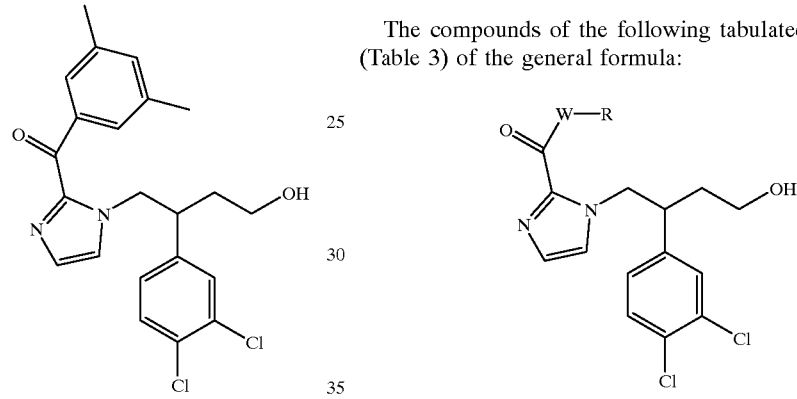

were prepared by a similar method to that of Preparation 47 using the appropriate starting materials (see Preparations 38–41, 44 and 46).

TABLE 3

| Prep. no. | Starting material Prep. No. | R—W— | Analytical Data |
|---|---|---|---|
| 48 | 38 | 2,3-dimethylphenyl (Me, Me substituents) | $^1$H-NMR(CDCl$_3$): δ=7.31(1H, d), 7.10–7.28(4H, m), 7.06(1H, s), 6.92(1H, dd), 6.75(1H, s), 4.90(1H, dd), 4.50(1H, dd), 4.70–4.81(1H, m), 3.50–3.64(1H, m), 3.30–3.43(1H, m), 2.29(3H, s), 2.18(3H, s), 1.90–2.05(2H, m), 1.80(1H, t)ppm. |
| 49 | 39 | 2-(trifluoromethoxy)phenyl (CF$_3$O substituent) | $^1$H-NMR(CDCl$_3$): δ=7.20–7.64(6H, m), 7.09(1H, s), 6.91(1H, d), 6.72(1H, s), 4.96(1H, dd), 4.39(1H, dd), 3.69–3.83 (1H, m), 3.51–3.67(1H, m), 3.28–3.41 (1H, m), 1.87–2.08(2H, m), 1.74(1H, t) ppm. |
| 50 | 40 | 2-methoxy-3-methylphenyl (Me, Me substituents with O) | $^1$H-NMR(CDCl$_3$): δ=7.18–7.37(4H, m), 7.05–7.10(2H, m), 6.93(1H, dd), 6.72 (1H, s), 4.92(1H, dd), 4.42(1H, dd), 3.75 (1H, m), 3.70(3H, s), 3.50–3.62(1H, m), 3.31–3.45(1H, m), 2.32(3H, s), 1.86–2.02 (3H, m)ppm. |

TABLE 3-continued

| Prep. no. | Starting material Prep. No. | R—W— | Analytical Data |
|---|---|---|---|
| 51 | 41 | (2,3-dihydrobenzofuran-7-yl) | ¹H-NMR(CDCl₃): δ=7.64(1H, d), 7.11–7.38(3H, m), 7.06(1H, s), 6.85–6.96(2H, m), 6.67(1H, s), 4.89(1H, dd), 4.60–4.75 (2H, m), 4.35(1H, dd), 3.63–3.75(1H, m), 3.49–3.61(1H, m), 3.18–3.41(3H, m), 1.84–2.06(2H, m), 1.72(1H, t)ppm. |
| 52 | 44 | (5,6,7,8-tetrahydronaphthalen-1-yl) | ¹H-NMR(CDCl₃): δ=7.10–7.35(5H, m), 7.06(1H, s), 6.92(1H, dd), 6.74(1H, s), 4.90(1H, dd), 4.50(1H, dd), 3.70–3.82 (1H, m), 3.53–3.64(1H, m), 3.30–3.42 (1H, m), 2.70–2.86(4H, m), 1.70–2.04 (6H, m)ppm. |
| 53 | 46 | (4-methoxy-3-chlorophenyl) | ¹H-NMR(CDCl₃): δ=7.30–7.42(3H, m), 7.19(1H, s), 7.03(1H, s), 6.92(2H, t), 6.69(1H, s), 4.91(1H, dd), 4.35(1H, dd), 3.50–3.80(4H, m), 3.50–3.63(1H, m), 3.29–3.40(1H, m), 1.89–2.01(2H, m), 1.72(1H, t)ppm. |

PREPARATION 54

3-(3,4-Dichlorophenyl)-4-[2-(2-naphthoyl)imidazol-1-yl]butan-1-ol

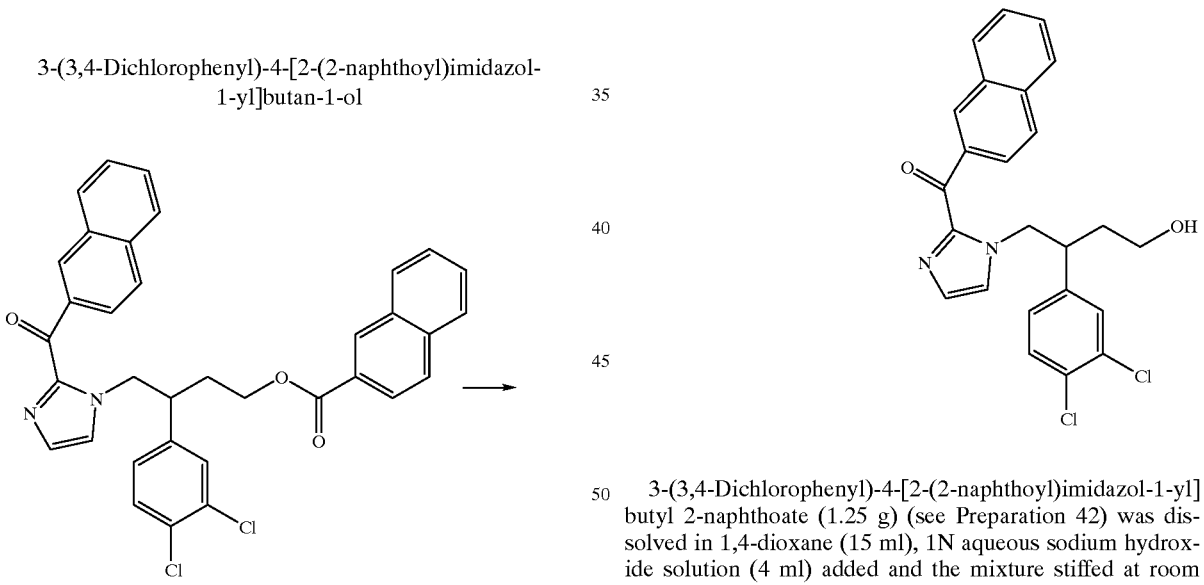

3-(3,4-Dichlorophenyl)-4-[2-(2-naphthoyl)imidazol-1-yl] butyl 2-naphthoate (1.25 g) (see Preparation 42) was dissolved in 1,4-dioxane (15 ml), 1N aqueous sodium hydroxide solution (4 ml) added and the mixture stiffed at room temperature overnight. The dioxane was then removed

59 under reduced pressure and the residue partitioned between ethyl acetate and water. The organic phase was separated, washed sequentially with 1N aqueous sodium hydroxide solution, water and brine and the solvent removed under reduced pressure to give the crude product which was chromatographed on silica gel eluting with a solvent gradient of 99:1 changing to 95:5, by volume, dichloromethane:methanol, to give 3-(3,4-dichlorophenyl)-4-[2-(2-naphthoyl)imidazol-1-yl]butan-1-ol (0.8 g) as a gum.

$^1$H-NMR (CDCl$_3$): δ=8.82 (1H, s), 8.16 (1H, d), 7.99 (1H, d), 7.89 (2H, t), 7.50–7.63 (2H, m), 7.26 (1H, d), 7.16 (1H, d), 6.90 (1H, dd), 6.76 (1H, s), 4.90 (1H, dd), 4.43 (1H, dd), 3.69–3.83 (1H, m), 3.51–3.68 (1H, m), 3.32–3.45 (1H, m), 1.86–2.08 (3H, m) ppm.

PREPARATIONS 55–56

The compounds of the following tabulated preparations (Table 4) of the general formula:

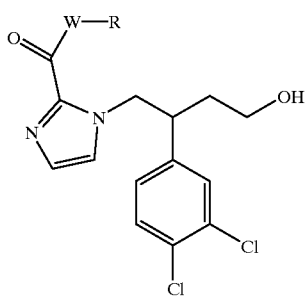

were prepared by a similar method to that of Preparation 54 using the appropriate starting material compounds (see Preparations 43 and 45).

60

PREPARATION 57

1-[2-(2-Methoxybenzoyl)imidazol-1-yl]-2-(3,4-dichlorophenyl-4-(tetrahydropyran-2-yloxy)butane

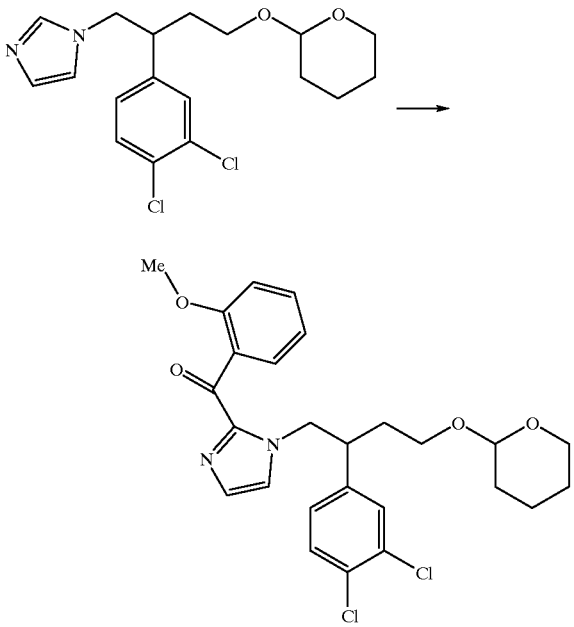

1(Imidazol-1-yl)-2-(3,4-dichlorophenyl)-4-tetrahydropyran-2-yloxy)butane (0.86 g) (see Preparation 30) and triethylamine (1.3 ml) were dissolved in acetonitrile (15 ml), under a nitrogen atmosphere, the solution cooled in an ice-bath and 2-methoxybenzoyl chloride (1.4 ml) added, dropwise. The mixture was allowed to warm to room temperature slowly and then stirred for 2 days. The acetonitrile was removed under reduced pressure and the residue dissolved in dichloromethane (20 ml) and washed sequen-

TABLE 4

| Prep. no. | Starting material Prep. No. | R | Analytical Data |
|---|---|---|---|
| 55 (footnote (a)) | 43 | 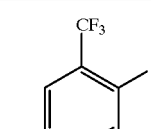 | $^1$H-NMR(CDCl$_3$): δ=8.49–8.62(2H, m), 7.23–7.32(2H, m), 7.11(2H, s), 6.86 (1H, d), 6.80(1H, s), 4.85(1H, dd), 4.47 (1H, dd), 3.70–3.81(1H, m), 3.52–3.63 (1H, m), 3.29–3.39(1H, m), 1.89–2.09 (2H, m), 1.71(1H, br. s)ppm. |
| 56 | 45 | 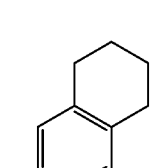 | $^1$H-NMR(CDCl$_3$): δ=7.81–7.91(2H, m), 7.05–7.32(4H, m), 6.88(1H, dd), 6.71 (1H, s), 4.85(1H, dd), 4.37(1H, dd), 3.69–3.80(1H, m), 3.51–3.66(1H, m), 3.07–3.42(1H, m), 2.70–2.92(4H, m), 1.76–2.05(6H, m)ppm. | tially with water and brine. The organic phase was then dried over anhydrous sodium sulphate and the solvent removed under reduced pressure to give a residue which was chromatographed on silica gel eluting with 97:3, by volume, dichloromethane:methanol to give 1-[2-(2-methoxybenzoyl) imidazol-1-yl]-2-(3,4-dichlorophenyl)-4-(tetrahydropyran-2-yloxy)butane (1.1 g) as an oil and as a mixture of diastereomers.

$^1$H-NMR (CDCl$_3$) (mixture of two diastereomers): δ=6.76–7.52 (9H, m), 4.10–4.90 (3H, m), 3.11–3.90 (8H, m), 1.45–2.25 (6H, m), 1.26 (1H, t), 1.06 (1H, t)ppm.

PREPARATIONS 58–62

The compounds of the following tabulated preparations (Table 5) of the general formula:

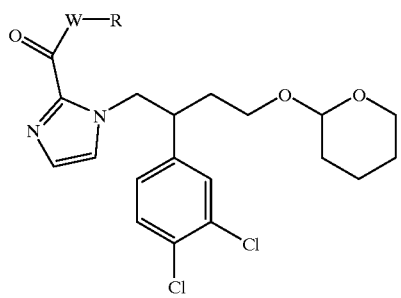

were prepared by a similar method to that of Preparation 57 using the appropriate starting materials.

TABLE 5

| Prep. no. | Acid Chloride Starting material | R—W— | Analytical Data |
|---|---|---|---|
| 58 | 3,5-bis(tri-fluoro-methyl)-benzoyl chloride | 3,5-bis(trifluoromethyl)phenyl | $^1$H-NMR(CDCl$_3$)(mixture of two diastereomers): δ=8.71(2H, d), 8.06 (1H, s), 7.13–7.32(3H, m), 6.98(1H, d), 6.85–6.95(1H, m), 4.40–4.80(3H, m), 3.60–3.85(2H, m), 3.20–3.50(3H, m), 1.43–2.18(8H, m)ppm. |
| 59 | 2-trifluoro-methyl-benzoyl chloride | 2-trifluoromethylphenyl | $^1$H-NMR(CDCl$_3$)(mixture of two diastereomers): δ=7.75(1H, dd), 7.60 (2H, m), 7.43(2H, m), 7.24(1H, t), 7.09 (1H, s), 6.97(1H, m), 6.86(1H, d), 4.80–4.90(1H, m), 4.40–4.64(2H, m), 3.55–3.83(2H, m), 3.20–3.50(3H, m), 1.90–2.18(2H, m), 1.43–1.86(6H, m)ppm. |
| 60 | 2-isoprop-oxy-benzoyl chloride | 2-isopropoxyphenyl | $^1$H-NMR(CDCl$_3$)(mixture of two diastereomers): δ=6.75–7.58(9H, m), 4.38–4.91(4H, m), 3.20–3.80(5H, m), 1.15–2.13(14H, m)ppm. |
| 61 | 2-ethyl-benzoyl chloride | 2-ethylphenyl | $^1$H-NMR(CDCl$_3$)(mixture of two diastereomers): δ=6.87–7.43(9H, m), 4.40–4.83(3H, m), 3.20–3.82(5H, m), 2.62–2.75(2H, m), 1.10–2.10(11H, m) ppm. |
| 62 | 2-phenoxy-benzoyl chloride | 2-phenoxyphenyl | $^1$H-NMR(CDCl$_3$)(mixture of two diastereomers): δ=6.90–7.52(12H, m), 6.84(1H, d), 6.67(1H, d), 4.69–4.80(1H, m), 4.29–4.48(2H, m), 3.12–3.79(5H, m), 1.41–2.08(8H, m)ppm. |

PREPARATION 63

1-Ethoxymethylimidazole

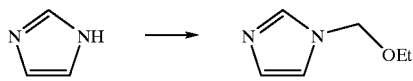

Imidazole (20 g) was dissolved in tetrahydrofuran (700 ml) under a nitrogen atmosphere, cooled to −70° C. and n-butyllithium (117.5 ml of a 2.5M solution in hexane) added dropwise, over 15 minutes. The mixture was allowed to warm to −20° C. and stirred at −20° C. for 30 minutes before the dropwise addition of chloromethyl ethyl ether (30.5 g). The mixture was allowed to warm to room temperature and stirred for a further hour. The solvent was removed under reduced pressure to give a residue which was triturated with dichloromethane and filtered through a short pad of Arbacel (trade mark) filter aid. The solvent was removed from the filtrate under reduced pressure to give a mobile oil which was distilled under reduced pressure (0.7 millibars, 0.53 mmHg) to give 1-ethoxymethylimidazole (20.8 g) as an oil.

$^1$H-NMR (CDCl$_3$): δ=7.61 (1H, s), 7.09 (2H, d), 5.29 (2H, s), 3.49 (2H, q), 1.21 (3H, t) ppm.

PREPARATION 64

1-Ethoxymethyl-2-phenacetylimidazole

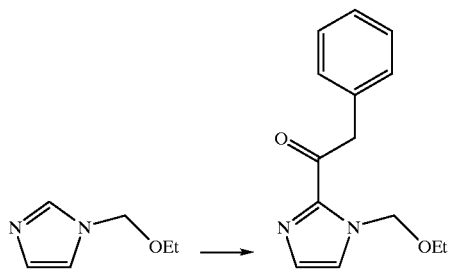

1-Ethoxymethylimidazole (11.98 g) (see Preparation 63) was dissolved in tetrahydrofuran (400 ml) under a nitrogen atmosphere, cooled to −70° C. and n-butyl lithium (40 ml of a 2.5M solution in hexane) added, dropwise, over 5 minutes. The mixture was stirred at −70° C. for 1 hour and chlorotrimethylsilane (10.83 g) added, dropwise. The mixture was stirred at −70° C. for 1 hour before being allowed to warm to room temperature and stirred for a further 3 hours. Phenacetyl chloride (14.68 g) was added and stirring continued for 18 hours before removing the solvent under reduced pressure. The resulting residue was dissolved in dichloromethane and washed sequentially with water, saturated aqueous sodium hydrogen carbonate solution and brine before drying over anhydrous sodium sulphate. The solvent was removed from the organic phase under reduced pressure. The crude product was chromatographed on silica gel eluting with 95:5, by volume, dichloromethane:methanol to give 1-ethoxymethyl-2-phenacetylimidazole (8.23 g) as an oil.

$^1$H-NMR (CDCl$_3$): δ=7.19–7.39 (7H, m), 5.72 (2H, s), 4.43 (2H, s), 3.48 (2H, q), 1.14 (3H, t) ppm.

PREPARATION 65

2-Phenacetylimidazole

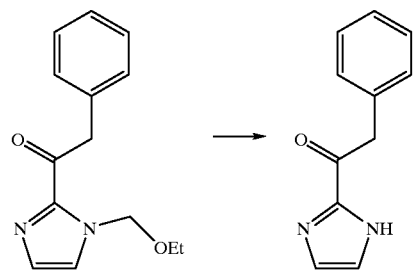

1-Ethoxymethyl-2-phenylacetylimidazole (8.23 g) (see Preparation 64) was dissolved in ethanol (200 ml), 2N aqueous hydrochloric acid solution (200 ml) added and the resulting suspension heated under reflux for 30 minutes. A further quantity of ethanol (50 ml) was added to dissolve the remaining suspended material and the mixture heated under reflux for a further 6 hours before being left to stand at room temperature overnight. The organic solvent was removed under reduced pressure and the resulting aqueous suspension basified to pH 9 by addition of a saturated aqueous sodium hydrogen carbonate solution. The mixture was then extracted (three times) with dichloromethane. The organic extracts were combined, dried over anhydrous sodium sulphate and the solvent removed under reduced pressure to give 2-phenacetylimidazole (6.29 g) as a yellow solid.

$^1$H-NMR (CDCl$_3$): δ=7.19–7.39 (7H, m), 4.40 (2H, s) ppm.

PREPARATION 66

1-[2-Phenacetylimidazol-1-yl]-2-(3,4-dichlorophenyl)-4-(tetrahydropyran-2-yloxy)butane

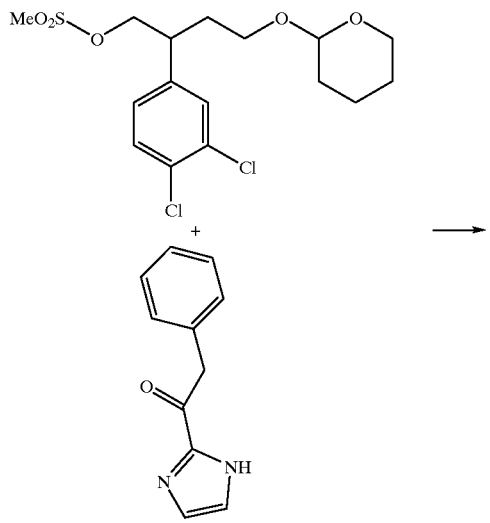

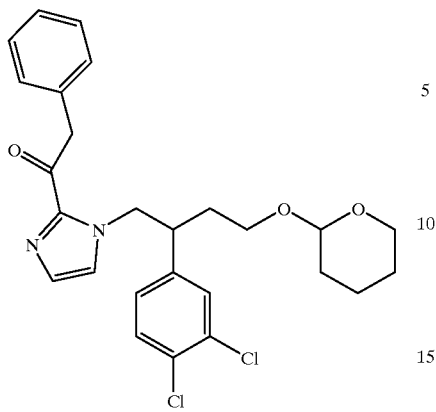

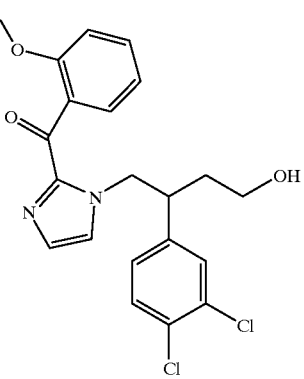

1-Methanesulphonyloxy-2-(3,4-dichlorophenyl)-4-(tetrahydropyran-2-yloxy)butane (0.57 g) (see Preparation 29) and 2-phenacetylimidazole (0.27 g) (see Preparation 65) were dissolved in acetonitrile (20 ml). Potassium carbonate (0.41 g) was added and the mixture heated under reflux, under a nitrogen atmosphere, for 18 hours. The mixture was cooled, the solvent removed under reduced pressure and the residue partitioned between dichloromethane and water. The organic phase was separated, washed with brine, dried over anhydrous sodium sulphate and the solvent removed under reduced pressure. The resulting residue was then chromatographed on silica gel eluting with 99:1, by volume, dichloromethane:methanol to give 1-[2-phenacetylimidazol-1-yl]-2-(3,4-dichlorophenyl)-4-(tetrahydropyran-2-yloxy)butane (0.23 g) as an oil and as a mixture of diastereomers.

$^1$H-NMR (CDCl$_3$) (mixture of two diastereomers): δ=7.22–7.38 (6H, m), 7.05–7.12 (2H, m), 6.71–6.84 (2H, m), 4.64–4.76 (1H, m), 4.28–4.50 (4H, m), 3.10–3.79 (5H, m), 1.42–2.05 (8H, m) ppm.

1-[2-(2-Methoxybenzoyl)imidazol-1-yl]-2-(3,4-dichlorophenyl)-4-(tetrahydropyran-2-yloxy)butane (1.1 g) (see Preparation 57) was dissolved in methanol (20 ml), Amberlyst 15 (trade mark) ion-exchange resin (0.11 g) added and the mixture stirred at room temperature for 5 days. The resin was removed by filtration through a short column of Arbacel (trade mark) filter aid and the solvent removed from the filtrate under reduced pressure to give a residue. This was chromatographed on silica gel eluting with 97:3, by volume, dichloromethane:methanol to give 3-(3,4-dichlorophenyl)-4-[2-(2-methoxybenzoyl)-imidazol-1-yl] butan-1-ol (0.31 g) as a white foam.

$^1$H-NMR (CDCl$_3$): δ=7.19–7.48 (4H, m), 6.91–7.06 (4H, m), 6.67 (1H, s), 4.93 (1H, dd), 4.36 (1H, dd), 3.52–3.80 (2H, m), 3.80 (3H, s), 3.30–3.41 (1H, m), 1.90–2.03 (2H, m), 1.72 (1H, br. s) ppm.

PREPARATION 67

3-(3,4-Dichlorophenyl)-4-[2-(2-methoxybenzoyl)imidazol-1-yl]butan-1-ol

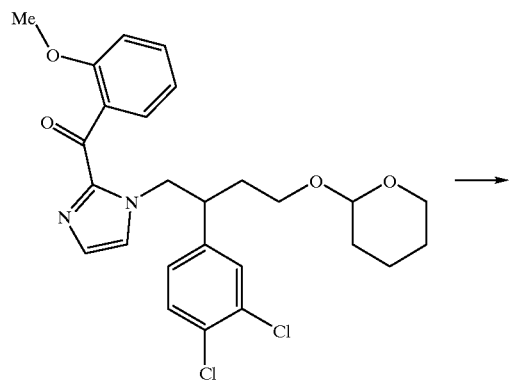

PREPARATION 68

3-(3,4-Dichlorophenyl)-4-[2-[3,5-bis(trifluoromethyl)benzoyl]imidazol-1-yl]-butan-1-ol

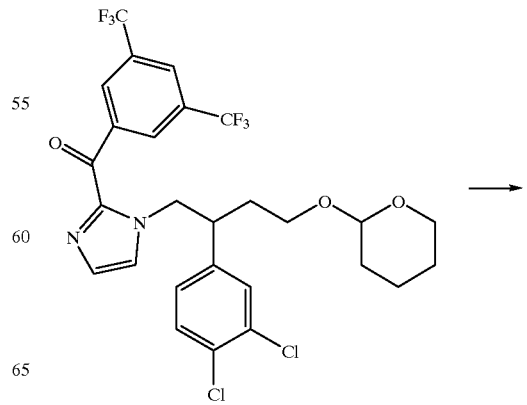

-continued

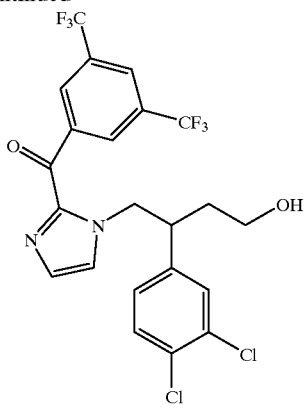

3-(3,4-Dichlorophenyl)-4-[2-[3,5-bis(trifluoromethyl)benzoyl]imidazol-1-yl]butan-1-ol was prepared in an analogous fashion to the compound of Preparation 67 using the compound of Preparation 58 as the starting material.

¹H-NMR (CDCl₃): δ=8.76 (2H, s), 8.08 (1H, s), 7.30 (1H, d), 7.19 (2H, d), 6.85–6.92 (2H, m), 4.88 (1H, dd), 4.50 (1H, dd), 3.71–3.81 (1H, m), 3.51–3.63 (1H, m), 3.30–3.42 (1H, m), 1.90–2.10 (2H, m), 1.71 (1H, t) ppm.

PREPARATION 69

3-(3,4-Dichlorophenyl)-4-[2-(2-trifluoromethylbenzoyl)imidazol-1-yl]butan-1-ol

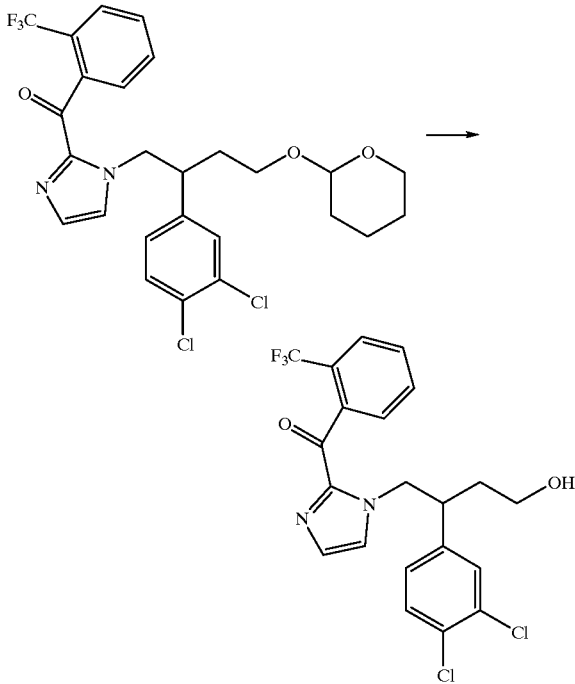

1-[2-(2-Trifluoromethylbenzoyl)imidazol-1-yl]-2-(3,4-dichlorophenyl)-4-(tetrahydropyran-2-yloxy)butane (0.68 g) (see Preparation 59) was dissolved in methanol (15 ml), which had been previously saturated with hydrogen chloride gas, and left to stand for 4 hours. The solvent was then removed under reduced pressure to give a residue which was partitioned between dichloromethane and saturated aqueous sodium hydrogen carbonate solution (the pH of the aqueous layer was kept at 8–9). The organic phase was separated and the aqueous phase extracted (twice) with dichloromethane. The organic phases were then combined, dried over anhydrous sodium sulphate and the solvent removed under reduced pressure to give 3-(3,4-dichlorophenyl)-4-[2-(2-trifluoromethylbenzoyl)imidazol-1-yl]butan-1-ol (0.41 g) as a white foam.

¹H-NMR (CDCl₃): δ=7.77 (1H, d), 7.54–7.69 (2H, m), 7.47 (1H, m), 7.32 (1H, d), 7.22 (1H, d), 7.07 (1H, s), 6.91 (1H, dd), 6.74 (1H, s), 4.98 (1H, dd), 4.42 (1H, dd), 3.70–3.81 (1H, m), 3.52–3.67 (1H, m), 3.28–3.41 (1H, m), 1.90–2.09 (2H, m), 1.77 (1H, br. s) ppm.

PREPARATIONS 70–73

The compounds of the following tabulated preparations (Table 6) of the general formula:

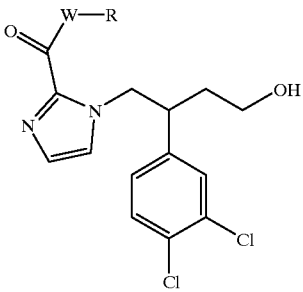

were prepared by a similar method to that of Preparation 69 using the appropriate tetrahydropyranyl protected starting materials (see Preparations 60–62 and 66)

TABLE 6

| Prep. no. | Starting material Prep. no. | R—W— | Analytical Data |
|---|---|---|---|
| 70 (footnote (a)) | 60 | 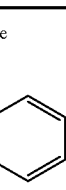 | $^1$H-NMR(CDCl$_3$): δ=7.31–7.46(3H, m), 7.24(1H, d), 6.91–7.04(4H, m), 6.85 (1H, s), 4.95(1H, dd), 4.55(1H, q), 4.30 (1H, dd), 3.71–3.83(1H, m), 3.52–3.66 (1H, m), 3.31–3.44(1H, m), 1.90–2.05 (2H, m), 1.22(6H, d)ppm. |
| 71 (footnote (a)) | 61 | 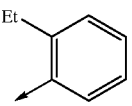 | $^1$H-NMR(CDCl$_3$): δ=7.19–7.47(6H, m), 7.09(1H, s), 6.91(1H, dd), 6.76(1H, s), 4.91(1H, dd), 4.51(1H, dd), 3.71–3.84 (1H, m), 3.52–3.66(1H, m), 3.30–3.44 (1H, m), 2.70(2H, q), 1.90–2.09(2H, m), 1.86(1H, br. s), 1.24(3H, t)ppm. |
| 72 | 62 | 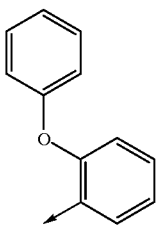 | $^1$H-NMR(CDCl$_3$): δ=6.90–7.59(12H, m), 6.79(1H, dd), 6.56(1H, s), 4.86(1H, dd), 4.17(1H, dd), 3.62–3.76(1H, m), 3.48–3.59(1H, m), 3.15–3.27(1H, m), 1.82–1.95(2H, m), 1.76(1H, br. t)ppm. |
| 73 | 66 | 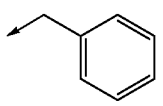 | $^1$H-NMR(CDCl$_3$): δ=7.22–7.38(6H, m), 7.04–7.10(2H, m), 6.76(1H, dd), 6.64 (1H, s), 4.81(1H, dd), 4.40(2H, dd), 4.21 (1H, dd), 3.60–3.70(1H, m), 3.44–3.55 (1H, m), 3.10–3.21(1H, m), 1.80–1.91 (2H, m), 1.67(1H, t)ppm. |

Footnote
(a) The product was purified by chromatography on silica gel eluting with 98:2, by volume, dichloromethane:methanol.

PREPARATION 74

1-Methanesulphonyloxy-3-(3,4-dichlorophenyl)-4-[2-(3,5-dimethylbenzoyl)imidazol-1-yl]butane

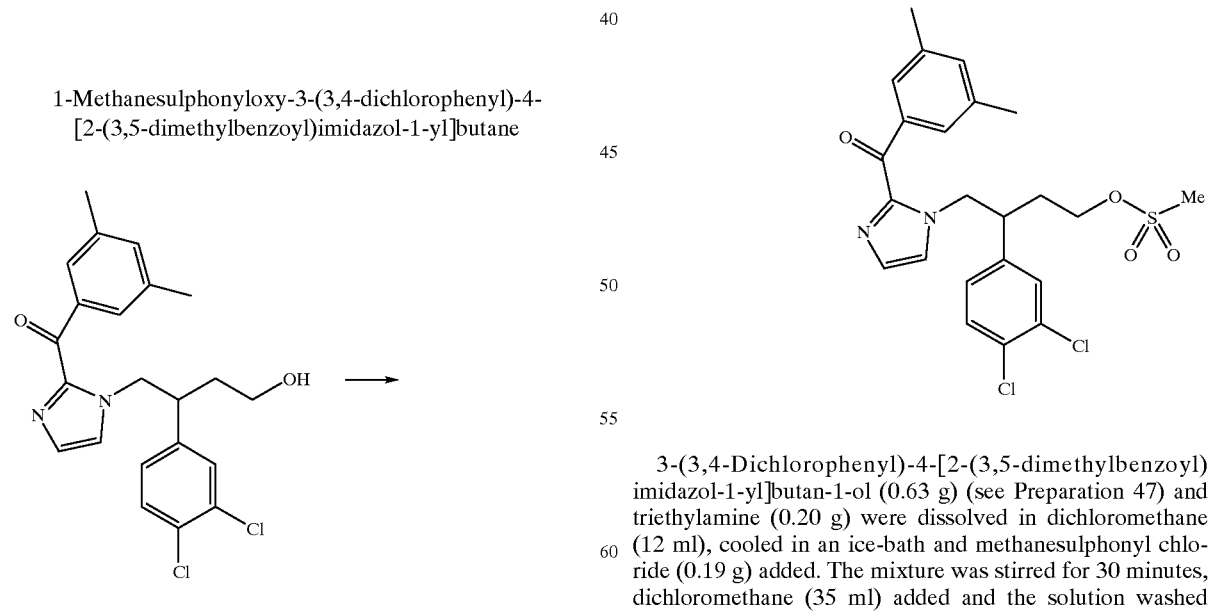

3-(3,4-Dichlorophenyl)-4-[2-(3,5-dimethylbenzoyl) imidazol-1-yl]butan-1-ol (0.63 g) (see Preparation 47) and triethylamine (0.20 g) were dissolved in dichloromethane (12 ml), cooled in an ice-bath and methanesulphonyl chloride (0.19 g) added. The mixture was stirred for 30 minutes, dichloromethane (35 ml) added and the solution washed sequentially with water (2×30 ml) and brine (30 ml). The organic phase was dried over anhydrous sodium sulphate and the solvent removed under reduced pressure. The residue was dissolved in acetonitrile and the solvent removed under reduced pressure to give 1-methanesulphonyloxy-3-(3,4-dichlorophenyl)-4-[2-(3,5-dimethylbenzoyl)imidazol-1-yl]-butane (0.72 g) as an oil.

$^1$H-NMR (CDCl$_3$): δ=7.68 (2H, s), 7.10–7.32 (4H, m), 6.91 (1H, dd), 6.83 (1H, s), 4.73 (1H, dd), 4.53 (1H, dd), 4.15–4.24 (1H, m), 4.00–4.10 (1H, m), 3.26–3.36 (1H, m), 2.92 (3H, s), 2.40 (6H, s), 2.05–2.28 (2H, m) ppm.

PREPARATIONS 75–90

The compounds of the following tabulated preparations (Table 7) of the general formula:

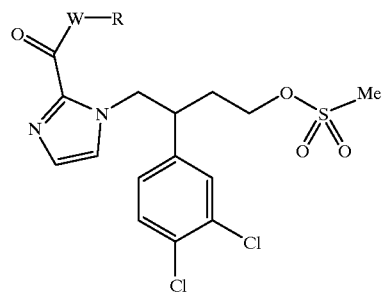

were prepared by a similar method to that of Preparation 74 using the appropriate alcohol starting material (see Preparations 48–56 and 67–73).

TABLE 7

| Prep. no. | Starting material Prep. No. | R | Analytical Data |
|---|---|---|---|
| 75 | 48 | 2,3-dimethylphenyl | $^1$H-NMR(CDCl$_3$): δ=7.38(1H, d), 7.21–7.29(2H, m), 7.15(2H, d), 7.09(1H, s), 6.98(1H, d), 6.84(1H, s), 4.82(1H, dd), 4.65(1H, dd), 4.20–4.28(1H, m), 4.02–4.11(1H, m), 3.30–3.43(1H, m), 2.96 (3H, s), 2.31(3H, s), 2.08–2.28(2H, m), 2.19(3H, s)ppm. |
| 76 | 49 | 2-(trifluoromethoxy)phenyl | $^1$H-NMR(CDCl$_3$): δ=7.50–7.60(2H, m), 7.31–7.44(3H, m), 7.26(1H, dd), 7.10 (1H, s), 6.95(1H, dd), 6.79(1H, s), 4.89 (1H, dd), 4.48(1H, dd), 4.20–4.28(1H, m), 4.03–4.11(1H, m), 3.28–3.39(1H, m), 2.05–2.30(2H, m), 1.98(3H, s)ppm. |
| 77 | 50 | 2-methoxy-3-methylphenyl | $^1$H-NMR(CDCl$_3$): δ=7.17–7.41(4H, m), 6.96–7.11(3H, m), 6.80(1H, s), 4.86 (1H, dd), 4.52(1H, dd), 4.20–4.29(1H, m), 4.02–4.11(1H, m), 3.70(3H, s), 3.30–3.44(1H, m), 2.95(3H, s), 2.31(3H, s), 2.05–2.29(2H, m)ppm. |
| 78 | 51 | 2,3-dihydrobenzofuran-7-yl | $^1$H-NMR(CDCl$_3$): δ=7.64(1H, d), 7.20–7.39(3H, m), 7.09(1H, s), 6.86–6.99(2H, m), 6.72(1H, s), 4.63–4.85(3H, m), 4.45 (1H, dd), 4.12–4.23(1H, m), 4.00–4.09 (1H, m), 3.20–3.40(3H, m), 2.93(3H, s), 2.02–2.18(2H, m)ppm. |
| 79 | 54 | naphthalen-2-yl | $^1$H-NMR(CDCl$_3$): δ=8.81(1H, s), 8.14 (1H, d), 8.00(1H, d), 7.89(2H, t), 7.50–7.64(2H, m), 7.18–7.31(3H, m), 6.95 (1H, d), 6.86(1H, s), 4.82(1H, dd), 4.56 (1H, dd), 4.02–4.29(2H, m), 3.31–3.43 (1H, m), 2.94(3H, s), 2.06–2.32(2H, m) ppm. |
| 80 | 55 | 2-fluoro-3-(trifluoromethyl)phenyl | $^1$H-NMR(CDCl$_3$): δ=8.44–8.58(2H, m), 7.25–7.35(2H, m), 7.17(2H, s), 6.90 (2H, m), 4.75(1H, dd), 4.59(1H, dd), 4.21–4.30(1H, m), 4.03–4.11(1H, m), 3.27–3.39(1H, m), 2.98(3H, s), 2.08–2.33 (2H, m)ppm. |

TABLE 7-continued

| Prep. no. | Starting material Prep. No. | R | Analytical Data |
|---|---|---|---|
| 81 | 52 | 5,6,7,8-tetrahydronaphthalen-1-yl | ¹H-NMR(CDCl₃): δ=7.37(1H, d), 7.05–7.31(5H, m), 6.99(1H, dd), 6.84(1H, s), 4.80(1H, dd), 4.65(1H, dd), 4.05–4.30 (2H, m), 3.30–3.40(1H, m), 2.97(3H, s), 2.65–2.85(4H, m), 2.10–2.30(2H, m), 1.70–1.85(4H, m)ppm. |
| 82 | 56 | 5,6,7,8-tetrahydronaphthalen-2-yl | ¹H-NMR(CDCl₃): δ=7.79–7.89(2H, m), 7.10–7.35(4H, m), 6.91(1H, dd), 6.81 (1H, s), 4.72(1H, dd), 4.51(1H, dd), 4.17–4.27(1H, m), 4.00–4.10(1H, m), 3.06–3.39(1H, m), 2.79–2.99(7H, m), 2.03–2.29(2H, m), 1.75–1.87(4H, m) ppm. |
| 83 | 53 | 4-methoxy-3-chlorophenyl (MeO, Cl substituted) | ¹H-NMR(CDCl₃): δ=7.31–7.42(3H, m), 7.21(1H, d), 7.07(1H, s), 6.99(1H, dd), 6.91(1H, d), 6.75(1H, s), 4.83(1H, dd), 4.48(1H, dd), 4.16–4.28(1H, m), 4.02–4.11(1H, m), 3.75(3H, s), 3.28–3.39 (1H, m), 2.92(3H, s), 2.02–2.28(2H, m) ppm. |
| 84 | 67 | 2-methoxyphenyl | ¹H-NMR(CDCl₃): δ=7.35–7.50(3H, m), 7.24(1H, d), 6.95–7.07(4H, m), 6.72 (1H, s), 4.89(1H, dd), 4.49(1H, dd), 4.19–4.28(1H, m), 4.05–4.14(1H, m), 3.79(3H, s), 3.30–3.41(1H, m), 2.94(3H, s), 2.06–2.29(2H, m), ppm. |
| 85 | 68 | 3,5-bis(trifluoromethyl)phenyl | ¹H-NMR(CDCl₃): δ=8.79(2H, s), 8.07 (1H, s), 7.32(1H, d), 7.20(2H, d), 6.91 (2H, d), 4.80(1H, dd), 4.61(1H, dd), 4.20–4.29(1H, m), 4.04–4.12(1H, m), 3.27–3.40(1H, m), 2.93(3H, s), 2.08–2.30 (2H, m)ppm. |
| 86 | 69 | 2-(trifluoromethyl)phenyl | ¹H-NMR(CDCl₃): δ=7.76(1H, d), 7.58–7.68(2H, m), 7.49(1H, d), 7.39(1H, d), 7.26(1H, d), 7.10(1H, s), 6.95(1H, dd), 6.80(1H, s), 4.91(1H, dd), 4.50(1H, dd), 4.22–4.30(1H, m), 4.05–4.15(1H, m), 3.30–3.41(1H, m), 2.98(3H, s), 2.07–2.30 (2H, m)ppm. |
| 87 | 70 | 2-isopropoxyphenyl | ¹H-NMR(CDCl₃): δ=7.32–7.46(3H, m), 7.24(1H, s), 6.92–7.07(4H, m), 6.71 (1H, s), 4.87(1H, dd), 4.40–4.56(2H, m), 4.18–4.27(1H, m), 4.04–4.11(1H, m), 3.30–3.42(1H, m), 2.94(3H, s), 2.07–2.27 (2H, m), 1.21(6H, d)ppm. |
| 88 | 71 | 2-ethylphenyl | ¹H-NMR(CDCl₃): δ=7.21–7.45(6H, m), 7.08(1H, s), 7.96(1H, dd), 6.85(1H, s), 4.82(1H, dd), 4.63(1H, dd), 4.20–4.30 (1H, m), 4.03–4.11(1H, m), 3.30–3.42 (1H, m), 2.94(3H, s), 2.68(2H, q), 2.06–2.31(2H, m), 1.21(3H, t)ppm. |

TABLE 7-continued

| Prep. no. | Starting material Prep. No. | R | Analytical Data |
|---|---|---|---|
| 89 | 72 | 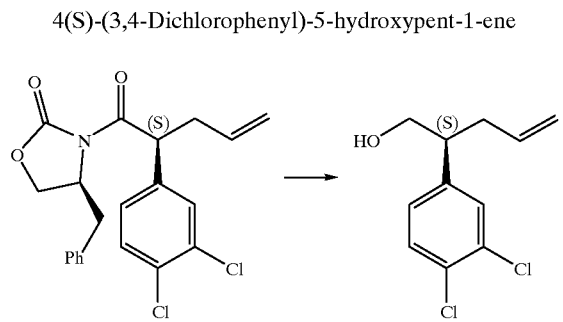 (phenoxyphenyl group, partial) | $^1$H-NMR(CDCl$_3$): δ=6.90–7.59(12H, m), 6.83(1H, dd), 6.63(1H, s), 4.80(1H, dd), 3.96–4.32(3H, m), 3.15–3.25(1H, m), 2.90(3H, s), 2.00–2.21(2H, m)ppm. |
| 90 | 73 | (benzyl group) | $^1$H-NMR(CDCl$_3$): δ=7.22–7.37(6H, m), 7.10(2H, dd), 6.81(1H, dd), 6.70 (1H, s), 4.76(1H, dd), 4.25–4.50(3H, m), 4.10–4.18(1H, m), 3.91–4.03(1H, m), 3.10–3.21(1H, m), 2.89(3H, s), 1.94–2.15 (2H, m)ppm. |

PREPARATION 91

4(S)-(3,4-Dichlorophenyl)-5-hydroxypent-1-ene

4(S)-Benzyl-3-(2(S)-(3,4-dichlorophenyl)pent-4-en-1-oyl)oxazolidin-2-one (30.32 g) (see Bioorganic and Medicinal Chemistry Letters, 3, 319, (1993)) was dissolved in if anhydrous tetrahydrofuran (400 ml), cooled in an ice-bath and lithium aluminium hydride (5.7 g) carefully added in two portions (exothermic reaction). The mixture was stirred at 0° C. for 20 minutes and then stirred at room temperature for 1 hour before being cooled to 0° C. Water (6 ml) was carefully added followed by 2N aqueous sodium hydroxide solution (6 ml) and fixrther water (12 ml). The mixture was stirred vigourously for 40 minutes and the resulting precipitate removed by filtration and washed with diethyl ether. The filtrate was collected and the organic and aqueous phases separated. The solvent was then removed from the organic phase under reduced pressure to give a yellow oil which was chromatographed on silica gel eluting with a solvent gradient of 4:1 changing to 4:0, by volume, dichloromethane-:hexane to give 4(S)-(3,4-dichlorophenyl)-5-hydroxypent-1-ene (11.74 g) as an oil.

$^1$H-NMR (CDCl$_3$): δ=7.24–7.45 (2H, m), 7.06 (1H, dd), 5.61–5.75 (1H, m), 4.96–5.10 (2H, m), 3.70–3.90 (2H, m), 2.80–2.91 (1H, m), 2.30–2.55 (2H, m), 1.32 (1H, t) ppm.

PREPARATION 92

4(R)-(3,4-Dichlorophenyl)-5-hydroxypent-1-ene

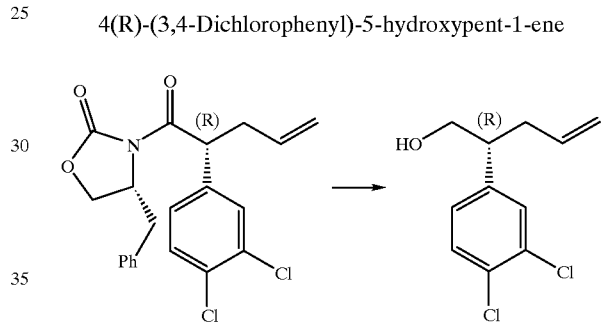

This compound was prepared by an analogous method to that used to prepare the compound of Preparation 91 using the appropriate starting material (see Bioorganic and Medicinal Chemistry Letters, 3, 319(1993)).

$^1$H-NMR (CDCl$_3$): δ=7.24–7.45 (2H, m), 7.06 (1H, dd), 5.61–5.75 (1H, m), 4.96–5.10 (2H, m), 3.70–3.90 (2H, m), 2.80–2.91 (1H, m), 2.30–2.55 (2H, m), 1.32 (1H, t) ppm.

PREPARATION 93

4(S)-(3,4-Dichlorophenyl)-5-(methanesulphonyloxy)pent-1-ene

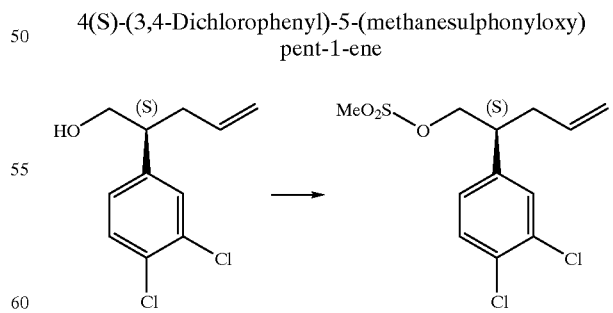

Methanesulphonyl chloride (3.55 g) was added dropwise to an ice-cooled solution of 4(S)-(3,4-dichlorophenyl)-5-hydroxypent-1-ene (6.0 g) (see Preparation 91) and triethylamine (3.48 g) in dichloromethane (100 ml) and the mixture stirred at room temperature for 1 hour. The solvent was then removed under reduced pressure and the residue partitioned between diethyl ether and water. The two phases were separated and the aqueous layer firrter extracted with diethyl ether. The organic pahses were then combined and washed sequentially with water, dilute aqueous citric acid solution, brine, saturated aqueous sodium hydrogen carbonate solution and brine before drying over anhydrous sodium sulphate. Removal of the solvent under reduced pressure gave 4(S)-(3,4-dichlorophenyl)-5-(methanesulphonyloxy)pent-1-ene (8.25 g) as an oil.

$^1$H-NMR (CDCl$_3$): δ=7.42 (1H, d), 7.30 (1H, s), 7.04 (1H, dd), 5.56–5.72 (1H, m), 5.01–5.10 (2H, m), 4.22–4.39 (2H, m), 3.05–3.15 (1H, m), 2.88 (3H, s), 2.33–2.60 (2H, m) ppm.

PREPARATION 94

4(R)-(3,4-Dichlorophenyl)-5-(methanesulphonyloxy)pent-1-ene

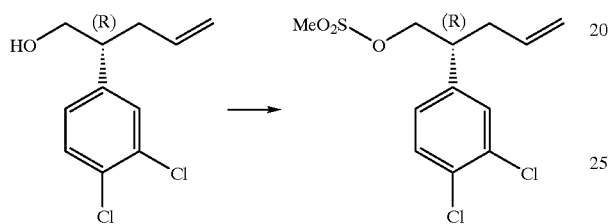

This compound was prepared by an analogous method to that used to prepare the compound of Preparation 93 using 4(R)-(3,4-dichlorophenyl)-5-hydroxypent-1-ene (see Preparation 92) as the starting material.

$^1$H-NMR (CDCl$_3$): δ=7.42 (1H, d), 7.30 (1H, s), 7.04 (1H, dd), 5.56–5.72 (1H, m), 5.01–5.10 (2H, m), 4.22–4.39 (2H, m), 3.05–3.15 (1H, m), 2.88 (3H, s), 2.33–2.60 (2H, m) ppm.

PREPARATION 95

4(S)-(3,4-Dichlorophenyl)-5-(imidazol-1-yl)pent-1-ene

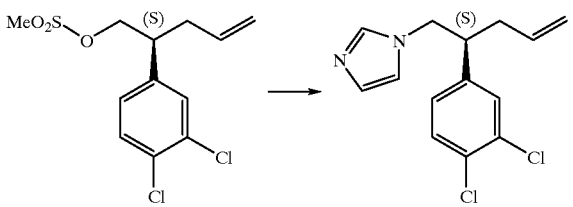

4(S)-(3,4-Dichlorophenyl)-5-(methanesulphonyloxy)pent-1-ene (8.25 g) (see Preparation 93) and imidazole (5.3 g) were dissolved in anhydrous acetonitrile (80 ml) and the mixture heated under reflux for 6 days. The solvent was removed under reduced pressure to give a residue which was partitioned between diethyl ether and aqueous saturated sodium hydrogen carbonate solution (pH of the aqueous phase was kept >7). The phases were separated and the aqueous phase extracted with diethyl ether. The combined organic extracts were then washed with water, dried over anhydrous sodium sulphate and the solvent removed under reduced pressure to give a residue which was chromatographed on silica gel, eluting with a solvent gradient of 98:2 changing to 95:5, by volume, dichloromethane:methanol to give 4(S)-(3,4-dichlorophenyl)-5-(imidazol-1-yl)pent-1-ene (4.78 g) as an oil.

$^1$H-NMR (CDCl$_3$): δ=7.35 (1H, d), 7.15–7.30 (2H, m), 6.99 (1H, s), 6.84 (1H, d), 6.69 (1H, s), 5.55–5.70 (1H, m), 5.07 (2H, d), 3.95–4.22 (2H, m), 2.95–3.10 (1H, m), 2.32–2.45 (2H, m) ppm.

PREPARATION 96

4(R)-(3,4-Dichlorophenyl)-5-(imidazol-1-yl)pent-1-ene

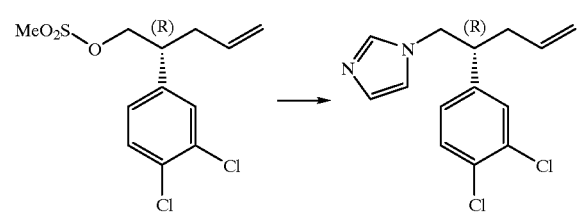

This compound was prepared by an analogous method to that used to prepare the compound of Preparation 95 using 4(R)-(3,4-dichlorophenyl)-5-(methanesulphonyloxy)pent-1-ene (see Preparation 94) as the starting material.

$^1$H-NMR (CDCl$_3$): δ=7.35 (1H, d), 7.15–7.30 (2H, m), 6.99 (1H, s), 6.84 (1H, d), 6.69 (1H, s), 5.55–5.70 (1H, m), 5.07 (2H, d), 3.95–4.22 (2H, m), 2.95–3.10 (1H, m), 2.32–2.45 (2H, m) ppm.

PREPARATION 97

3(S)-(3,4-Dichlorophenyl)-4-(imidazol-1-yl)butan-1-al

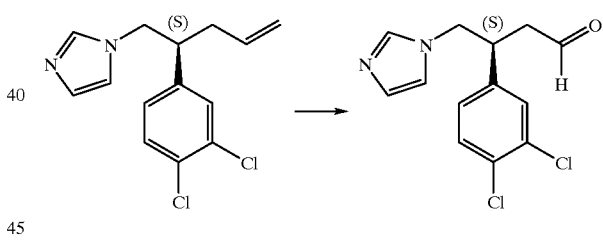

4(S)-(3,4-Dichlorophenyl)-5-(imidazol-1-yl)pent-1-ene (4.75 g) (see Preparation 95) was dissolved in a mixture of acetonitrile (75 ml), water (13 ml) and 1N aqueous hydrochloric acid solution (17 ml). Osmium tetroxide (3.4 ml of a 0.05M solution in toluene) was added and the mixture stirred for 20 minutes. Sodium periodate (5.3 g) was then added together with a further quantity of acetonitrile (30 ml) and stirring continued overnight. Water (ca. 100 ml) was added and the acetonitrile removed under reduced pressure to give an aqueous suspension which was basified to pH>7 by the addition of solid sodium carbonate. The mixture was then extracted (three times) with ethyl acetate and the combined organic extracts washed sequentially with water and brine before being dried over anhydrous sodium sulphate. Removal of the solvent under reduced pressure gave 3(S)-(3,4-dichlorophenyl)-4-(imidazol-1-yl)butan-1-al (4.3 g) as an oil.

$^1$H-NMR (CDCl$_3$): δ=9.70 (1H, s), 7.38 (1H, d), 7.20–7.30 (2H, m), 7.01 (1H, s), 6.89 (1H, dd), 6.71 (1H, s), 4.00–4.22 (2H, m), 3.60 (1H, m), 2.72–2.92 (2H, m) ppm.

PREPARATION 98

3(R)-(3,4-Dichlorophenyl)-4-(imidazol-1-yl)butan-1-al

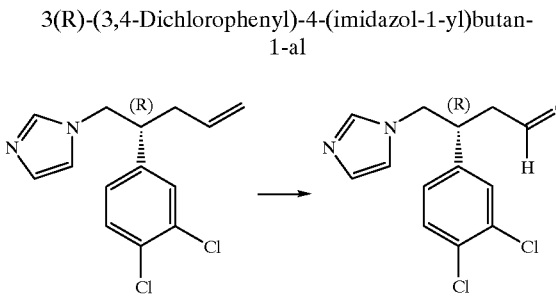

This compound was prepared by an analogous method to that used to prepare the compound of Preparation 97 using 4(R)-(3,4-dichlorophenyl)-5-(imidazol-1-yl)pent-1-ene (see Preparation 96) as the starting material.

$^1$H-NMR (CDCl$_3$): δ=9.70 (1H, s), 7.38 (1H, d), 7.20–7.30 (2H, m), 7.01 (1H, s), 6.89 (1H, dd), 6.71 (1H, s), 4.00–4.22 (2H, m), 3.60 (1H, m), 2.72–2.92 (2H, m) ppm.

PREPARATION 99

3(S)-(3,4-Dichlorophenyl)-4-(imidazol-1-yl)butan-1-ol

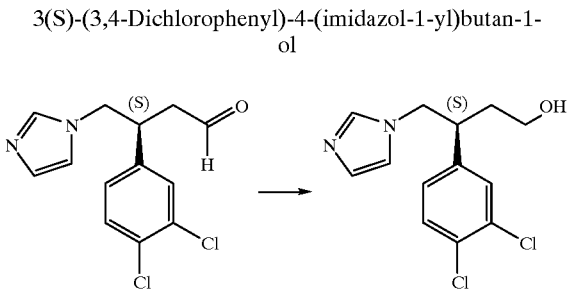

Sodium borohydride (0.68 g) was added carefully to an ice-cooled solution of 3(S)-3,4-dichlorophenyl)-4-(imidazol-1-yl)butan-1-al (4.3 g) (see Preparation 97) in ethanol (40 ml) and the mixture stirred at room temperature for one hour before removing the solvent under reduced pressure to give a residue. The residue was suspended in water (30 ml), cooled in an ice-bath and the mixture first acidified to pH1 with 2N aqueous hydrochloric acid solution and then basified to pH14 by addition of 2N aqueous sodium hydroxide solution. The resulting suspension was filtered and the residue washed with water, dried and then crystallised from acetonitrile to give 3(S)-(3,4-dichlorophenyl)-4-(imidazol-1-yl)butan-1-ol (1.37 g) as a cream solid.

$^1$H-NMR (CDCl$_3$): δ=7.35 (1H, d), 7.15–7.30 (2H, m), 6.95 (1H, s), 6.89 (1H, d), 6.70 (1H, s), 4.00–4.25 (2H, m), 3.60–3.70 (1H, m), 3.40–3.50 (1H, m), 3.15–3.30 (1H, m), 2.10 (1H, br. s), 1.75–2.00 (2H, m) ppm.

PREPARATION 100

3(R)-(3,4-Dichlorophenyl-4-(imidazol-1-yl)butan-1-ol

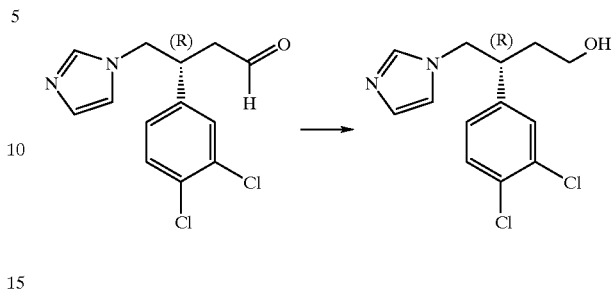

This compound was prepared by an analogous method to that used to prepare the compound of Preparation 99 using 3(R)-(3,4-dichlorophenyl)-4-(imidazol-1-yl)butan-1-al (see Preparation 98) as the starting material.

$^1$H-NMR (CDCl$_3$): δ=7.35 (1H, d), 7.15–7.30 (2H, m), 6.95 (1H, s), 6.89 (1H, d), 6.70 (1H, s), 4.00–4.25 (2H, m), 3.60–3.70 (1H, m), 3.40–3.50 (1H, m), 3.15–3.30 (1H, m), 2.10 (1H, br. s), 1.75–2.00 (2H, m) ppm.

PREPARATION 101

3(S)-(3,4-Dichlorophenyl)-4-[2-(1,2,3,4-tetrahydro-5-naphthoyl)imidazol-1-yl]butyl 1,2,3,4-tetrahydro-5-naphthoate

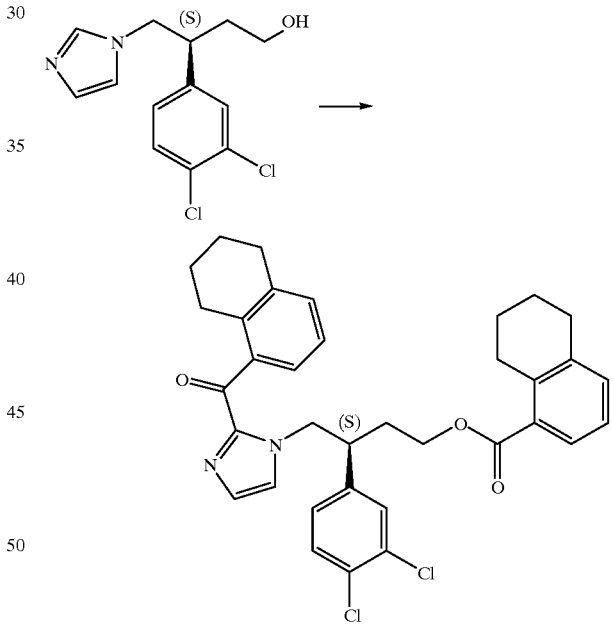

1,2,3,4-Tetrahydro-5-naphthoyl chloride (1.70 g) (see Preparation 36) was added dropwise to a suspension of 3(S)-(3,4-dichlorophenyl)-4-(imidazol-1-yl)butan-1-ol (0.90 g) (see Preparation 99) and triethylamine (1.45 g) in anhydrous acetonitrile (15 ml) and the solution stirred at room temperature for 4 days. The solvent was then removed under reduced pressure to give a residue which was partitioned between ethyl acetate and saturated aqueous sodium hydrogen carbonate solution. The phases were separated and the aqueous phase further extracted with ethyl acetate. The organic phases were combined, washed sequentially with water and brine, dried over anhydrous sodium sulphate and the solvent removed under reduced pressure to give a residue which was chromatographed on silica gel eluting with a solvent gradient of 2:1 changing to 0:1, by volume, pentane:ethyl acetate to give 3(S)-(3,4-dichlorophenyl)-4-[2-(1,2,3,4-tetrahydro-5-naphthoyl)imidazol-1-yl]butyl 1,2,3,4-tetrahydro-5-naphthoate (1.38 g) as a gum.

$^1$H-NMR (CDCl$_3$): δ=7.50 (1H, d), 6.95–7.38 (10H, m), 4.83 (1H, dd), 4.63 (1H, m), 4.30–4.35 (1H, m), 4.08–4.16 (1H, m), 3.30–3.40 (1H, m), 3.00 (2H, br. s), 2.63–2.84 (6H, m), 2.10–2.25 (2H, m), 1.67–1.83 (8H, m) ppm.

PREPARATION 102

3(R)-(3,4-Dichlorophenyl)-4-[2-(1,2,3,4-tetrahydro-5-naphthoyl)imidazol-1-yl]butyl 1,2,3,4-tetrahydro-5-naphthoate This compound was prepared by an analogous method to that used to prepare the compound of Preparation 101 using 3(R)-(3,4-dichlorophenyl)-4-(imidazol-1-yl)butan-1-ol (see Preparation 100) as the starting material.

$^1$H-NMR (CDCl$_3$): δ=7.50 (1H, d), 6.95–7.38 (10H, m), 4.83 (1H, dd), 4.63 (1H, m), 4.30–4.35 (1H, m), 4.08–4.16 (1H, m), 3.30–3.40 (1H, m), 3.00 (2H, br. s), 2.63–2.84 (6H, m), 2.10–2.25 (2H, m), 1.67–1.83 (8H, m) ppm.

PREPARATION 103

3(S)-(3,4-Dichlorophenyl)-4-[2-(1,2,3,4-tetrahydro-5-naphthoyl)imidazol-1-yl]butan-1-ol

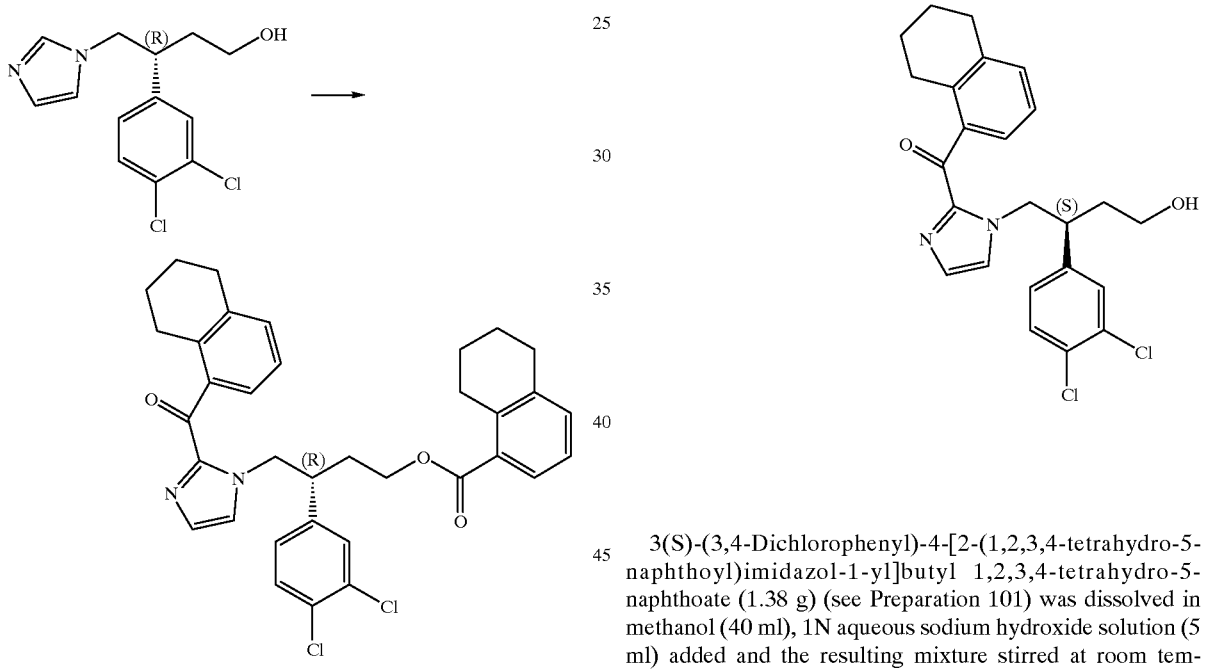

3(S)-(3,4-Dichlorophenyl)-4-[2-(1,2,3,4-tetrahydro-5-naphthoyl)imidazol-1-yl]butyl 1,2,3,4-tetrahydro-5-naphthoate (1.38 g) (see Preparation 101) was dissolved in methanol (40 ml), 1N aqueous sodium hydroxide solution (5 ml) added and the resulting mixture stirred at room temperature overnight. The methanol was then removed under reduced pressure and the residue partitioned between ethyl acetate and water. The organic phase was separated, washed sequentially with saturated aqueous sodium hydrogen carbonate solution and brine, dried over anhydrous sodium sulphate and the solvent removed under reduced pressure to give 3(S)-(3,4-dichlorophenyl)-4-[2-(1,2,3,4-tetrahydro-5-naphthoyl)imidazol-1-yl]butan-1-ol (0.82 g) as a gum.

$^1$H-NMR (CDCl$_3$): δ=7.10–7.35 (5H, m), 7.06 (1H, s), 6.92 (1H, dd), 6.74 (1H, s), 4.90 (1H, dd), 4.50 (1H, dd), 3.70–3.82 (1H, m), 3.53–3.64 (1H, m), 3.30–3.42 (1H, m), 2.70–2.86 (4H, m), 1.70–2.04 (6H, m) ppm.

PREPARATION 104

3(R)-(3,4-Dichlorophenyl)-4-[2-(1,2,3,4-tetrahydro-5-naphthoyl)imidazol-1-yl]butan-1-ol

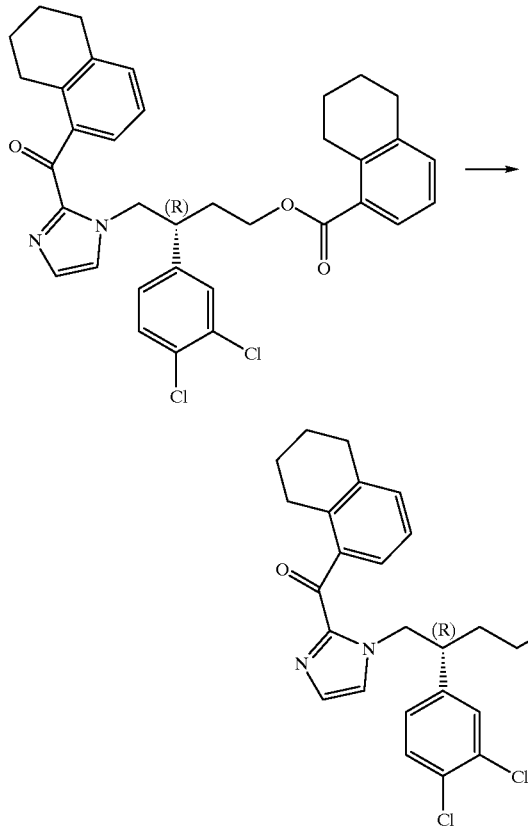

This compound was prepared by an analogous method to that used to prepare the compound of Preparation 103 using 3(R)-(3,4-dichlorophenyl)-4-[2-(1,2,3,4-tetrahydro-5-naphthoyl)imidazol-1-yl]butyl 1,2,3,4-tetrahydro-5-naphthoate (see Preparation 102) as the starting material.

$^1$H-NMR (CDCl$_3$): δ=7.10–7.35 (5H, m), 7.06 (1H, s), 6.92 (1H, dd), 6.74 (1H, s), 4.90 (1H, dd), 4.50 (1H, dd), 3.70–3.82 (1H, m), 3.53–3.64 (1H, m), 3.30–3.42 (1H, m), 2.70–2.86 (4H, m), 1.70–2.04 (6H, m) ppm.

PREPARATION 105

1-Methanesulphonyloxy-3(S)-(3,4-dichlorophenyl)-4-[2-(1,2,3,4-tetrahydro-5-naphthoyl)imidazol-1-yl]butane

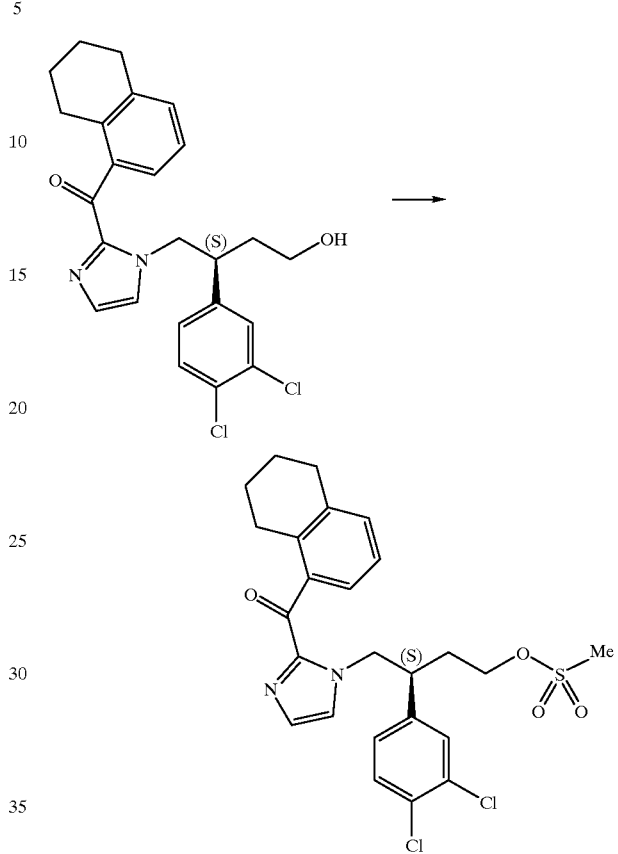

3(S)-(3,4-Dichlorophenyl)-4-[2-(1,2,3,4-tetrahydro-5-naphthoyl)imidazol-1-yl]butan-1-ol (0.68 g) (see Preparation 103) and triethylamine (0.22 g) were dissolved in dichloromethane (15 ml), the solution cooled in an ice-bath and methanesulphonyl chloride (0.22 g) added. The mixture was stirred for 4 hours before removal of the solvent under reduced pressure to give a residue which was partitioned between ethyl acetate and water. The organic phase was separated and washed with saturated aqueous sodium hydrogen carbonate solution before being dried over anhydrous sodium sulphate. The solvent was removed under reduced pressure to give 1-methanesulphonyloxy-3(S)-(3,4-dichlorophenyl)-4-[2-(1,2,3,4-tetrahydro-5-naphthoyl)imidazol-1-yl]butane (0.82 g) as an oil.

$^1$H-NMR (CDCl$_3$): δ=7.37 (1H, d), 7.05–7.31 (5H, m), 6.99 (1H, dd), 6.84 (1H, s), 4.80 (1H, dd), 4.65 (1H, dd), 4.05–4.30 (2H, m), 3.30–3.40 (1H, m), 2.97 (3H, s), 2.65–2.85 (4H, m), 2.10–2.30 (2H, m), 1.70–1.85 (4H, m) ppm.

PREPARATION 106

1-Methanesulphonyloxy-3(R)-(3,4-dichlorophenyl)-
4-[2-(1,2,3,4-tetrahydro-5-naphthoyl)imidazol-1-yl]
butane

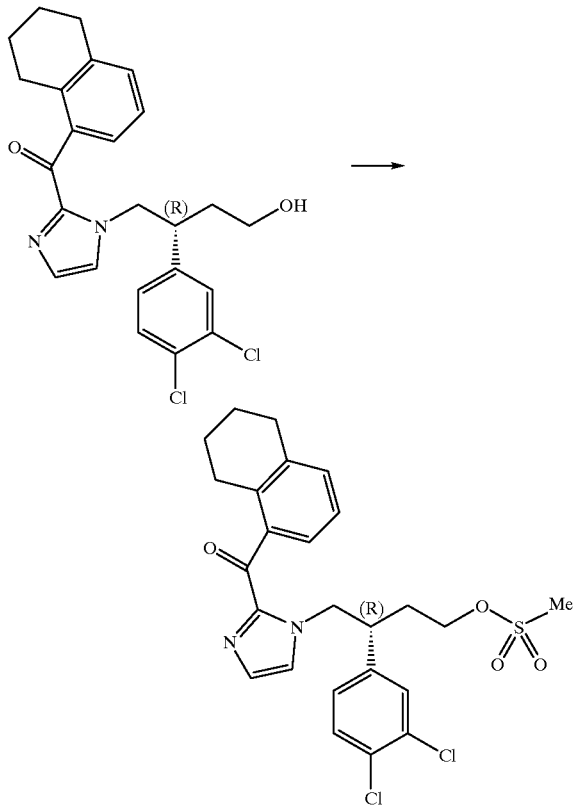

This compound was prepared by an analogous method to that used to prepare the compound of Preparation 105 using 3(R)-(3,4-dichlorophenyl)-4-[2-(1,2,3,4-tetrahydro-5-naphthoyl)imidazol-1-yl]butan-1-ol (see Preparation 104) as the starting material.

$^1$H-NMR (CDCl$_3$): δ=7.37 (1H, d), 7.05–7.31 (5H, m), 6.99 (1H, dd), 6.84 (1H, s), 4.80 (1H, dd), 4.65 (1H, dd), 4.05–4.30 (2H, m), 3.30–3.40 (1H, m), 2.97 (3H, s), 2.65–2.85 (4H, m), 2.10–2.30 (2H, m), 1.70–1.85 (4H, m) ppm.

PHARMACOLOGICAL DATA

The affinities of the following compounds of the Examples for the human NK$_1$ and NK$_2$ receptors were determined by the methods described on page 24, lines 8 to 22, of the description, and the results are presented in the Table below.

| Example No. | NK1 Binding (IC$_{50}$) | NK2 Binding (IC$_{50}$) |
|---|---|---|
| Example 2 | 0.6 nM | 4 nM |
| Example 5 | 8 nM | 11 nM |
| Example 6 | 9 nM | 96 nM |
| Example 18 | 123 nM | 3 nM |
| Example 19 | 2 nM | 24 nM |

These data show that the compounds are dual NK$_1$ and NK$_2$ receptor antagonists.

What is claimed is:

1. A compound of the formula:

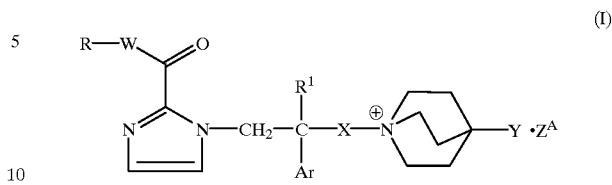

wherein

R is phenyl, C$_3$–C$_7$ cycloalkyl or heteroaryl, each of which being optionally benzo- or C$_3$–C$_7$ cycloalkyl-fused and optionally substituted, including in the benzo- or C$_3$–C$_7$ cycloalkyl-fused portion, by from 1 to 3 substituents each independently selected from C$_1$–C$_4$ alkyl, fluoro(C$_1$–C$_4$)alkyl, C$_1$–C$_4$ alkoxy, fluoro(C$_1$–C$_4$)alkoxy, phenoxy, C$_2$–C$_4$ alkanoyl, halo, C$_1$–C$_4$ alkoxycarbonyl, C$_3$–C$_7$ cycloalkyl, —S(O)$_m$(C$_1$–C$_4$ alkyl), cyano, —NR$^2$R$^3$, —S(O)$_m$NR$^2$R$^3$, —NR$^4$(C$_1$–C$_4$ alkanoyl) and —CONR$^2$R$^3$, or R is 2,3-dihydrobenzo[b]furanyl or chromanyl;

R$^1$ is H or C$_1$–C$_6$ alkyl;

R$^2$ and R$^3$ are either each independently selected from H and C$_1$–C$_6$ alkyl, or when taken together, represent C$_4$–C$_6$ alkylene;

R$^4$ is H or C$_1$–C$_6$ alkyl;

W is a direct link, methylene or ethylene;

X is unbranched C$_2$–C$_4$ alkylene;

Y is phenyl, naphthyl, benzyl, pyridyl, thienyl or C$_3$–C$_7$ cycloalkyl, each of which being optionally substituted by from 1 to 3 substituents each independently selected from C$_1$–C$_4$ alkyl, fluoro(C$_1$–C$_4$)alkyl, C$_1$–C$_4$ alkoxy, fluoro(C$_1$–C$_4$)alkoxy, halo and cyano;

Ar is phenyl, naphthyl, benzyl, thienyl, benzo[b]thienyl or indolyl, each of which being optionally substituted by from 1 to 3 substituents each independently selected from C$_1$–C$_4$ alkyl, fluoro(C$_1$–C$_4$)alkyl, C$_1$–C$_4$ alkoxy, fluoro(C$_1$–C$_4$)alkoxy, halo and cyano, or Ar is 1,3-benzodioxolan-4 or 5-yl or 1,4-benzodioxan-5 or 6-yl;

m is 0, 1 or 2;

Z$^A$ is a pharmaceutically acceptable anion;

and "heteroaryl", used in the definition of R, means thienyl or a 5- or 6-membered ring heteroaryl group containing either from 1 to 4 nitrogen heteroatoms, or 1 or 2 nitrogen heteroatom(s) and 1 oxygen or sulphur heteroatom, with the proviso that when W is a direct link and R is optionally fused and optionally substituted heteroaryl, said heteroaryl is linked by a ring carbon atom to the carbonyl group.

2. A compound according to claim 1 wherein R is phenyl which is optionally benzo- or C$_3$–C$_7$ cycloalkyl-fused and optionally substituted, including in the benzo- or C$_3$–C$_7$ cycloalkyl-fused portion, by 1, 2 or 3 substituents each independently selected from C$_1$–C$_4$ alkyl, fluoro(C$_1$–C$_4$) alkyl, C$_1$–C$_4$ alkoxy, fluoro(C$_1$–C$_4$)alkoxy, phenoxy and halo, or R is 2,3-dihydrobenzo[b]furanyl.

3. A compound according to claim 1 wherein R is phenyl which is optionally benzo- or C$_3$–C$_7$ cycloalkyl-fused and optionally substituted, including in the benzo- or C$_3$–C$_7$ cycloalkyl-fused portion, by 1, 2 or 3 substituents each independently selected from methyl, ethyl, trifluoromethyl, methoxy, isopropoxy, trifluoromethoxy, phenoxy, fluoro and chloro, or R is 2,3-dihydrobenzo[b]furanyl.

4. A compound according to claim 1 wherein R is phenyl, naphthyl or tetrahydronaphthyl, each of which being optionally substituted by 1, 2 or 3 substituents each independently selected from methyl, ethyl, trifluoromethyl, methoxy, isopropoxy, trifluoromethoxy, phenoxy, fluoro and chloro, or R is 2,3 dihydrobenzo[b]furanyl.

5. A compound according to claim 1 wherein R is phenyl, 3,5-dimethylphenyl, 2,3-dimethylphenyl, 2-trifluoromethoxyphenyl, 2-methoxy-3-methylphenyl, 2,3-dihydrobenzo[b]furan-7-yl, naphth-2-yl, 4-fluoro-3-trifluoromethylphenyl, 1,2,3,4-tetrahydronaphth-5-yl, 1,2,3,4-tetrahydronaphth-6-yl, 5-chloro-2-methoxyphenyl, 2-methoxyphenyl, 2-trifluoromethylphenyl, 2-isopropoxyphenyl, 2-ethylphenyl, 2-phenoxyphenyl or 3,5-bis(trifluoromethyl)phenyl.

6. A compound according to claim 1 wherein R is 2,3-dimethylphenyl, naphth-2-yl, 1,2,3,4-tetrahydronaphth-5-yl or 2-methoxyphenyl.

7. A compound according to claim 1 wherein $R^1$ is H.

8. A compound according to claim 1 wherein W is a direct link or methylene.

9. A compound according to claim 1 wherein W is a direct link.

10. A compound according to claim 1 wherein X is 1,2-ethylene.

11. A compound according to claim 1 wherein Y is phenyl, naphthyl or cyclohexyl, each of which being optionally substituted by 1, 2 or 3 $C_1$–$C_4$ alkyl substituents.

12. A compound according to claim 1 wherein Y is phenyl, 3,5-dimethylphenyl, cyclohexyl or naphth-2-yl.

13. A compound according to claim 1 wherein Y is phenyl.

14. A compound according to claim 1 wherein Ar is phenyl optionally substituted by 1, 2 or 3 halo substituents.

15. A compound according to claim 1 wherein Ar is phenyl substituted by 1 or 2 chloro substituents.

16. A compound according to claim 1 wherein Ar is 3,4-dichlorophenyl.

17. A compound according to claim 1 wherein $Z^A$ is chloride, bromide, nitrate, methanesulphonate, para-toluenesulphonate, benzenesulphonate, hydrogen sulphate or sulphate.

18. A compound according to claim 1 wherein $Z^A$ is chloride or methanesulphonate.

19. A compound according to claim 1 wherein $Z^A$ is methanesulphonate.

20. A compound according to claim 1 wherein $R^1$ is H, X is —$CH_2CH_2$— and Ar is 3,4-dichlorophenyl, and wherein R—W— is 3,5-dimethylphenyl, Y is phenyl and $Z^A$ is $CH_3SO_3$—;

R—W— is 2,3-dimethylphenyl, Y is phenyl and $Z^A$ is $CH_3SO_3$—;

R—W— is 2-trifluoromethoxyphenyl, Y is phenyl and $Z^A$ is $CH_3SO_3$—;

R—W— is 2-methoxy-3-methylphenyl, Y is phenyl and $Z^A$ is $CH_3SO_3$—;

R—W— is 2,3-dihydrobenzo[b]furan-7-yl, Y is phenyl and $Z^A$ is $CH_3SO_3$—;

R—W— is naphth-2-yl, Y is phenyl and $Z^A$ is $CH_3SO_3$—;

R—W— is 4-fluoro-3-trifluoromethylphenyl, Y is phenyl and $Z^A$ is $CH_3SO_3$—

R—W— is 1,2,3,4-tetrahydronaphth-5-yl, Y is phenyl and $Z^A$ is $CH_3SO_3$—;

R—W— is 1,2,3,4-tetrahydronaphth-6-yl, Y is phenyl and $Z^A$ is $CH_3SO_3$—;

R—W— is 5-chloro-2-methoxyphenyl, Y is phenyl and $Z^A$ is $CH_3SO_3$—;

R—W— is 2-methoxyphenyl, Y is phenyl and $Z^A$ is $CH_3SO_3$—;

R—W— is 2-trifluoromethylphenyl, Y is phenyl and $Z^A$ is $CH_3SO_3$—;

R—W— is 2-isopropoxyphenyl, Y is phenyl and $Z^A$ is $CH_3SO_3$—;

R—W— is 2-ethylphenyl, Y is phenyl and $Z^A$ is $CH_3SO_3$—;

R—W— is 2-phenoxyphenyl, Y is phenyl and $Z^A$ is $CH_3SO_3$—;

R—W— is benzyl, Y is phenyl and $Z^A$ is $CH_3SO_3$—;

R—W— is 3,5-bis(trifluoromethyl)phenyl, Y is phenyl and $Z^A$ is Cl—;

R—W— is 2-methoxyphenyl, Y is cyclohexyl and $Z^A$ is $CH_3SO_3$—;

R—W— is 4-fluoro-3-trifluoromethylphenyl, Y is cyclohexyl and $Z^A$ is $CH_3SO_3$—;

R—W— is 2-methoxyphenyl, Y is 3,5-dimethylphenyl and $Z^A$ is $CH_3SO_3$—; or

R—W— is 2-methoxyphenyl, Y is naphth-2-yl and $Z^A$ is $CH_3SO_3$—;

or wherein $Z^A$ is an alternative pharmaceutically acceptable anion in respect of any thereof.

21. A compound according to claim 1 which is 4-phenyl-1-(3(S)-[3,4-dichlorophenyl]-4-[2-(1,2,3,4-tetrahydro-5-naphthoyl)imidazol-1-yl]butyl) quinuclidinium methanesulphonate or

[4-phenyl-1-(3(R)-[3,4-dichlorophenyl]-4-[2-(1,2,3,4-tetrahydro-5-naphthoyl)-imidazol-1-yl]butyl) quinuclidinium methanesulphonate]

4-phenyl-1-(3(R)-[3,4-dichlorophenyl]-4-[2-(1,2,3,4-tetrahydro-5-naphthoyl)-imidazol-1-yl]butyl) quinuclidinium methanesulphonate.

22. A process for the preparation of a compound of the formula (I) as claimed in claim 1 wherein R, $R^1$, W, X, Y, Ar and $Z^A$ are as defined in claim 1 comprising reaction of a compound of the formula:

(II)

R—W—C(=O)—[imidazole]—N—$CH_2$—C(R$^1$)(Ar)—X—(Z or $Z^1$)

wherein R, $R^1$, Ar, W and X are as previously defined for a compound of the formula (I) in this claim, Z is a leaving group capable of forming a pharmaceutically acceptable anion ($Z^A$) and $Z^1$ is a leaving group, with a compound of the formula:

(III)

[quinuclidine]—Y wherein Y is as previously defined for a compound of the formula (I), said process being followed by either (a), where $Z^1$ is a leaving group, exchange for a pharmaceutically acceptable anion ($Z^A$), or (b), optionally, where $Z^A$ is a pharmaceutically acceptable anion, exchange for another pharmaceutically acceptable anion.

23. A process as claimed in claim 22 wherein Z is $C_1$–$C_4$ alkanesulphonyloxy, benzenesulphonyloxy, para-toluenesulphonyloxy, chloro, bromo or iodo, and $Z^1$ is trifluoromethanesulphonyloxy.

24. A process as claimed in claim 22 wherein Z is methanesulphonyloxy and $Z^A$ is methanesulphonate.

25. A pharmaceutical composition comprising a compound of the formula (I) according to claim 1, together with a pharmaceutically acceptable diluent or carrier.

26. A method of treatment of a human to treat a disease by producing an antagonist effect on a tachykinin receptor or on a combination of tachykinin receptors, which comprises treating said human with an effective amount of a compound of the formula (I) according to claim 1 or with a pharmaceutically acceptable composition thereof.

27. A method according to claim 26 where the antagonist effect is on the human $NK_1$ and $NK_2$ tachykinin receptors.

28. A method according to claim 26 where the disease is an inflammatory disease such as arthritis, psoriasis, asthma or inflammatory bowel disease, a central nervous system (CNS) disorder such as anxiety, depression, dementia or psychosis, a gastro-intestinal (GI) disorder such as functional bowel disease, irritable bowel syndrome, gastro-oesophageal reflux, faecal incontinence, colitis or Crohn's disease, a disease caused by *Helicobacter pylori* or another urease-positive Gram negative bacteria, a urogenital tract disorder such as incontinence, hyperreflexia or cystitis, a pulmonary disorder such as chronic obstructive airways disease, an allergy such as eczema, contact dermatitis, atopic dermatitis or rhinitis, a hypersensitivity disorder such as to poison ivy, a peripheral neuropathy such as diabetic neuropathy, neuralgia, causalgia, painful neuropathy, a burn, herpetic neuralgia or postherpetic neuralgia, emesis, cough, migraine or acute or chronic pain.

\* \* \* \* \*